United States Patent
Baker et al.

(10) Patent No.: US 9,493,547 B2
(45) Date of Patent: Nov. 15, 2016

(54) BINDING PROTEINS TO THE CONSTANT REGION OF IMMUNOGLOBULIN G

(71) Applicant: UNIVERSITY OF WASHINGTON THROUGH ITS CENTER FOR COMMERCIALIZATION, Seattle, WA (US)

(72) Inventors: David Baker, Seattle, WA (US); Eva-Maria Strauch, Seattle, WA (US); Sarel Jacob Fleishman, Rehovot (IL)

(73) Assignee: University of Washington Through its Center for Commercialization, Seattle, WA (US)

( * ) Notice: Subject to any disclaimer, the term of this patent is extended or adjusted under 35 U.S.C. 154(b) by 21 days.

(21) Appl. No.: 14/387,699

(22) PCT Filed: Mar. 25, 2013

(86) PCT No.: PCT/US2013/033721
§ 371 (c)(1),
(2) Date: Sep. 24, 2014

(87) PCT Pub. No.: WO2013/148583
PCT Pub. Date: Oct. 3, 2013

(65) Prior Publication Data
US 2015/0037312 A1    Feb. 5, 2015

Related U.S. Application Data

(60) Provisional application No. 61/615,642, filed on Mar. 26, 2012.

(51) Int. Cl.
*A61K 38/16* (2006.01)
*A61K 38/00* (2006.01)
*C07K 5/00* (2006.01)
*C07K 7/00* (2006.01)
*C07K 16/00* (2006.01)
*C07K 17/00* (2006.01)
*C07K 1/00* (2006.01)
*C07K 1/22* (2006.01)
*C07K 14/00* (2006.01)
*A61K 38/50* (2006.01)
*C12N 9/80* (2006.01)
*G01N 33/68* (2006.01)

(52) U.S. Cl.
CPC .............. *C07K 16/00* (2013.01); *A61K 38/50* (2013.01); *C07K 1/22* (2013.01); *C07K 14/001* (2013.01); *C12N 9/80* (2013.01); *G01N 33/6854* (2013.01); *C12Y 305/01019* (2013.01)

(58) Field of Classification Search
None
See application file for complete search history.

(56) References Cited

U.S. PATENT DOCUMENTS

2003/0181692 A1* 9/2003 Ni .................. C07K 14/47
536/23.1
2004/0214272 A1* 10/2004 La Rosa .............. C07H 21/04
435/69.1

FOREIGN PATENT DOCUMENTS

EP    1923464 A1    5/2008

OTHER PUBLICATIONS

UniProt Database, Accession No. Q9G4G7, 6 pages (2001).*
Kabanov et al., Angew Chem Int Ed Engl. 48: 5418-5429 (2009).*
UniProt Database, Accession No. O58727, 7 pages (first available 1998).*
Arnold et al. (Jul. 2011) "Antibody purification by affinity chromatography based on small molecule affinity ligands identified by SPR-based screening of chemical microarrays," Journal of Chromatography A, 1218(29):4649-4659.
Baker et al. (Aug. 2001) "Electrostatics of nanosystems: application to microtubules and the ribosome," Proceedings of the National Academy of Sciences USA, 98(18):10037-10041.
Benatuil et al. (Apr. 2010) "An improved yeast transformation method for the generation of very large human antibody libraries," Protein Engineering, Design and Selection, 23(4):155-159.
Braisted and JA Wells (Jun. 1996) "Minimizing a binding domain from protein A," Proceedings of the National Academy of Sciences USA, 93(12):5688-5692.
Chao et al. (Jul. 2006) "Isolating and engineering human antibodies using yeast surface display," Nature Protocols, 1 (2):755-768.
Cohen et al. (Mar. 2003) "An integrated analysis of the genome of the hyperthermophilic archaeon Pyrococcus abyssi," Molecular Microbiology, 47(6):1495-1512.
Cooper et al. (Aug. 2010) "Predicting protein structures with a multiplayer online game," Nature, 466(7307):756-760.
Database UniProt (Mar. 1, 2001) "Cytochrome c oxidase subunit 2," XP002698641, retrieved from EBI accession No. UNIPROT:Q9G4G7.
DeLano et al. (Feb. 2000) "Convergent solutions to binding at a protein-protein interface," Science, 287 (5456):1279-1283.
Du et al. (Nov. 2001) "Crystal structure and mechanism of catalysis of a pyrazinamidase from Pyrococcus horikoshii," Biochemistry, 40(47):14166-14172.
Fleishman et al. (Jun. 2011) "RosettaScripts: a scripting language interface to the Rosetta macromolecular modeling suite," PLoS One, 6(6):e20161.
Fleishman et al. (May 2011) "Computational design of proteins targeting the conserved stem region of influenza hemagglutinin," Science, 332(6031):816-821.
Fleishman et al. (Nov. 2011) "Hotspot-centric de novo design of protein binders," Journal of Molecular Biology, 413 (5):1047-1062.
Fowler et al. (Sep. 2010) "High-resolution mapping of protein sequence-function relationships," Nature Methods, 7 (9):741-746.
IPRP dated Oct. 9, 2014 for PCT/US2013/033721 filed Mar. 25, 2013.
ISR/WO mailed Jun. 27, 2013 for PCT/US2013/033721 filed Mar. 25, 2013.
Kabir (Jan. 2002) "Immunoglobulin Purification by Affinity Chromatogrpahy Using Protein a Mimetic Ligands Prepared by Combinatorial Chemical Synthesis," Immunological Investigations, Informa Healthcare, 31(3/04):263-278.

(Continued)

Primary Examiner — Hasan Ahmed
Assistant Examiner — Thea D'Ambrosio
(74) Attorney, Agent, or Firm — McDonnell Boehnen Hulbert & Berghoff LLP

(57) ABSTRACT

The present invention provides polypeptides that bind to immunoglobulin G and methods for their use.

17 Claims, 4 Drawing Sheets

(56) References Cited

OTHER PUBLICATIONS

Kawarabayasi et al. (Apr. 1998) "Complete sequence and gene organization of the genome of a hyper-thermophilic archaebacterium, Pyrococcus horikoshii OT3," DNA Research, 5(2):55-76.

Kelley (Sep.-Oct. 2009) "Industrialization of mAb production technology: the bioprocessing industry at a crossroads," mAbs, 1(5):443-452.

Krook et al. (Dec. 1998) "Novel peptides binding to the Fc-portion of immunoglobulins obtained from a combinatorial phage display peptide library," Journal of Immunological Methods, 221(1-2):151-157.

Lawrence and PM Colman (Dec. 1993) "Shape complementarity at protein/protein interfaces," Journal of Molecular Biology, 234(4):946-950.

Lee et al. (Jul. 2011) "Complete genome sequence of hyperthermophilic Pyrococcus sp. strain NA2, isolated from a deep-sea hydrothermal vent area," Journal of Bacteriology, 193(14):3666-3667.

Lund et al. (Feb. 2012) "Novel peptide ligand with high binding capacity for antibody purification," Journal of Chromatography A, 1225:158-167.

Martin et al. (Apr. 2001) "Crystal structure at 2.8 A of an FcRn/ heterodimeric Fc complex: mechanism of pH-dependent binding," Molecular Cell, 7(4):867-877.

Murtaugh et al. (Sep. 2011) "A combinatorial histidine scanning library approach to engineer highly pH-dependent protein switches," Protein Science, 20(9):1619-1631.

Schneidman-Duhovny et al. (Jul. 2005) "PatchDock and SymmDock: servers for rigid and symmetric docking," Nucleic Acids Research, 33(Web Server Issue):W363-367.

Whitehead et al. (May 2012) "Optimization of affinity, specificity and function of designed influenza inhibitors using deep sequencing," Nature Biotechnology, 30(6):543-548.

Winn et al. (Apr. 2011) "Overview of the CCP4 suite and current developments," Acta Crystallographica Section D, Biological Crystallography, 67(Pt. 4):235-242.

Yi et al. (2012) "IgG purification using affinity filtration with sulfamethazine-affinity carriers," Preparative Biochemistry and Biotechnology, 42(6):598-610; retrieved Aug. 2015.

\* cited by examiner

Figure 3A

| | 1 | 10 | 20 | 30 | 39 |
|---|---|---|---|---|---|
| 1. Fc24 translation | S A T A E D A | K G E | V L | D A | G P E E Q Q A |
| 2. genIII-S4-12-... | S T A D A | K G E | V L | D A | G P E Q Q S |
| 3. genIII-S4-15-... | S T A D A | K G E | V L | D A | G P E Q Q S |
| 4. genIII-S4-4-u... | S T A D A | K G E | V L | D A | G P E Q Q S |
| 5. genIII-S4-16-... | S T A D A | K G E | V L | D A | G P E Q Q S |
| 6. genIII-S4-11-... | S T A A D A | K G E | V L | D A | G P E Q Q S |
| 7. genIII-S4-7-u... | A T A D A | K G E | V L | D A | G P E Q Q S |
| 8. genIII-S4-5-u... | S T A D A | K G E | V L | D A | G P E Q Q A |
| 9. genIII-S4-6-u... | S T A D A | K G E | V L | D A | G P E Q Q S |
| 10. genIII-S4-10... | S T A D A | K G E | V L | D A | G P E Q Q S |
| 11. genIII-S4-2-... | S T A D A | K G E | V L | D A | G P E Q Q S |
| 12. genIII-S4-13... | S T A D A | K G E | V L | D A | G P E Q Q S |
| 13. genIII-S4-8-... | S T A D A | K G E | V L | D A | G P E Q Q S |
| 14. genIII-S4-3-... | S T A D A | K G E | V L | D A | G P E Q Q S |
| 15. genIII-S4-9-... | S T A D A | K G E | V L | D A | G P E Q Q S |

Figure 3B

| | 1 | 10 | 20 | 30 | 39 |
|---|---|---|---|---|---|
| 1. Fc24 translation | S A T A E D A | K G E | V L | D A | G P E E Q Q A |
| 2. genIII-S4-39-u... | S T T A D A | G E | V L | D A | G P G E Q Q S |
| 3. genIII-S4-38-u... | S T A D A | G E | V L | D A | G P E Q Q S |
| 4. genIII-S4-44-u... | S T A D A | G E | V L | D A | G P S E Q Q S |
| 5. genIII-S4-42-u... | S T A T D A | G E | V L | D A | G P S E Q Q S |
| 6. genIII-S4-40-u... | S T A D A | G E | V L | D A | G P E Q Q S |
| 7. genIII-S4-35-u... | S T A D A | G E | V L | D A | G P P E Q Q S |
| 8. genIII-S4-46-u... | A T A D A | G E | V L | D A | G P E Q Q S |
| 9. genIII-S4-37-u... | S T A D A | G E | V L | D A | G P E Q Q S |
| 10. genIII-S4-36-... | S T A A D A | G E | V L | D A | G P A E Q Q S |
| 11. genIII-S4-45-... | S T A D A | G E | V L | D A | G P T E E Q Q S |
| 12. genIII-S4-48-... | S T A D A | G E | V L | D A | G P T E E Q Q S |
| 13. genIII-S4-47-... | S T A D A | G E | V L | D A | G P T E Q Q S |
| 14. genIII-S4-43-... | S T A D A | G E | V L | D A | G P E Q Q S |

Figure 4

SEQUENCE LISTING

```
<160> NUMBER OF SEQ ID NOS: 213

<210> SEQ ID NO 1
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: X is any amino acid
<220> FEATURE:
<221> NAME/KEY: MISC_FEATURE
<222> LOCATION: (6)..(14)
<223> OTHER INFORMATION: X is any amino acid
<220> FEATURE:
<221> NAME/KEY: MISC_FEATURE
<222> LOCATION: (15)..(64)
<223> OTHER INFORMATION: X is any amino acid
<220> FEATURE:
<221> NAME/KEY: MISC_FEATURE
<222> LOCATION: (32)..(64)
<223> OTHER INFORMATION: X is optinally absent
<220> FEATURE:
<221> NAME/KEY: MISC_FEATURE
<222> LOCATION: (65)..(68)
<223> OTHER INFORMATION: X is any amino acid
<220> FEATURE:
<221> NAME/KEY: MISC_FEATURE
<222> LOCATION: (70)..(71)
<223> OTHER INFORMATION: X is any amino acid
<220> FEATURE:
<221> NAME/KEY: MISC_FEATURE
<222> LOCATION: (74)..(77)
<223> OTHER INFORMATION: X is any amino acid

<400> SEQUENCE: 1

Xaa Xaa Xaa Xaa Ser Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Gln Xaa Xaa Phe Tyr Xaa Xaa Xaa Xaa
 65                  70                  75

<210> SEQ ID NO 2
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: X is any amino acid
<220> FEATURE:
<221> NAME/KEY: MISC_FEATURE
<222> LOCATION: (6)..(14)
<223> OTHER INFORMATION: X is any amino acid

<400> SEQUENCE: 2

Xaa Xaa Xaa Xaa Ser Xaa Xaa Xaa Xaa Xaa Xaa Xaa Xaa Xaa
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: X is any amino acid
<220> FEATURE:
<221> NAME/KEY: MISC_FEATURE
<222> LOCATION: (6)..(7)
<223> OTHER INFORMATION: X is any amino acid
<220> FEATURE:
<221> NAME/KEY: MISC_FEATURE
<222> LOCATION: (10)..(13)
<223> OTHER INFORMATION: X is any amino acid

<400> SEQUENCE: 3

Xaa Xaa Xaa Xaa Gln Xaa Xaa Phe Tyr Xaa Xaa Xaa Xaa
 1               5                  10

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (5)..(9)
<223> OTHER INFORMATION: X is any amino acid

<400> SEQUENCE: 4

Arg Xaa Xaa Val Xaa Xaa Xaa Xaa Xaa
 1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (6)..(6)
<223> OTHER INFORMATION: X is A or F
<220> FEATURE:
<221> NAME/KEY: MISC_FEATURE
<222> LOCATION: (7)..(7)
<223> OTHER INFORMATION: X is L, R, or K
<220> FEATURE:
<221> NAME/KEY: MISC_FEATURE
<222> LOCATION: (8)..(8)
<223> OTHER INFORMATION: X is L or K

<400> SEQUENCE: 5

Arg Thr Ala Xaa Asp Xaa Xaa Xaa His
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is T, S, R, M, P, W, E or V
<220> FEATURE:
<221> NAME/KEY: MISC_FEATURE
<222> LOCATION: (2)..(2)
<223> OTHER INFORMATION: X is M or F
<220> FEATURE:
<221> NAME/KEY: MISC_FEATURE
<222> LOCATION: (3)..(3)
<223> OTHER INFORMATION: X is E, M, k, l, or V

<400> SEQUENCE: 6

Xaa Xaa Xaa Gln
1

<210> SEQ ID NO 7
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is L or W
<220> FEATURE:
<221> NAME/KEY: MISC_FEATURE
<222> LOCATION: (4)..(4)
<223> OTHER INFORMATION: X is R or K

<400> SEQUENCE: 7

Met Xaa Xaa Xaa
1
```

<210> SEQ ID NO 8
<211> LENGTH: 277
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(200)
<223> OTHER INFORMATION: X is any amino acid
<220> FEATURE:
<221> NAME/KEY: MISC_FEATURE
<222> LOCATION: (101)..(200)
<223> OTHER INFORMATION: X is optionally absent
<220> FEATURE:
<221> NAME/KEY: MISC_FEATURE
<222> LOCATION: (201)..(204)
<223> OTHER INFORMATION: X is any amino acid
<220> FEATURE:
<221> NAME/KEY: MISC_FEATURE
<222> LOCATION: (206)..(268)
<223> OTHER INFORMATION: X is any amino acid
<220> FEATURE:
<221> NAME/KEY: MISC_FEATURE
<222> LOCATION: (232)..(264)
<223> OTHER INFORMATION: X is optionally absent
<220> FEATURE:
<221> NAME/KEY: MISC_FEATURE
<222> LOCATION: (270)..(271)
<223> OTHER INFORMATION: X is any amino acid
<220> FEATURE:
<221> NAME/KEY: MISC_FEATURE
<222> LOCATION: (274)..(277)
<223> OTHER INFORMATION: X is any amino acid

<400> SEQUENCE: 8

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Ser Xaa Xaa Xaa
        195                 200                 205

Xaa Xaa Xaa Xaa Xaa Xaa Xaa Xaa Xaa Xaa Xaa Xaa Xaa Xaa Xaa

```
                     210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Gln Xaa Xaa Phe
            260                 265                 270

Tyr Xaa Xaa Xaa Xaa
        275

<210> SEQ ID NO 9
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: X is any amino acid
<220> FEATURE:
<221> NAME/KEY: MISC_FEATURE
<222> LOCATION: (7)..(15)
<223> OTHER INFORMATION: X is any amino acid

<400> SEQUENCE: 9

Xaa Xaa Xaa Xaa Ser Arg Xaa Xaa Xaa Xaa Xaa Xaa Xaa Xaa
1               5                   10

<210> SEQ ID NO 10
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 10

Glu Tyr Xaa Val
1

<210> SEQ ID NO 11
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is R, A, or T
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (7)..(7)
<223> OTHER INFORMATION: X is L, R, K, or F
<220> FEATURE:
<221> NAME/KEY: MISC_FEATURE
<222> LOCATION: (8)..(8)
<223> OTHER INFORMATION: X is K or L
<220> FEATURE:
<221> NAME/KEY: MISC_FEATURE
<222> LOCATION: (9)..(9)
<223> OTHER INFORMATION: X is H or L
```

<400> SEQUENCE: 11

Xaa Thr Ala Xaa Asp Ala Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (7)..(7)
<223> OTHER INFORMATION: X is R or K

<400> SEQUENCE: 12

Arg Thr Ala Xaa Asp Ala Xaa Lys His
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Arg Thr Ala Val Asp Ala Leu Lys His
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Glu Tyr Cys Val Ser Ala Thr Ala Glu Asp Ala Leu Lys His
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Glu Tyr Cys Val Ser Arg Thr Ala Val Asp Ala Lys Lys His
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

Glu Tyr Ala Val Ser Arg Thr Ala Val Asp Ala Leu Lys His
1               5                   10

```
<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Glu Tyr Cys Val Ser Arg Thr Ala Val Asp Ala Leu Lys His
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C
<220> FEATURE:
<221> NAME/KEY: MISC_FEATURE
<222> LOCATION: (9)..(9)
<223> OTHER INFORMATION: X is E, V, L, M, A, I, or T

<400> SEQUENCE: 18

Glu Tyr Xaa Val Ser Arg Thr Ala Xaa Asp Ala Leu Lys His
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C
<220> FEATURE:
<221> NAME/KEY: MISC_FEATURE
<222> LOCATION: (9)..(9)
<223> OTHER INFORMATION: X is E, V, L, R, M, or A

<400> SEQUENCE: 19

Glu Tyr Xaa Val Ser Arg Thr Ala Xaa Asp Ala Leu Lys His
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C
<220> FEATURE:
<221> NAME/KEY: MISC_FEATURE
<222> LOCATION: (9)..(9)
<223> OTHER INFORMATION: X is E, V, M, A, I or T

<400> SEQUENCE: 20

Glu Tyr Xaa Val Ser Arg Thr Ala Xaa Asp Ala Leu Lys His
1               5                   10

<210> SEQ ID NO 21
<211> LENGTH: 14
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 21

Glu Tyr Xaa Val Ser Arg Thr Ala Val Asp Ala Leu Lys His
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C
<220> FEATURE:
<221> NAME/KEY: MISC_FEATURE
<222> LOCATION: (9)..(9)
<223> OTHER INFORMATION: X is V or M

<400> SEQUENCE: 22

Glu Tyr Xaa Val Ser Arg Thr Ala Xaa Asp Ala Leu Lys His
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 23

Glu Tyr Xaa Val Ser Arg Thr Ala Met Asp Ala Leu Lys His
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 24

Glu Tyr Xaa Val Ser Arg Thr Ala Ala Asp Ala Leu Lys His
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
```

<223> OTHER INFORMATION: X is A or C

<400> SEQUENCE: 25

Glu Tyr Xaa Val Ser Arg Thr Ala Met Asp Ala Leu Lys His
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 26

Glu Tyr Xaa Val Ser Arg Thr Ala Leu Asp Ala Leu Lys His
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 27

Glu Tyr Xaa Val Ser Arg Thr Ala Ile Asp Ala Leu Lys His
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 28

Glu Tyr Xaa Val Ser Arg Thr Ala Thr Asp Ala Leu Lys His
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 29

Glu Tyr Xaa Val Ser Arg Thr Ala Val Asp Ala Leu Lys His
1               5                   10

<210> SEQ ID NO 30
<211> LENGTH: 14
<212> TYPE: PRT

<213> ORGANISM: Artificial Sequence
<220> FEATURE:
<223> OTHER INFORMATION: Synthetic

<400> SEQUENCE: 30

Glu Tyr Ala Val Ser Arg Thr Ala Met Asp Ala Leu Lys His
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Glu Tyr Ala Val Ser Arg Thr Ala Ala Asp Ala Leu Lys His
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Glu Tyr Ala Val Ser Arg Thr Ala Met Asp Ala Leu Lys His
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Glu Tyr Ala Val Ser Arg Thr Ala Leu Asp Ala Leu Lys His
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Glu Tyr Ala Val Ser Arg Thr Ala Ile Asp Ala Leu Lys His
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Glu Tyr Ala Val Ser Arg Thr Ala Thr Asp Ala Leu Lys His
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Glu Tyr Cys Val Ser Arg Thr Ala Met Asp Ala Leu Lys His
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic

<400> SEQUENCE: 37

Glu Tyr Cys Val Ser Arg Thr Ala Ala Asp Ala Leu Lys His
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic

<400> SEQUENCE: 38

Glu Tyr Cys Val Ser Arg Thr Ala Met Asp Ala Leu Lys His
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic

<400> SEQUENCE: 39

Glu Tyr Cys Val Ser Arg Thr Ala Leu Asp Ala Leu Lys His
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic

<400> SEQUENCE: 40

Glu Tyr Cys Val Ser Arg Thr Ala Ile Asp Ala Leu Lys His
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Glu Tyr Cys Val Ser Arg Thr Ala Thr Asp Ala Leu Lys His
1               5                   10

<210> SEQ ID NO 42
<211> LENGTH: 4
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (1)..(1)
<223> OTHER INFORMATION: X is T, S, R, M, P, W, V, or E
<220> FEATURE:
<221> NAME/KEY: MISC_FEATURE
<222> LOCATION: (2)..(2)
<223> OTHER INFORMATION: X is M or F
<220> FEATURE:
<221> NAME/KEY: MISC_FEATURE
<222> LOCATION: (3)..(3)
<223> OTHER INFORMATION: X is E, M, K, L, or V

<400> SEQUENCE: 42

Xaa Xaa Xaa Gln
1

<210> SEQ ID NO 43
<211> LENGTH: 4
<212> TYPE: PRT
<213> ORGANISM: Artificial Sequence
<220> FEATURE:
<223> OTHER INFORMATION: Synthetic

<400> SEQUENCE: 43

Thr Phe Glu Gln
1

<210> SEQ ID NO 44
<211> LENGTH: 4
<212> TYPE: PRT
<213> ORGANISM: Artificial Sequence
<220> FEATURE:
<223> OTHER INFORMATION: Synthetic

<400> SEQUENCE: 44

Met Ser Leu Lys
1

<210> SEQ ID NO 45
<211> LENGTH: 4
<212> TYPE: PRT
<213> ORGANISM: Artificial Sequence
<220> FEATURE:
<223> OTHER INFORMATION: Synthetic

<400> SEQUENCE: 45

Met Thr Leu Lys
1

<210> SEQ ID NO 46
<211> LENGTH: 4
<212> TYPE: PRT
<213> ORGANISM: Artificial Sequence
<220> FEATURE:
<223> OTHER INFORMATION: Synthetic

<400> SEQUENCE: 46

Met Lys Leu Arg
1

<210> SEQ ID NO 47
<211> LENGTH: 13
<212> TYPE: PRT
<213> ORGANISM: Artificial Sequence
<220> FEATURE:
<223> OTHER INFORMATION: Synthetic
```

```
<400> SEQUENCE: 47

Glu Met Glu Gln Gln Ala Phe Phe Tyr Met Lys Leu Arg
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic

<400> SEQUENCE: 48

Glu Met Glu Gln Gln Ala Leu Phe Tyr Met Lys Leu Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic

<400> SEQUENCE: 49

Thr Phe Glu Gln Gln Ser Phe Phe Tyr Met Ser Leu Lys
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(9)
<223> OTHER INFORMATION: X is any amino acid

<400> SEQUENCE: 50

Arg Xaa Xaa Xaa Xaa Xaa Xaa Xaa Xaa
1               5

<210> SEQ ID NO 51
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: X is any amino acid
<220> FEATURE:
<221> NAME/KEY: MISC_FEATURE
<222> LOCATION: (6)..(6)
<223> OTHER INFORMATION: X is S or A
<220> FEATURE:
<221> NAME/KEY: MISC_FEATURE
<222> LOCATION: (7)..(7)
<223> OTHER INFORMATION: X is F or L
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (13)..(13)
<223> OTHER INFORMATION: X is K or R

<400> SEQUENCE: 51

Xaa Xaa Glu Gln Gln Xaa Xaa Phe Tyr Met Xaa Leu Xaa
```

<210> SEQ ID NO 52
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is G, R, S, M, P, W, V, T, or R
<220> FEATURE:
<221> NAME/KEY: MISC_FEATURE
<222> LOCATION: (2)..(2)
<223> OTHER INFORMATION: X is M, L, I, A, E or F
<220> FEATURE:
<221> NAME/KEY: MISC_FEATURE
<222> LOCATION: (6)..(6)
<223> OTHER INFORMATION: X is S or A
<220> FEATURE:
<221> NAME/KEY: MISC_FEATURE
<222> LOCATION: (7)..(7)
<223> OTHER INFORMATION: X is F or L
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (13)..(13)
<223> OTHER INFORMATION: X is K or R

<400> SEQUENCE: 52

Xaa Xaa Glu Gln Gln Xaa Xaa Phe Tyr Met Xaa Leu Xaa
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is V, H, K or W
<220> FEATURE:
<221> NAME/KEY: MISC_FEATURE
<222> LOCATION: (2)..(2)
<223> OTHER INFORMATION: X is M, W, I, L, or H
<220> FEATURE:
<221> NAME/KEY: MISC_FEATURE
<222> LOCATION: (6)..(6)
<223> OTHER INFORMATION: X is S or A
<220> FEATURE:
<221> NAME/KEY: MISC_FEATURE
<222> LOCATION: (7)..(7)
<223> OTHER INFORMATION: X is F or L
<220> FEATURE:
<221> NAME/KEY: MISC_FEATURE
<222> LOCATION: (11)..(11)
<223> OTHER INFORMATION: X is any amino acid
<220> FEATURE:
<221> NAME/KEY: MISC_FEATURE
<222> LOCATION: (13)..(13)
<223> OTHER INFORMATION: X is K or R

<400> SEQUENCE: 53

Xaa Xaa Glu Gln Gln Xaa Xaa Phe Tyr Met Xaa Leu Xaa
1               5                   10

<210> SEQ ID NO 54
<211> LENGTH: 13

```
<212> TYPE: PRT
<213> ORGANISM: Artificial Sequence
<220> FEATURE:
<223> OTHER INFORMATION: Synthetic

<400> SEQUENCE: 54

Glu Met Glu Gln Gln Ala Leu Phe Tyr Met Lys Leu Lys
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55

Val Trp Glu Gln Gln Ser Phe Phe Tyr Met Val Leu Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

His Trp Glu Gln Gln Ser Phe Phe Tyr Met Leu Leu Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic

<400> SEQUENCE: 57

His Met Glu Gln Gln Ser Phe Phe Tyr Met Met Leu Lys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic

<400> SEQUENCE: 58

Lys Ile Glu Gln Gln Ser Phe Phe Tyr Met Met Leu Lys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic

<400> SEQUENCE: 59

Trp Leu Glu Gln Gln Ser Phe Phe Tyr Met Ala Leu Lys
1               5                   10

<210> SEQ ID NO 60
<211> LENGTH: 13
<212> TYPE: PRT
```

```
<213> ORGANISM: Artificial Sequence
<220> FEATURE:
<223> OTHER INFORMATION: Synthetic

<400> SEQUENCE: 60

Trp Leu Glu Gln Gln Ser Phe Phe Tyr Met Gln Leu Lys
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic

<400> SEQUENCE: 61

Trp Leu Glu Gln Gln Ala Phe Phe Tyr Met Glu Leu Lys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic

<400> SEQUENCE: 62

Trp Leu Glu Gln Gln Ser Phe Phe Tyr Met Lys Leu Lys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic

<400> SEQUENCE: 63

Phe Leu Glu Gln Gln Ser Phe Phe Tyr Met Arg Leu Lys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic

<400> SEQUENCE: 64

Trp His Glu Gln Gln Ser Phe Phe Tyr Met Met Leu Lys
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic

<400> SEQUENCE: 65

Trp His Glu Gln Gln Ser Phe Phe Tyr Met Arg Leu Lys
1               5                   10

<210> SEQ ID NO 66
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 66

Glu Met Glu Gln Gln Ala Leu Phe Tyr Met Lys Leu Lys
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic

<400> SEQUENCE: 67

Gly Met Glu Gln Gln Ser Phe Phe Tyr Met Ile Leu Lys
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic

<400> SEQUENCE: 68

Arg Leu Glu Gln Gln Ser Phe Phe Tyr Met Thr Leu Lys
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic

<400> SEQUENCE: 69

Ser Leu Glu Gln Gln Ser Phe Phe Tyr Met Asn Leu Lys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic

<400> SEQUENCE: 70

Met Ile Glu Gln Gln Ser Phe Phe Tyr Met Arg Leu Lys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic

<400> SEQUENCE: 71

Pro Ile Glu Gln Gln Ser Phe Phe Tyr Met His Leu Lys
1               5                   10

<210> SEQ ID NO 72
<211> LENGTH: 13
<212> TYPE: PRT
<213> ORGANISM: Artificial Sequence
<220> FEATURE:
```

<223> OTHER INFORMATION: Synthetic

<400> SEQUENCE: 72

Trp Leu Glu Gln Gln Ser Phe Phe Tyr Met His Leu Lys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic

<400> SEQUENCE: 73

Val Leu Glu Gln Gln Ser Phe Phe Tyr Met Asp Leu Lys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic

<400> SEQUENCE: 74

Trp Ala Glu Gln Gln Ser Phe Phe Tyr Met Gly Leu Lys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic

<400> SEQUENCE: 75

Thr Glu Glu Gln Gln Ser Phe Phe Tyr Met Thr Leu Lys
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic

<400> SEQUENCE: 76

Thr Phe Glu Gln Gln Ser Phe Phe Tyr Met Ser Leu Lys
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic

<400> SEQUENCE: 77

Arg Leu Glu Gln Gln Ser Phe Phe Tyr Met Ser Leu Lys
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic

```
<400> SEQUENCE: 78

Glu Arg Glu Gln Gln Ser Phe Phe Tyr Met Gly Leu Lys
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic

<400> SEQUENCE: 79

Glu Arg Glu Gln Gln Ser Phe Phe Tyr Met Gly Leu Lys
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic

<400> SEQUENCE: 80

His Met Lys Gln Gln Ser Phe Phe Tyr Met Ser Leu Arg
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic

<400> SEQUENCE: 81

His Trp Val Gln Gln Ser Phe Phe Tyr Met Gly Leu Lys
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic

<400> SEQUENCE: 82

Asp Trp Val Gln Gln Ser Met Phe Tyr Met Glu Leu Lys
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic

<400> SEQUENCE: 83

Asp Trp Val Gln Gln Ser Leu Phe Tyr Met Asn Leu Lys
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic
```

```
<400> SEQUENCE: 84

Glu Trp Val Gln Gln Ser Leu Phe Tyr Met Gly Leu Lys
1               5                   10

<210> SEQ ID NO 85
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is F or V
<220> FEATURE:
<221> NAME/KEY: MISC_FEATURE
<222> LOCATION: (3)..(3)
<223> OTHER INFORMATION: X is E or D
<220> FEATURE:
<221> NAME/KEY: MISC_FEATURE
<222> LOCATION: (4)..(4)
<223> OTHER INFORMATION: X is V or G
<220> FEATURE:
<221> NAME/KEY: MISC_FEATURE
<222> LOCATION: (5)..(5)
<223> OTHER INFORMATION: X is Y or C
<220> FEATURE:
<221> NAME/KEY: MISC_FEATURE
<222> LOCATION: (7)..(7)
<223> OTHER INFORMATION: X is L or F
<220> FEATURE:
<221> NAME/KEY: MISC_FEATURE
<222> LOCATION: (9)..(9)
<223> OTHER INFORMATION: X is D, E or N
<220> FEATURE:
<221> NAME/KEY: MISC_FEATURE
<222> LOCATION: (14)..(14)
<223> OTHER INFORMATION: X is I, V or F

<400> SEQUENCE: 85

Gly Xaa Xaa Xaa Xaa Leu Xaa Arg Xaa Ala Val Lys Gly Xaa Lys Pro
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: X is I, V, or F

<400> SEQUENCE: 86

Gly Phe Glu Val Tyr Leu Leu Arg Asp Ala Val Lys Gly Xaa Lys Pro
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Synthetic

<400> SEQUENCE: 87

Gly Phe Glu Val Tyr Leu Leu Arg Asp Ala Val Lys Gly Ile Lys Pro
1               5                   10                  15

<210> SEQ ID NO 88
<211> LENGTH: 42
```

<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A and C

<400> SEQUENCE: 88

Glu Tyr Xaa Ser Ala Thr Ala Glu Asp Ala Leu Lys His Gly Phe Glu
1               5                   10                  15

Val Tyr Leu Leu Arg Asp Ala Val Lys Gly Ile Lys Pro Glu Met Glu
            20                  25                  30

Gln Gln Ala Leu Phe Tyr Met Lys Leu Arg
        35                  40

<210> SEQ ID NO 89
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 89

Glu Tyr Xaa Ser Arg Thr Ala Arg Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ser Phe Phe Tyr Met Lys Leu Lys
        35                  40

<210> SEQ ID NO 90
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 90

Glu Tyr Xaa Ser Arg Thr Ala Val Asp Ala Leu Lys His Gly Phe Glu
1               5                   10                  15

Val Tyr Leu Leu Arg Asp Ala Val Lys Gly Ile Lys Pro Val Trp Glu
            20                  25                  30

Gln Gln Ser Phe Phe Tyr Met Val Leu Lys
        35                  40

<210> SEQ ID NO 91
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 91

Glu Tyr Xaa Ser Arg Thr Ala Ala Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ser Phe Phe Tyr Met Ala Leu Lys
        35                  40

<210> SEQ ID NO 92
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 92

Glu Tyr Xaa Ser Arg Thr Ala Val Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ala Phe Phe Tyr Met Glu Leu Lys
        35                  40

<210> SEQ ID NO 93
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 93

Glu Tyr Xaa Ser Arg Thr Ala Met Asp Ala Leu Lys His Gly Phe Glu
1               5                   10                  15

Val Tyr Leu Leu Arg Asp Ala Val Lys Gly Ile Lys Pro Phe Leu Glu
            20                  25                  30

Gln Gln Ser Phe Phe Tyr Met Arg Leu Lys
        35                  40

<210> SEQ ID NO 94
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 94

Glu Tyr Xaa Ser His Thr Ala Met Asp Ala Leu Lys His Gly Phe Glu
1               5                   10                  15

Val Tyr Leu Leu Arg Asp Ala Val Lys Gly Ile Lys Pro His Trp Glu
            20                  25                  30

Gln Gln Ser Phe Phe Tyr Met Leu Leu Lys
        35                  40

<210> SEQ ID NO 95
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 95

Glu Tyr Xaa Ser His Thr Ala Val Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ser Phe Phe Tyr Met Arg Leu Lys
        35                  40

<210> SEQ ID NO 96
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 96

Glu Tyr Xaa Ser His Thr Ala Val Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ser Phe Phe Tyr Met Arg Leu Lys
        35                  40

<210> SEQ ID NO 97
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 97

Glu Tyr Xaa Ser Trp Thr Ala Val Asp Ala Leu Lys His Gly Phe Glu
1               5                   10                  15

Val Tyr Leu Leu Arg Asp Ala Val Lys Gly Ile Lys Pro His Met Glu
            20                  25                  30

Gln

<210> SEQ ID NO 98
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C -continued

<400> SEQUENCE: 98

Glu Tyr Xaa Ala Phe Thr Ala Val Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ser Phe Phe Tyr Met Gln Leu Lys
        35                  40

<210> SEQ ID NO 99
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 99

Glu Tyr Xaa Ser Val Thr Ala Leu Asp Ala Leu Lys His Gly Phe Glu
1               5                   10                  15

Val Tyr Leu Leu Arg Asp Ala Val Lys Gly
            20                  25

<210> SEQ ID NO 100
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 100

Glu Tyr Xaa Ser Leu Thr Ala Val Asp Ala Leu Lys His Gly Phe Glu
1               5                   10                  15

Val Tyr Leu Leu Arg Asp Ala Val Lys Gly Ile Lys Pro Lys Ile Glu
            20                  25                  30

Gln Gln Ser Phe Phe Tyr Met Met Leu Lys
        35                  40

<210> SEQ ID NO 101
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 101

Glu Tyr Xaa Ser Leu Thr Ala Val Asp Ala Leu Lys His Gly Phe Glu
1               5                   10                  15

Val Tyr Leu Leu Arg Asp Ala Val Lys Gly Ile Lys Pro Trp His Glu
            20                  25                  30

Gln Gln Ser Phe Phe Tyr Met Leu Leu Lys
        35                  40

```
<210> SEQ ID NO 102
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 102

Glu Tyr Xaa Ser Leu Thr Ala Val Asp Ala Leu Lys His Gly Phe Glu
1               5                   10                  15

Val Tyr Leu Leu Arg Asp Ala Val Lys Gly Ile Lys Pro Trp His Glu
            20                  25                  30

Gln Gln Ser Phe Phe Tyr Met Leu Leu Lys
        35                  40

<210> SEQ ID NO 103
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 103

Glu Tyr Xaa Ser Ala Thr Ala Glu Asp Ala Leu Lys His Gly Phe Glu
1               5                   10                  15

Val Tyr Leu Leu Arg Asp Ala Val Lys Gly Ile Lys Pro Glu Met Glu
            20                  25                  30

Gln Gln Ala Leu Phe Tyr Met Lys Leu Arg
        35                  40

<210> SEQ ID NO 104
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 104

Glu Tyr Xaa Ser Arg Thr Ala Val Asp Ala Leu Lys His Gly Phe Glu
1               5                   10                  15

Val Tyr Leu Leu Arg Asp Ala Val Lys Gly Ile Lys Pro Thr Phe Glu
            20                  25                  30

Gln Gln Ser Phe Phe Tyr Met Ser Leu Lys
        35                  40

<210> SEQ ID NO 105
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C
```

<400> SEQUENCE: 105

Glu Tyr Xaa Ser Arg Thr Ala Val Asp Ala Leu Lys His Gly Phe Glu
1               5                   10                  15

Val Tyr Leu Leu Arg Asp Ala Val Lys Gly Ile Lys Pro Val Leu Glu
            20                  25                  30

Gln Gln Ser Phe Phe Tyr Met Asp Leu Lys
        35                  40

<210> SEQ ID NO 106
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 106

Glu Tyr Xaa Ser Arg Thr Ala Met Asp Ala Leu Lys His Gly Phe Glu
1               5                   10                  15

Val Tyr Leu Leu Arg Asp Ala Val Lys Gly Ile Lys Pro Arg Leu Glu
            20                  25                  30

Gln Gln Ser Phe Phe Tyr Met Thr Leu Lys
        35                  40

<210> SEQ ID NO 107
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 107

Glu Tyr Xaa Ser Arg Thr Ala Val Asp Ala Leu Lys His Gly Phe Glu
1               5                   10                  15

Val Tyr Leu Leu Arg Asp Ala Val Lys Gly Ile Lys Pro Arg Leu Glu
            20                  25                  30

Gln Gln Ser Phe Phe Tyr Met Ser Leu Lys
        35                  40

<210> SEQ ID NO 108
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 108

Glu Tyr Xaa Ser Arg Thr Ala Met Asp Ala Leu Lys His Gly Phe Glu
1               5                   10                  15

Val Tyr Leu Leu Arg Asp Ala Val Lys Gly Ile Lys Pro Thr Glu Glu
            20                  25                  30

Gln Gln Ser Phe Phe Tyr Met Thr Leu Lys

```
                35                  40

<210> SEQ ID NO 109
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 109

Glu Tyr Xaa Ser Arg Thr Ala Met Asp Ala Leu Lys His Gly Phe Glu
1               5                   10                  15

Val Tyr Leu Leu Arg Asp Ala Val Lys Gly Ile Lys Pro Thr Glu Glu
            20                  25                  30

Gln Gln Ser Phe Phe Tyr Met Thr Leu Lys
        35                  40

<210> SEQ ID NO 110
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 110

Glu Tyr Xaa Ser Lys Thr Ala Thr Asp Ala Leu Lys His Gly Phe Glu
1               5                   10                  15

Val Tyr Leu Leu Arg Asp Ala Val Lys Gly Ile Lys Pro Ser Leu Glu
            20                  25                  30

Gln Gln Ser Phe Phe Tyr Met Arg Leu Lys
        35                  40

<210> SEQ ID NO 111
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 111

Glu Tyr Xaa Ser Thr Thr Ala Ile Asp Ala Leu Lys His Gly Phe Glu
1               5                   10                  15

Val Tyr Leu Leu Arg Asp Ala Val Lys Gly Ile Lys Pro Gly Met Glu
            20                  25                  30

Gln Gln Ser Phe Phe Tyr Met Ile Leu Lys
        35                  40

<210> SEQ ID NO 112
<211> LENGTH: 42
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (3)..(3)
<223> OTHER INFORMATION: X is A or C

<400> SEQUENCE: 112

Glu Tyr Xaa Ser Leu Thr Ala Val Asp Ala Leu Lys His Gly Phe Glu
1               5                   10                  15

Val Tyr Leu Leu Arg Asp Ala Val Lys Gly Ile Lys Pro Met Ile Glu
            20                  25                  30

Gln Gln Ser Phe Phe Tyr Met Arg Leu Lys
        35                  40

<210> SEQ ID NO 113
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 113

Glu Tyr Xaa Ser Phe Thr Ala Ala Asp Ala Leu Lys His Gly Phe Glu
1               5                   10                  15

Val Tyr Leu Leu Arg Asp Ala Val Lys Gly Ile Lys Pro Trp Ala Glu
            20                  25                  30

Gln Gln Ser Phe Phe Tyr Met Gly Leu Lys
        35                  40

<210> SEQ ID NO 114
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 114

Glu Tyr Xaa Ser Trp Thr Ala Met Asp Ala Leu Lys His Gly Phe Glu
1               5                   10                  15

Val Tyr Leu Leu Arg Asp Ala Val Lys Gly Ile Lys Pro Pro Ile Glu
            20                  25                  30

Gln Gln Ser Phe Phe Tyr Met His Leu Lys
        35                  40

<210> SEQ ID NO 115
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 115

Glu Tyr Xaa Ser Met Thr Ala Met Asp Ala Leu Lys His Gly Phe Glu
1               5                   10                  15

Val Tyr Leu Leu Arg Asp Ala Val Lys Gly Ile Lys Pro Ser Leu Glu
```

```
                20                  25                  30

Gln Gln Ser Phe Phe Tyr Met Asn Leu Lys
        35                  40

<210> SEQ ID NO 116
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 116

Glu Tyr Xaa Ala Met Thr Ala Val Asp Ala Leu Lys His Gly Phe Glu
1               5                   10                  15

Val Tyr Leu Leu Arg Asp Ala Val Lys Gly Ile Lys Pro Trp Leu Glu
            20                  25                  30

Gln Gln Ser Phe Phe Tyr Met His Leu Lys
        35                  40

<210> SEQ ID NO 117
<211> LENGTH: 43
<212> TYPE: PRT
<213> ORGANISM: Artificial Sequence
<220> FEATURE:
<223> OTHER INFORMATION: Synthetic

<400> SEQUENCE: 117

Glu Tyr Cys Val Ser Arg Thr Ala Val Asp Ala Leu Lys His Gly Phe
1               5                   10                  15

Glu Val Tyr Leu Leu Arg Asp Ala Val Lys Gly Ile Lys Pro Thr Phe
            20                  25                  30

Glu Gln Gln Ser Phe Phe Tyr Met Ser Leu Lys
        35                  40

<210> SEQ ID NO 118
<211> LENGTH: 43
<212> TYPE: PRT
<213> ORGANISM: Artificial Sequence
<220> FEATURE:
<223> OTHER INFORMATION: Synthetic

<400> SEQUENCE: 118

Glu Tyr Ala Val Ser Arg Thr Ala Val Asp Ala Leu Lys His Gly Phe
1               5                   10                  15

Glu Val Tyr Leu Leu Arg Asp Ala Val Lys Gly Ile Lys Pro Thr Phe
            20                  25                  30

Glu Gln Gln Ser Phe Phe Tyr Met Ser Leu Lys
        35                  40

<210> SEQ ID NO 119
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or C

<400> SEQUENCE: 119
```

```
Glu Tyr Xaa Val Ser Arg Thr Ala Val Asp Ala Leu Lys His Gly Phe
1               5                   10                  15

Glu Val Tyr Leu Leu Arg Asp Ala Val Lys Gly Ile Lys Pro Thr Phe
                20                  25                  30

Glu Gln Gln Ser Phe Phe Tyr Met Ser Leu Lys
            35                  40

<210> SEQ ID NO 120
<211> LENGTH: 177
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: X is any amino acid
<220> FEATURE:
<221> NAME/KEY: MISC_FEATURE
<222> LOCATION: (17)..(19)
<223> OTHER INFORMATION: optionally absent
<220> FEATURE:
<221> NAME/KEY: MISC_FEATURE
<222> LOCATION: (18)..(19)
<223> OTHER INFORMATION: X is any amino acid
<220> FEATURE:
<221> NAME/KEY: MISC_FEATURE
<222> LOCATION: (25)..(25)
<223> OTHER INFORMATION: X is any amino acid
<220> FEATURE:
<221> NAME/KEY: MISC_FEATURE
<222> LOCATION: (31)..(31)
<223> OTHER INFORMATION: X is any amino acid
<220> FEATURE:
<221> NAME/KEY: MISC_FEATURE
<222> LOCATION: (34)..(35)
<223> OTHER INFORMATION: X is any amino acid
<220> FEATURE:
<221> NAME/KEY: MISC_FEATURE
<222> LOCATION: (38)..(38)
<223> OTHER INFORMATION: X is any amino acid
<220> FEATURE:
<221> NAME/KEY: MISC_FEATURE
<222> LOCATION: (41)..(41)
<223> OTHER INFORMATION: X is any amino acid
<220> FEATURE:
<221> NAME/KEY: MISC_FEATURE
<222> LOCATION: (45)..(45)
<223> OTHER INFORMATION: optionally absent
<220> FEATURE:
<221> NAME/KEY: MISC_FEATURE
<222> LOCATION: (46)..(47)
<223> OTHER INFORMATION: X is any amino acid
<220> FEATURE:
<221> NAME/KEY: MISC_FEATURE
<222> LOCATION: (49)..(50)
<223> OTHER INFORMATION: optionally absent
<220> FEATURE:
<221> NAME/KEY: MISC_FEATURE
<222> LOCATION: (49)..(50)
<223> OTHER INFORMATION: X is any amino acid
<220> FEATURE:
<221> NAME/KEY: MISC_FEATURE
<222> LOCATION: (55)..(55)
<223> OTHER INFORMATION: X is any amino acid
<220> FEATURE:
<221> NAME/KEY: MISC_FEATURE
<222> LOCATION: (61)..(62)
<223> OTHER INFORMATION: optionally absent
<220> FEATURE:
<221> NAME/KEY: MISC_FEATURE
<222> LOCATION: (61)..(61)
<223> OTHER INFORMATION: X is any amino acid
<220> FEATURE:
<221> NAME/KEY: MISC_FEATURE
```

```
<222> LOCATION: (70)..(71)
<223> OTHER INFORMATION: X is any amino acid
<220> FEATURE:
<221> NAME/KEY: MISC_FEATURE
<222> LOCATION: (73)..(73)
<223> OTHER INFORMATION: X is any amino acid
<220> FEATURE:
<221> NAME/KEY: MISC_FEATURE
<222> LOCATION: (76)..(99)
<223> OTHER INFORMATION: optionally absent
<220> FEATURE:
<221> NAME/KEY: MISC_FEATURE
<222> LOCATION: (79)..(80)
<223> OTHER INFORMATION: X is any amino acid
<220> FEATURE:
<221> NAME/KEY: MISC_FEATURE
<222> LOCATION: (82)..(89)
<223> OTHER INFORMATION: X is any amino acid
<220> FEATURE:
<221> NAME/KEY: MISC_FEATURE
<222> LOCATION: (98)..(98)
<223> OTHER INFORMATION: X is any amino acid
<220> FEATURE:
<221> NAME/KEY: MISC_FEATURE
<222> LOCATION: (104)..(104)
<223> OTHER INFORMATION: X is any amino acid
<220> FEATURE:
<221> NAME/KEY: MISC_FEATURE
<222> LOCATION: (108)..(109)
<223> OTHER INFORMATION: X is any amino acid
<220> FEATURE:
<221> NAME/KEY: MISC_FEATURE
<222> LOCATION: (114)..(114)
<223> OTHER INFORMATION: X is any amino acid
<220> FEATURE:
<221> NAME/KEY: MISC_FEATURE
<222> LOCATION: (116)..(116)
<223> OTHER INFORMATION: X is any amino acid
<220> FEATURE:
<221> NAME/KEY: MISC_FEATURE
<222> LOCATION: (118)..(123)
<223> OTHER INFORMATION: optionally absent
<220> FEATURE:
<221> NAME/KEY: MISC_FEATURE
<222> LOCATION: (128)..(130)
<223> OTHER INFORMATION: optionally absent
<220> FEATURE:
<221> NAME/KEY: MISC_FEATURE
<222> LOCATION: (128)..(131)
<223> OTHER INFORMATION: X is any amino acid
<220> FEATURE:
<221> NAME/KEY: MISC_FEATURE
<222> LOCATION: (134)..(134)
<223> OTHER INFORMATION: X is any amino acid
<220> FEATURE:
<221> NAME/KEY: MISC_FEATURE
<222> LOCATION: (136)..(136)
<223> OTHER INFORMATION: X is any amino acid
<220> FEATURE:
<221> NAME/KEY: MISC_FEATURE
<222> LOCATION: (138)..(138)
<223> OTHER INFORMATION: X is any amino acid
<220> FEATURE:
<221> NAME/KEY: MISC_FEATURE
<222> LOCATION: (141)..(143)
<223> OTHER INFORMATION: X is any amino acid
<220> FEATURE:
<221> NAME/KEY: MISC_FEATURE
<222> LOCATION: (148)..(148)
<223> OTHER INFORMATION: X is any amino acid
<220> FEATURE:
<221> NAME/KEY: MISC_FEATURE
<222> LOCATION: (152)..(157)
<223> OTHER INFORMATION: optionally absent
<220> FEATURE:
<221> NAME/KEY: MISC_FEATURE
<222> LOCATION: (152)..(155)
<223> OTHER INFORMATION: X is any amino acid
<220> FEATURE:
```

<221> NAME/KEY: MISC_FEATURE
<222> LOCATION: (159)..(161)
<223> OTHER INFORMATION: X is any amino acid
<220> FEATURE:
<221> NAME/KEY: MISC_FEATURE
<222> LOCATION: (173)..(173)
<223> OTHER INFORMATION: X is any amino acid

<400> SEQUENCE: 120

Pro Xaa Xaa Xaa Ala Leu Ile Val Ile Asp Met Gln Asn Asp Phe Val
1               5                   10                  15

Ser Xaa Xaa Pro Gly Gly Pro Leu Xaa Val Pro Gly Gly Glu Xaa Ile
            20                  25                  30

Ile Xaa Xaa Ile Asn Xaa Leu Leu Xaa Ala Ala Arg Phe Xaa Xaa Gly
        35                  40                  45

Xaa Xaa Ile Pro Val Val Xaa Thr Arg Asp Trp His Xaa Gln Pro Glu
    50                  55                  60

Asn His Ile Ser Phe Xaa Xaa Asp Xaa Gly Pro Lys Glx Pro Xaa Xaa
65                  70                  75                  80

Thr Xaa Xaa Xaa Xaa Xaa Xaa Xaa Gly Asp Asp Ser Thr Gln Glu
                85                  90                  95

Gly Xaa Leu Trp Pro Pro His Xaa Val Gln Gly Xaa Xaa Gly Ala Glu
            100                 105                 110

Leu Xaa Pro Xaa Leu Gly Ile Phe Tyr Ala Pro Gln Glu Gly Asp Xaa
        115                 120                 125

Xaa Xaa Xaa Val Ile Xaa Lys Xaa Phe Xaa Thr Asp Xaa Xaa Xaa Tyr
    130                 135                 140

Ser Ala Phe Xaa Gly Thr Asp Xaa Xaa Xaa Xaa Thr Gly Leu Xaa Xaa
145                 150                 155                 160

Xaa Leu Arg Glu Arg Gly Val Asp Thr Val Ile Val Xaa Gly Val Ala
                165                 170                 175

Thr

<210> SEQ ID NO 121
<211> LENGTH: 130
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 121

Met Pro Glu Glu Ala Leu Ile Val Val Asp Met Gln Arg Asp Phe Met
1               5                   10                  15

Pro Gly Gly Ala Leu Pro Val Pro Glu Gly Asp Lys Ile Ile Pro Lys
            20                  25                  30

Val Asn Glu Tyr Ile Arg Lys Phe Lys Glu Lys Gly Ala Leu Ile Val
            35                  40                  45

Ala Thr Arg Asp Trp His Pro Glu Asn His Ile Ser Phe Arg Glu Arg
    50                  55                  60

Gly Gly Pro Trp Pro Arg His Cys Val Gln Asn Thr Pro Gly Ala Glu
65                  70                  75                  80

Phe Val Val Asp Leu Pro Glu Asp Ala Val Ile Ile Ser Lys Ala Thr
                85                  90                  95

Glu Pro Asp Lys Glu Ala Tyr Ser Gly Phe Glu Gly Thr Asp Leu Ala
            100                 105                 110

Lys Ile Leu Arg Gly Asn Gly Val Lys Arg Val Tyr Ile Cys Gly Val
            115                 120                 125

Ala Thr
    130

<210> SEQ ID NO 122
<211> LENGTH: 167
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(8)
<223> OTHER INFORMATION: optionally absent

<400> SEQUENCE: 122

Met Ala His His His His His Val Gly Thr Gly Ser Asn Asp Asp
1               5                   10                  15

Asp Asp Lys Ser Pro Asp Pro Pro Thr Leu Cys Val Thr Val Ser Ser
            20                  25                  30

Thr Thr Asp Val Leu Ile Ile Ala Asp Met Gln Val Asp Phe Leu Ala
        35                  40                  45

Pro Gly Gly Ser Leu His Val Lys Gly Gly Glu Ala Leu Leu Asp Gly
    50                  55                  60

Ile Asn Ala Val Ser Ser Gln Leu Pro Phe Arg Tyr Gln Val Ala Thr
65                  70                  75                  80

Gln Asp Trp His Pro Glu Asn His Cys Ser Phe Val Thr His Gly Gly
                85                  90                  95

Pro Trp Pro Pro His Cys Val Gln Gly Ser Ala Gly Ala Gln Leu His
            100                 105                 110

Ala Gly Leu His Thr Gln Arg Ile Asn Ala Val Ile Arg Lys Gly Val
        115                 120                 125

Thr Gln Gln Ala Asp Ser Tyr Ser Ala Phe Val Glu Asp Asn Gly Val
    130                 135                 140

Ser Thr Gly Leu Ala Gly Leu Leu His Ser Ile Gly Ala Arg Arg Val
145                 150                 155                 160

Phe Val Cys Gly Val Ala Tyr
                165

<210> SEQ ID NO 123
<211> LENGTH: 120
<212> TYPE: PRT
<213> ORGANISM: Artificial Sequence
<220> FEATURE:
<223> OTHER INFORMATION: Synthetic

<400> SEQUENCE: 123

Met Lys Pro Ala Leu Val Val Val Asp Met Val Asn Glu Phe Ile His
1               5                   10                  15

Gly Arg Leu Ala Thr Pro Glu Ala Met Lys Thr Val Gly Pro Ala Arg
            20                  25                  30

Lys Val Ile Glu Thr Phe Arg Arg Ser Gly Leu Pro Val Val Tyr Val
        35                  40                  45

Asn Asp Ser His Tyr Pro Asp Pro Glu Ile Arg Ile Trp Gly Arg
    50                  55                  60

His Ser Met Lys Gly Asp Asp Gly Ser Glu Val Ile Asp Glu Ile Arg
65                  70                  75                  80

-continued

```
Pro Ser Ala Gly Asp Tyr Val Leu Glu Lys His Ala Tyr Ser Gly Phe
                85                  90                  95
Tyr Gly Thr Asn Leu Asp Met Ile Leu Arg Ala Asn Gly Ile Asp Thr
            100                 105                 110
Val Val Leu Ile Gly Leu Asp Ala
        115                 120

<210> SEQ ID NO 124
<211> LENGTH: 177
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: optionally absent

<400> SEQUENCE: 124

Met Gly Ser Ser His His His His His His Ser Ser Gly Glu Asn Leu
1               5                   10                  15
Tyr Phe Gln Gly His Met Lys Met Asn Lys Gln Pro Gln Asn Ser Ala
            20                  25                  30
Leu Val Val Val Asp Val Gln Asn Gly Phe Thr Pro Gly Gly Asn Leu
        35                  40                  45
Ala Val Ala Asp Ala Asp Thr Ile Ile Pro Thr Ile Asn Gln Leu Ala
    50                  55                  60
Gly Cys Phe Glu Asn Val Val Leu Thr Gln Asp Trp His Pro Asp Asn
65                  70                  75                  80
His Ile Ser Phe Ala Ala Asn His Pro Gly Lys Gln Pro Phe Glu Thr
                85                  90                  95
Ile Glu Leu Asp Tyr Gly Ser Gln Val Leu Trp Pro Lys His Cys Ile
            100                 105                 110
Gln Gly Thr His Asp Ala Glu Phe His Pro Asp Leu Asn Ile Pro Thr
        115                 120                 125
Ala Gln Leu Ile Ile Arg Lys Gly Phe His Ala His Ile Asp Ser Tyr
    130                 135                 140
Ser Ala Phe Met Glu Ala Asp His Thr Thr Met Thr Gly Leu Thr Gly
145                 150                 155                 160
Tyr Leu Lys Glu Arg Gly Ile Asp Thr Val Tyr Val Val Gly Ile Ala
                165                 170                 175
Thr

<210> SEQ ID NO 125
<211> LENGTH: 164
<212> TYPE: PRT
<213> ORGANISM: Artificial Sequence
<220> FEATURE:
<223> OTHER INFORMATION: Synthetic

<400> SEQUENCE: 125

Met Lys Thr Leu Ile Val Val Asp Met Gln Asn Asp Phe Ile Ser Pro
1               5                   10                  15
Leu Gly Ser Leu Thr Val Pro Lys Gly Glu Glu Leu Ile Asn Pro Ile
            20                  25                  30
Ser Asp Leu Met Gln Asp Ala Asp Arg Asp Trp His Arg Ile Val Val
        35                  40                  45
Thr Arg Asp Trp His Pro Ser Arg His Ile Ser Phe Ala Lys Asn His
    50                  55                  60
```

```
Lys Asp Lys Glu Pro Tyr Ser Thr Tyr Thr Tyr His Ser Pro Arg Pro
 65                  70                  75                  80

Gly Asp Asp Ser Thr Gln Glu Gly Ile Leu Trp Pro Val His Cys Val
                 85                  90                  95

Lys Asn Thr Trp Gly Ser Gln Leu Val Asp Gln Ile Met Asp Gln Val
            100                 105                 110

Val Thr Lys His Ile Lys Ile Val Asp Lys Gly Phe Leu Thr Asp Arg
        115                 120                 125

Glu Tyr Tyr Ser Ala Phe His Asp Ile Trp Asn Phe His Lys Thr Asp
    130                 135                 140

Met Asn Lys Tyr Leu Glu Lys His His Thr Asp Glu Val Tyr Ile Val
145                 150                 155                 160

Gly Val Ala Leu

<210> SEQ ID NO 126
<211> LENGTH: 153
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: optionally absent

<400> SEQUENCE: 126

Met Gly Ser Ser His His His His His Ser Ser Gly Leu Val Pro
1               5                   10                  15

Arg Gly Ser His Met Thr Lys Ala Leu Ile Ser Ile Asp Tyr Thr Glu
                20                  25                  30

Asp Phe Val Ala Asp Ser Gly Lys Leu Thr Ala Gly Ala Pro Ala Gln
            35                  40                  45

Ala Ile Ser Asp Ala Ile Ser Lys Val Thr Arg Leu Ala Phe Glu Arg
        50                  55                  60

Gly Asp Tyr Ile Phe Phe Thr Ile Asp Ala His Glu Glu Asn Asp Cys
65                  70                  75                  80

Phe His Pro Glu Ser Lys Leu Phe Pro Pro His Asn Leu Ile Gly Thr
                85                  90                  95

Ser Gly Arg Asn Leu Tyr Gly Asp Leu Gly Ile Phe Tyr Gln Glu His
            100                 105                 110

Gly Ser Asp Ser Arg Val Phe Trp Met Asp Lys Arg His Tyr Ser Ala
        115                 120                 125

Phe Ser Gly Thr Asp Leu Asp Ile Arg Leu Arg Glu Arg Arg Val Ser
    130                 135                 140

Thr Val Ile Leu Thr Gly Val Leu Thr
145                 150

<210> SEQ ID NO 127
<211> LENGTH: 123
<212> TYPE: PRT
<213> ORGANISM: Artificial Sequence
<220> FEATURE:
<223> OTHER INFORMATION: Synthetic

<400> SEQUENCE: 127

Gly Met Thr Thr Glu Asn Thr Thr Ala Leu Leu Leu Ile Asp Phe Gln
1               5                   10                  15

Asn Asp Tyr Phe Ser Thr Tyr Asn Gly Ala Lys Asn Pro Leu Val Gly
```

```
                20                  25                  30
Thr Glu Ala Ala Glu Gln Gly Ala Lys Leu Leu Ala Lys Phe Arg
            35                  40                  45

Gln Gln Gly Leu Pro Val Val His Val Arg His Glu Phe Pro Thr Asp
    50                  55                  60

Glu Ala Pro Phe Phe Leu Pro Gly Ser Asp Gly Ala Lys Ile His Pro
65                  70                  75                  80

Ser Val Ala Ala Gln Glu Gly Glu Ala Val Val Leu Lys His Gln Ile
                85                  90                  95

Asn Ser Phe Arg Asp Thr Asp Leu Lys Lys Val Leu Asp Asp Ala Gly
            100                 105                 110

Ile Lys Lys Leu Val Ile Val Gly Ala Met Thr
            115                 120

<210> SEQ ID NO 128
<211> LENGTH: 111
<212> TYPE: PRT
<213> ORGANISM: Artificial Sequence
<220> FEATURE:
<223> OTHER INFORMATION: Synthetic

<400> SEQUENCE: 128

Met Ala Ala Arg Lys Leu Ile Ala Arg Ile Asn Pro Thr Asn Ser Ala
1               5                   10                  15

Leu Phe Val Cys Asp Leu Gln Glu Lys Phe Ala Ser Asn Ile Lys Tyr
                20                  25                  30

Phe Pro Glu Ile Ile Thr Thr Ser Arg Arg Leu Ile Asp Ala Ala Arg
            35                  40                  45

Ile Leu Ser Ile Pro Thr Ile Val Thr Glu Gln Tyr Pro Lys Gly Leu
    50                  55                  60

Gly His Thr Val Pro Thr Leu Lys Glu Gly Leu Ala Glu Asn Thr Pro
65                  70                  75                  80

Ile Phe Asp Lys Thr Lys Phe Ser Met Cys Ile Pro Pro Thr Glu Asp
                85                  90                  95

Thr Leu Lys Lys Val Gln Asn Val Ile Leu Val Gly Ile Glu Ala
            100                 105                 110

<210> SEQ ID NO 129
<211> LENGTH: 119
<212> TYPE: PRT
<213> ORGANISM: Artificial Sequence
<220> FEATURE:
<223> OTHER INFORMATION: Synthetic

<400> SEQUENCE: 129

Gly Met Thr Thr Pro Arg Arg Ala Leu Ile Val Ile Asp Val Gln Asn
1               5                   10                  15

Glu Tyr Val Thr Gly Asp Leu Pro Ile Glu Tyr Pro Asp Val Gln Ser
                20                  25                  30

Ser Leu Ala Asn Ile Ala Arg Ala Met Asp Ala Ala Arg Ala Ala Gly
            35                  40                  45

Val Pro Val Val Ile Val Gln Asn Phe Ala Pro Ala Gly Ser Pro Leu
    50                  55                  60

Phe Ala Arg Gly Ser Asn Gly Ala Glu Leu His Pro Val Val Ser Glu
65                  70                  75                  80

Arg Ala Arg Asp His Tyr Val Glu Lys Ser Leu Pro Ser Ala Phe Thr
                85                  90                  95
```

Gly Thr Asp Leu Ala Gly Trp Leu Ala Arg Gln Ile Asp Thr Leu
            100                 105                 110

Thr Val Thr Gly Tyr Met Thr
            115

<210> SEQ ID NO 130
<211> LENGTH: 111
<212> TYPE: PRT
<213> ORGANISM: Artificial Sequence
<220> FEATURE:
<223> OTHER INFORMATION: Synthetic

<400> SEQUENCE: 130

Ala Met Lys Asn Arg Ala Leu Leu Ile Asp Phe Gln Lys Gly Ile
1               5                   10                  15

Glu Ser Pro Thr Gln Gln Leu Tyr Arg Leu Pro Ala Val Leu Asp Lys
                20                  25                  30

Val Asn Gln Arg Ile Ala Val Tyr Arg Gln His His Ala Pro Ile Ile
            35                  40                  45

Phe Val Gln His Glu Glu Thr Glu Leu Pro Phe Gly Ser Asp Ser Trp
    50                  55                  60

Gln Leu Phe Glu Lys Leu Asp Thr Gln Pro Thr Asp Phe Phe Ile Arg
65                  70                  75                  80

Lys Thr His Ala Asn Ala Phe Tyr Gln Thr Asn Leu Asn Asp Leu Leu
                85                  90                  95

Thr Glu Gln Ala Val Gln Thr Leu Glu Ile Ala Gly Val Gln Thr
            100                 105                 110

<210> SEQ ID NO 131
<211> LENGTH: 132
<212> TYPE: PRT
<213> ORGANISM: Artificial Sequence
<220> FEATURE:
<223> OTHER INFORMATION: Synthetic

<400> SEQUENCE: 131

Gly Met Ser Val Pro Thr Thr Met Phe Arg Leu Thr Gly Arg Asp Tyr
1               5                   10                  15

Pro Pro Ala Lys Leu Ser His Ala Ser Leu Ile Ile Asp Ala Gln
                20                  25                  30

Lys Glu Tyr Leu Ser Gly Pro Leu Lys Leu Ser Gly Met Asp Glu Ala
            35                  40                  45

Val Ala Asn Ile Ala Arg Leu Leu Asp Ala Ala Arg Lys Ser Gly Arg
    50                  55                  60

Pro Ile Ile His Val Arg His Leu Gly Thr Val Gly Arg Phe Asp
65                  70                  75                  80

Pro Gln Gly Pro Ala Gly Gln Phe Ile Pro Gly Leu Glu Pro Leu Glu
                85                  90                  95

Gly Glu Ile Val Ile Glu Lys Arg Met Pro Asn Ala Phe Lys Asn Thr
            100                 105                 110

Lys Leu His Glu Thr Leu Gln Glu Leu Gly His Leu Asp Leu Ile Val
        115                 120                 125

Cys Gly Phe Met
        130

<210> SEQ ID NO 132
<211> LENGTH: 135
<212> TYPE: PRT
<213> ORGANISM: Artificial Sequence -continued
<220> FEATURE:
<223> OTHER INFORMATION: Synthetic

<400> SEQUENCE: 132

Met Arg Ala Leu Ile Ile Val Asp Val Gln Asn Asp Phe Cys Glu Gly
1               5                   10                  15

Gly Ser Leu Ala Val Thr Gly Gly Ala Leu Ala Arg Ala Ile Ser
            20                  25                  30

Asp Tyr Leu Ala Glu Ala Ala Asp Tyr His His Val Val Ala Thr Lys
            35                  40                  45

Asp Phe His Ile Asp Pro Gly Asp His Phe Ser Gly Thr Pro Asp Tyr
        50                  55                  60

Ser Ser Ser Trp Pro Pro His Cys Val Ser Gly Thr Pro Gly Ala Asp
65                  70                  75                  80

Phe His Pro Ser Leu Asp Thr Ser Ala Ile Glu Ala Val Phe Tyr Lys
                85                  90                  95

Gly Ala Tyr Thr Gly Ala Tyr Ser Gly Phe Glu Gly Val Asp Glu Asn
            100                 105                 110

Gly Thr Pro Leu Leu Asn Trp Leu Arg Gln Arg Gly Val Asp Glu Val
        115                 120                 125

Asp Val Val Gly Ile Ala Thr
        130                 135

<210> SEQ ID NO 133
<211> LENGTH: 123
<212> TYPE: PRT
<213> ORGANISM: Artificial Sequence
<220> FEATURE:
<223> OTHER INFORMATION: Synthetic

<400> SEQUENCE: 133

Gly Met Pro Ala Pro Leu Arg Phe Ser Ser Asp Lys Pro Leu Leu Leu
1               5                   10                  15

Leu Ile Asp Met Gln Gln Ala Val Asp Asp Pro Ser Trp Gly Pro Arg
            20                  25                  30

Asn His Pro Gln Ala Glu Gln Ala Cys Ala Gly Leu Leu Gln Ala Trp
            35                  40                  45

Arg Ala Arg Gly Leu Pro Leu Ile His Ile Arg His Asp Ser Val Glu
        50                  55                  60

Pro Asn Ser Thr Tyr Arg Pro Gly Gln Pro Gly His Ala Phe Lys Pro
65                  70                  75                  80

Glu Val Glu Pro Arg Pro Gly Glu Thr Val Ile Ala Lys Gln Thr Asn
                85                  90                  95

Ser Ala Phe Ile Gly Thr Gly Leu Glu Ala Leu Leu Arg Ala Asn Gly
            100                 105                 110

Trp Leu Glu Leu Val Val Ala Gly Val Ser Thr
        115                 120

<210> SEQ ID NO 134
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: optionally absent

<400> SEQUENCE: 134

```
Met Ala Ser Ser His His His His His Met Ser Arg Leu Leu Lys
1               5                   10                  15

His Tyr Gly Ser Cys Lys Thr Ala Phe Phe Cys Cys Asp Ile Gln Glu
            20                  25                  30

Lys Phe Met Gly Arg Ile Ala Asn Ser Ala Asn Cys Val Phe Val Ala
        35                  40                  45

Asn Arg Phe Ala Gly Leu His Thr Ala Leu Gly Thr Ala His Ser Val
    50                  55                  60

Tyr Ile Val Thr Glu Gln Tyr Pro Lys Gly Leu Gly Ala Thr Ser Ala
65                  70                  75                  80

Asp Ile Arg Leu Pro Pro Asp Ala His Val Phe Ser Lys Lys Arg Phe
                85                  90                  95

Ala Met Leu Val Pro Gln Val Met Pro Leu Val Asp Leu Pro Glu Val
            100                 105                 110

Glu Gln Val Val Leu Trp Gly Phe Glu Thr
        115                 120
```

<210> SEQ ID NO 135
<211> LENGTH: 149
<212> TYPE: PRT
<213> ORGANISM: Artificial Sequence
<220> FEATURE:
<223> OTHER INFORMATION: Synthetic

<400> SEQUENCE: 135

```
Met Ser Leu Ala Glu Val Asn Pro Met Ser Lys Pro Leu Val Arg Trp
1               5                   10                  15

Pro Ile Asn Pro Leu Arg Thr Ala Val Ile Val Asp Met Gln Lys
            20                  25                  30

Val Phe Cys Glu Pro Thr Gly Ala Leu Tyr Val Lys Ser Thr Ala Asp
        35                  40                  45

Ile Val Gln Pro Ile Gln Lys Leu Leu Gln Ala Ala Arg Ala Ala Gln
    50                  55                  60

Val Met Val Ile Tyr Leu Arg His Ile Val Arg Gly Asp Gly Ser Asp
65                  70                  75                  80

Thr Gly Arg Met Arg Asp Leu Tyr Pro Asn Val Asp Gln Ile Leu Ala
                85                  90                  95

Arg His Asp Pro Asp Val Glu Ile Glu Ala Leu Ala Pro Gln Ser
            100                 105                 110

Asp Asp Val Ile Val Asp Lys Leu Phe Tyr Ser Gly Phe His Asn Thr
        115                 120                 125

Asp Leu Asp Thr Val Leu Arg Ala Arg Asp Val Asp Thr Ile Ile Val
    130                 135                 140

Cys Gly Thr Val Thr
145
```

<210> SEQ ID NO 136
<211> LENGTH: 130
<212> TYPE: PRT
<213> ORGANISM: Artificial Sequence
<220> FEATURE:
<223> OTHER INFORMATION: Synthetic

<400> SEQUENCE: 136

```
Tyr Phe Gln Gly Met Ala Lys His Ala Ile Leu Val Ile Asp Met Leu
1               5                   10                  15

Asn Asp Phe Val Gly Glu Lys Ala Pro Leu Arg Cys Pro Gly Gly Glu
```

```
                     20                  25                  30
Thr Ile Ile Pro Asp Leu Gln Lys Ile Phe Glu Trp Val Arg Gly Arg
         35                  40                  45

Glu Gly Asp Asp Ile His Leu Val His Ile Gln Glu Ala His Arg Lys
     50                  55                  60

Asn Asp Ala Asp Phe Arg Val Arg Pro Leu His Ala Val Lys Gly Thr
 65                  70                  75                  80

Trp Gly Ser Asp Phe Ile Pro Glu Leu Tyr Pro Gln Glu Asp Glu Tyr
                 85                  90                  95

Ile Val Gln Lys Arg Arg His Ser Gly Phe Ala His Thr Asp Leu Asp
            100                 105                 110

Leu Tyr Leu Lys Glu Glu Gly Ile Asp Thr Val Val Leu Thr Gly Val
        115                 120                 125

Trp Thr
    130

<210> SEQ ID NO 137
<211> LENGTH: 163
<212> TYPE: PRT
<213> ORGANISM: Artificial Sequence
<220> FEATURE:
<223> OTHER INFORMATION: Synthetic

<400> SEQUENCE: 137

Met Ser Leu Thr Thr Ser Lys Thr Arg Lys Ser Gly Val Ala Met Thr
 1               5                  10                  15

Glu Lys Leu Glu Leu Asp Pro Ala Arg Thr Ala Ile Val Leu Ile Glu
             20                  25                  30

Tyr Gln Asn Glu Phe Thr Ser Asp Gly Gly Val Leu His Gly Ala Val
         35                  40                  45

Ala Asp Val Met Gln His Thr Gly Met Leu Ala Asn Thr Val Ala Val
     50                  55                  60

Val Asp Ala Ala Arg Gln Ala Gly Val Pro Ile Met His Ala Pro Ile
 65                  70                  75                  80

Thr Phe Ala Glu Gly Tyr Gly Glu Leu Thr Arg His Pro Tyr Gly Ile
                 85                  90                  95

Leu Lys Gly Val Val Asp Gly Lys Ala Phe Val Lys Gly Thr Trp Gly
            100                 105                 110

Ala Ala Ile Val Asp Glu Leu Ala Pro Val Asn Gly Asp Ile Val Ile
        115                 120                 125

Glu Gly Lys Arg Gly Leu Asp Thr Phe Ala Ser Thr Asn Leu Asp Phe
    130                 135                 140

Ile Leu Arg Ser Lys Gly Val Asp Thr Ile Val Leu Gly Gly Phe Leu
145                 150                 155                 160

Thr Asn Cys

<210> SEQ ID NO 138
<211> LENGTH: 155
<212> TYPE: PRT
<213> ORGANISM: Artificial Sequence
<220> FEATURE:
<223> OTHER INFORMATION: Synthetic

<400> SEQUENCE: 138

Gly His Met Ala Ile Pro Lys Leu Gln Ala Tyr Ala Leu Pro Glu Ser
 1               5                  10                  15

His Asp Ile Pro Gln Asn Lys Val Asp Trp Ala Phe Glu Pro Gln Arg
```

```
            20                  25                  30
Ala Ala Leu Leu Ile His Asp Met Gln Asp Tyr Phe Val Ser Phe Trp
        35                  40                  45

Gly Glu Asn Cys Pro Met Met Glu Gln Val Ile Ala Asn Ile Ala Ala
    50                  55                  60

Leu Arg Asp Tyr Cys Lys Gln His Asn Ile Pro Val Tyr Tyr Thr Ala
65                  70                  75                  80

Gln Pro Lys Glu Gln Ser Asp Glu Asp Arg Ala Leu Leu Asn Asp Met
                85                  90                  95

Trp Gly Pro Gly Leu Thr Arg Ser Pro Glu Gln Gln Lys Val Val Asp
            100                 105                 110

Arg Leu Thr Pro Asp Ala Asp Thr Val Leu Val Lys Trp Arg Tyr
        115                 120                 125

Ser Ala Phe His Arg Ser Pro Leu Glu Gln Met Leu Lys Glu Ser Gly
        130                 135                 140

Arg Asn Gln Leu Ile Ile Thr Gly Val Tyr Ala
145                 150                 155
```

<210> SEQ ID NO 139
<211> LENGTH: 148
<212> TYPE: PRT
<213> ORGANISM: Artificial Sequence
<220> FEATURE:
<223> OTHER INFORMATION: Synthetic

<400> SEQUENCE: 139

```
Met Ala Ile Pro Lys Ile Ala Ser Tyr Pro Leu Pro Val Ser Leu Pro
1               5                   10                  15

Thr Asn Lys Val Asp Trp Arg Ile Asp Ala Ser Arg Ala Val Leu Leu
            20                  25                  30

Ile His Asn Met Gln Glu Tyr Phe Val His Tyr Phe Asp Ser Gln Ala
        35                  40                  45

Glu Pro Ile Pro Ser Leu Ile Lys His Ile Gln Gln Leu Lys Ala His
    50                  55                  60

Ala Lys Gln Ala Gly Ile Pro Val Val Tyr Thr Ala Gln Pro Ala Asn
65                  70                  75                  80

Gln Asp Pro Ala Glu Arg Ala Leu Leu Ser Asp Phe Trp Gly Pro Gly
                85                  90                  95

Leu Ser Glu Glu Thr Ala Ile Ile Ala Pro Leu Ala Pro Glu Ser Gly
            100                 105                 110

Asp Val Gln Leu Thr Lys Trp Arg Tyr Ser Ala Phe Lys Lys Ser Pro
        115                 120                 125

Leu Leu Asp Trp Leu Arg Glu Thr Gly Arg Asp Gln Leu Ile Ile Thr
        130                 135                 140

Gly Val Tyr Ala
145
```

<210> SEQ ID NO 140
<211> LENGTH: 129
<212> TYPE: PRT
<213> ORGANISM: Artificial Sequence
<220> FEATURE:
<223> OTHER INFORMATION: Synthetic

<400> SEQUENCE: 140

```
Pro Glu Glu Ala Leu Ile Val Val Asp Met Gln Arg Asp Phe Met Pro
1               5                   10                  15
```

```
Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr

<210> SEQ ID NO 141
<211> LENGTH: 179
<212> TYPE: PRT
<213> ORGANISM: Artificial Sequence
<220> FEATURE:
<223> OTHER INFORMATION: Synthetic

<400> SEQUENCE: 141

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Ala Thr Ala Glu Asp Ala Leu Lys His Gly
    130                 135                 140

Phe Glu Val Tyr Leu Leu Arg Asp Ala Val Lys Gly Ile Lys Pro Glu
145                 150                 155                 160

Met Glu Gln Gln Ala Phe Phe Tyr Met Lys Leu Arg Gly Ile Lys Ile
                165                 170                 175

Val Gln Phe

<210> SEQ ID NO 142
<211> LENGTH: 179
<212> TYPE: PRT
<213> ORGANISM: Artificial Sequence
<220> FEATURE:
<223> OTHER INFORMATION: Synthetic

<400> SEQUENCE: 142

Pro Glu Glu Ala Leu Ile Val Val Asp Met Gln Arg Asp Phe Met Pro
```

```
                1               5                   10                  15
Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
                35                  40                  45

Thr Arg Asp Trp His Pro Glu Asn His Ile Ser Phe Arg Glu Arg Gly
            50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
                115                 120                 125

Thr Glu Tyr Cys Val Ser Arg Thr Ala Val Asp Ala Lys His Lys Gly
                130                 135                 140

Phe Glu Val Tyr Leu Leu Arg Asp Ala Val Lys Gly Ile Lys Pro Glu
145                 150                 155                 160

Met Glu Gln Gln Ala Leu Phe Tyr Met Lys Leu Arg Gly Ile Lys Ile
                165                 170                 175

Val Gln Phe

<210> SEQ ID NO 143
<211> LENGTH: 179
<212> TYPE: PRT
<213> ORGANISM: Artificial Sequence
<220> FEATURE:
<223> OTHER INFORMATION: Synthetic

<400> SEQUENCE: 143

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
                35                  40                  45

Thr Arg Asp Trp His Pro Glu Asn His Ile Ser Phe Arg Glu Arg Gly
            50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
                115                 120                 125

Thr Glu Tyr Cys Val Ser Arg Thr Ala Val Asp Ala Leu Lys His Gly
                130                 135                 140

Phe Glu Val Tyr Leu Leu Arg Asp Ala Val Lys Gly Ile Lys Pro Thr
145                 150                 155                 160

Phe Glu Gln Gln Ser Phe Phe Tyr Met Ser Leu Lys Gly Ile Lys Ile
                165                 170                 175

Val Gln Phe
```

<210> SEQ ID NO 144
<211> LENGTH: 179
<212> TYPE: PRT
<213> ORGANISM: Artificial Sequence
<220> FEATURE:
<223> OTHER INFORMATION: Synthetic

<400> SEQUENCE: 144

```
Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Ala Val Ser Arg Thr Ala Val Asp Ala Leu Lys His Gly
    130                 135                 140

Phe Glu Val Tyr Leu Leu Arg Asp Ala Val Lys Gly Ile Lys Pro Thr
145                 150                 155                 160

Phe Glu Gln Gln Ser Phe Phe Tyr Met Ser Leu Lys Gly Ile Lys Ile
                165                 170                 175

Val Gln Phe
```

<210> SEQ ID NO 145
<211> LENGTH: 179
<212> TYPE: PRT
<213> ORGANISM: Artificial Sequence
<220> FEATURE:
<223> OTHER INFORMATION: Synthetic

<400> SEQUENCE: 145

```
Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125
```

```
Thr Glu Tyr Cys Val Ser Val Thr Ala Leu Asp Ala Leu Lys His Gly
        130                 135                 140

Phe Glu Val Tyr Leu Leu Arg Asp Ala Val Lys Gly Ile Lys Pro Trp
145                 150                 155                 160

Leu Glu Gln Gln Ser Phe Phe Tyr Met Arg Leu Lys Gly Ile Lys Ile
                165                 170                 175

Val Gln Phe

<210> SEQ ID NO 146
<211> LENGTH: 179
<212> TYPE: PRT
<213> ORGANISM: Artificial Sequence
<220> FEATURE:
<223> OTHER INFORMATION: Synthetic

<400> SEQUENCE: 146

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
50                  55                  60

Ser Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Arg Thr Ala Ala Asp Ala Leu Lys His Gly
        130                 135                 140

Phe Glu Val Tyr Leu Leu Arg Asp Ala Val Lys Gly Ile Lys Pro Trp
145                 150                 155                 160

Leu Glu Gln Gln Ser Phe Phe Tyr Met Ala Leu Lys Gly Ile Lys Ile
                165                 170                 175

Val Gln Phe

<210> SEQ ID NO 147
<211> LENGTH: 179
<212> TYPE: PRT
<213> ORGANISM: Artificial Sequence
<220> FEATURE:
<223> OTHER INFORMATION: Synthetic

<400> SEQUENCE: 147

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
```

```
                65                  70                  75                  80
Val Val Asp Leu Pro Glu Asp Ala Val Ile Ile Ser Lys Ala Thr Glu
                85                  90                  95
Pro Asp Lys Glu Ala Tyr Ser Gly Phe Glu Gly Thr Asp Leu Ala Lys
                100                 105                 110
Ile Leu Arg Gly Asn Gly Val Lys Arg Val Tyr Ile Cys Gly Val Ala
                115                 120                 125
Thr Glu Tyr Cys Val Ser Arg Thr Ala Val Asp Ala Leu Lys His Gly
                130                 135                 140
Phe Glu Val Tyr Leu Leu Arg Asp Ala Val Lys Gly Ile Lys Pro Val
145                 150                 155                 160
Trp Glu Gln Gln Ser Phe Phe Tyr Met Val Leu Lys Gly Ile Lys Ile
                165                 170                 175
Val Gln Phe

<210> SEQ ID NO 148
<211> LENGTH: 179
<212> TYPE: PRT
<213> ORGANISM: Artificial Sequence
<220> FEATURE:
<223> OTHER INFORMATION: Synthetic

<400> SEQUENCE: 148

Pro Glu Glu Ala Leu Ile Val Val Asp Met Gln Arg Asp Phe Met Pro
1               5                   10                  15
Gly Gly Ala Leu Pro Val Pro Glu Gly Asp Lys Ile Ile Pro Lys Val
                20                  25                  30
Asn Glu Tyr Ile Arg Lys Phe Lys Glu Lys Gly Ala Leu Ile Val Ala
                35                  40                  45
Thr Arg Asp Trp His Pro Glu Asn His Ile Ser Phe Arg Glu Arg Gly
                50                  55                  60
Gly Pro Trp Pro Arg His Cys Val Gln Asn Thr Pro Gly Ala Glu Phe
65                  70                  75                  80
Val Val Asp Leu Pro Glu Asp Ala Val Ile Ile Ser Lys Ala Thr Glu
                85                  90                  95
Pro Asp Lys Glu Ala Tyr Ser Gly Phe Glu Gly Thr Asp Leu Ala Lys
                100                 105                 110
Ile Leu Arg Gly Asn Gly Val Lys Arg Val Tyr Ile Cys Gly Val Ala
                115                 120                 125
Thr Glu Tyr Cys Val Ser Leu Thr Ala Val Asp Ala Leu Lys His Gly
                130                 135                 140
Phe Glu Val Tyr Leu Leu Arg Asp Ala Val Lys Gly Ile Lys Pro Trp
145                 150                 155                 160
His Glu Gln Gln Ser Phe Phe Tyr Met Leu Leu Lys Gly Ile Lys Ile
                165                 170                 175
Val Gln Phe

<210> SEQ ID NO 149
<211> LENGTH: 179
<212> TYPE: PRT
<213> ORGANISM: Artificial Sequence
<220> FEATURE:
<223> OTHER INFORMATION: Synthetic

<400> SEQUENCE: 149

Pro Glu Glu Ala Leu Ile Val Val Asp Met Gln Arg Asp Phe Met Pro
1               5                   10                  15
```

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser His Thr Ala Met Asp Ala Leu Lys His Gly
            130                 135                 140

Phe Glu Val Tyr Leu Leu Arg Asp Ala Val Lys Gly Ile Lys Pro His
145                 150                 155                 160

Trp Glu Gln Gln Ser Phe Phe Tyr Met Leu Leu Lys Gly Ile Lys Ile
                165                 170                 175

Val Gln Phe

<210> SEQ ID NO 150
<211> LENGTH: 179
<212> TYPE: PRT
<213> ORGANISM: Artificial Sequence
<220> FEATURE:
<223> OTHER INFORMATION: Synthetic

<400> SEQUENCE: 150

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Pro Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Leu Thr Ala Val Asp Ala Leu Lys His Gly
            130                 135                 140

Phe Glu Val Tyr Leu Leu Arg Asp Ala Val Lys Gly Ile Lys Pro Lys
145                 150                 155                 160

Ile Glu Gln Gln Ser Phe Phe Tyr Met Met Leu Lys Gly Ile Lys Ile
                165                 170                 175

Val Gln Phe

<210> SEQ ID NO 151
<211> LENGTH: 179
<212> TYPE: PRT
<213> ORGANISM: Artificial Sequence
<220> FEATURE:
<223> OTHER INFORMATION: Synthetic

<400> SEQUENCE: 151

```
Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Arg Thr Ala Met Asp Ala Leu Lys His Gly
130                 135                 140

Phe Glu Val Tyr Leu Leu Arg Asp Ala Val Lys Gly Ile Lys Pro Phe
145                 150                 155                 160

Leu Glu Gln Gln Ser Phe Phe Tyr Met Arg Leu Lys Gly Ile Lys Ile
                165                 170                 175

Val Gln Phe
```

<210> SEQ ID NO 152
<211> LENGTH: 179
<212> TYPE: PRT
<213> ORGANISM: Artificial Sequence
<220> FEATURE:
<223> OTHER INFORMATION: Synthetic

<400> SEQUENCE: 152

```
Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser His Thr Ala Val Asp Ala Leu Lys His Gly
```

```
                130                 135                 140
Phe Glu Val Tyr Leu Leu Arg Asp Ala Val Lys Gly Ile Lys Pro Trp
145                 150                 155                 160

Leu Glu Gln Gln Ser Phe Phe Tyr Met Arg Leu Lys Gly Ile Lys Ile
                165                 170                 175

Val Gln Phe

<210> SEQ ID NO 153
<211> LENGTH: 179
<212> TYPE: PRT
<213> ORGANISM: Artificial Sequence
<220> FEATURE:
<223> OTHER INFORMATION: Synthetic

<400> SEQUENCE: 153

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
        50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Trp Thr Ala Val Asp Ala Leu Lys His Gly
    130                 135                 140

Phe Glu Val Tyr Leu Leu Arg Asp Ala Val Lys Gly Ile Lys Pro His
145                 150                 155                 160

Met Glu Gln Gln Ser Phe Phe Tyr Met Met Leu Lys Gly Ile Lys Ile
                165                 170                 175

Val Gln Phe

<210> SEQ ID NO 154
<211> LENGTH: 179
<212> TYPE: PRT
<213> ORGANISM: Artificial Sequence
<220> FEATURE:
<223> OTHER INFORMATION: Synthetic

<400> SEQUENCE: 154

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
        50                  55                  60

Gly Pro Trp Pro Arg His Cys Val Gln Asn Thr Pro Gly Ala Glu Phe
65                  70                  75                  80
```

```
Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Arg Thr Ala Val Asp Ala Leu Lys His Gly
    130                 135                 140

Phe Glu Val Tyr Leu Leu Arg Asp Ala Val Lys Gly Ile Lys Pro Trp
145                 150                 155                 160

Leu Glu Gln Gln Ala Phe Phe Tyr Met Glu Leu Lys Gly Ile Lys Ile
                165                 170                 175

Val Gln Phe

<210> SEQ ID NO 155
<211> LENGTH: 179
<212> TYPE: PRT
<213> ORGANISM: Artificial Sequence
<220> FEATURE:
<223> OTHER INFORMATION: Synthetic

<400> SEQUENCE: 155

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Arg Thr Ala Arg Asp Ala Leu Lys His Gly
    130                 135                 140

Phe Glu Val Tyr Leu Leu Arg Asp Ala Val Lys Gly Ile Lys Pro Trp
145                 150                 155                 160

Leu Glu Gln Gln Ser Phe Phe Tyr Met Lys Leu Lys Gly Ile Lys Ile
                165                 170                 175

Val Gln Phe

<210> SEQ ID NO 156
<211> LENGTH: 179
<212> TYPE: PRT
<213> ORGANISM: Artificial Sequence
<220> FEATURE:
<223> OTHER INFORMATION: Synthetic

<400> SEQUENCE: 156

Pro Glu Glu Ala Leu Ile Val Val Asp Met Gln Arg Asp Phe Met Pro
1               5                   10                  15
```

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ala Phe Thr Ala Val Asp Ala Leu Lys His Gly
            130                 135                 140

Phe Glu Val Tyr Leu Leu Arg Asp Ala Val Lys Gly Ile Lys Pro Trp
145                 150                 155                 160

Leu Glu Gln Gln Ser Phe Phe Tyr Met Gln Leu Lys Gly Ile Lys Ile
                165                 170                 175

Val Gln Phe

<210> SEQ ID NO 157
<211> LENGTH: 179
<212> TYPE: PRT
<213> ORGANISM: Artificial Sequence
<220> FEATURE:
<223> OTHER INFORMATION: Synthetic

<400> SEQUENCE: 157

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Leu Thr Ala Val Asp Ala Leu Lys His Gly
            130                 135                 140

Phe Glu Val Tyr Leu Leu Arg Asp Ala Val Lys Gly Ile Lys Pro Trp
145                 150                 155                 160

His Glu Gln Gln Ser Phe Phe Tyr Met Leu Leu Lys Gly Ile Lys Ile
                165                 170                 175

Val Gln Phe

<210> SEQ ID NO 158

```
<211> LENGTH: 179
<212> TYPE: PRT
<213> ORGANISM: Artificial Sequence
<220> FEATURE:
<223> OTHER INFORMATION: Synthetic

<400> SEQUENCE: 158

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser His Thr Ala Val Asp Ala Leu Lys His Gly
    130                 135                 140

Phe Glu Val Tyr Leu Leu Arg Asp Ala Val Lys Gly Ile Lys Pro Trp
145                 150                 155                 160

Leu Glu Gln Gln Ser Phe Phe Tyr Met Arg Leu Lys Gly Ile Lys Ile
                165                 170                 175

Val Gln Phe

<210> SEQ ID NO 159
<211> LENGTH: 179
<212> TYPE: PRT
<213> ORGANISM: Artificial Sequence
<220> FEATURE:
<223> OTHER INFORMATION: Synthetic

<400> SEQUENCE: 159

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Trp Thr Ala Met Asp Ala Leu Lys His Gly
    130                 135                 140
```

Phe Glu Val Tyr Leu Leu Arg Asp Ala Val Lys Gly Ile Lys Pro Pro
145                 150                 155                 160

Ile Glu Gln Gln Ser Phe Phe Tyr Met His Leu Lys Gly Ile Lys Ile
                165                 170                 175

Val Gln Phe

<210> SEQ ID NO 160
<211> LENGTH: 179
<212> TYPE: PRT
<213> ORGANISM: Artificial Sequence
<220> FEATURE:
<223> OTHER INFORMATION: Synthetic

<400> SEQUENCE: 160

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Phe Thr Ala Ala Asp Ala Leu Lys His Gly
130                 135                 140

Phe Glu Val Tyr Leu Leu Arg Asp Ala Val Lys Gly Ile Lys Pro Trp
145                 150                 155                 160

Ala Glu Gln Gln Ser Phe Phe Tyr Met Gly Leu Lys Gly Ile Lys Ile
                165                 170                 175

Val Gln Phe

<210> SEQ ID NO 161
<211> LENGTH: 179
<212> TYPE: PRT
<213> ORGANISM: Artificial Sequence
<220> FEATURE:
<223> OTHER INFORMATION: Synthetic

<400> SEQUENCE: 161

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
        50                  55                  60

Gly Pro Trp Pro Arg His Cys Val Gln Asn Thr Pro Gly Ala Glu Phe
65                  70                  75                  80

```
Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Arg Thr Ala Val Asp Ala Leu Lys His Gly
130                 135                 140

Phe Glu Val Tyr Leu Leu Arg Asp Ala Val Lys Gly Ile Lys Pro Val
145                 150                 155                 160

Leu Glu Gln Gln Ser Phe Phe Tyr Met Asp Leu Lys Gly Ile Lys Ile
                165                 170                 175

Val Gln Phe

<210> SEQ ID NO 162
<211> LENGTH: 179
<212> TYPE: PRT
<213> ORGANISM: Artificial Sequence
<220> FEATURE:
<223> OTHER INFORMATION: Synthetic

<400> SEQUENCE: 162

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Arg Thr Ala Met Asp Ala Leu Lys His Gly
130                 135                 140

Phe Glu Val Tyr Leu Leu Arg Asp Ala Val Lys Gly Ile Lys Pro Arg
145                 150                 155                 160

Leu Glu Gln Gln Ser Phe Phe Tyr Met Thr Leu Lys Gly Ile Lys Ile
                165                 170                 175

Val Gln Phe

<210> SEQ ID NO 163
<211> LENGTH: 179
<212> TYPE: PRT
<213> ORGANISM: Artificial Sequence
<220> FEATURE:
<223> OTHER INFORMATION: Synthetic

<400> SEQUENCE: 163

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
```

```
                    20                  25                  30
Asn Glu Tyr Ile Arg Lys Phe Lys Glu Lys Gly Ala Leu Ile Val Ala
                35                  40                  45

Thr Arg Asp Trp His Pro Glu Asn His Ile Ser Phe Arg Glu Arg Gly
             50                  55                  60

Gly Pro Trp Pro Arg His Cys Val Gln Asn Thr Pro Gly Ala Glu Phe
 65                  70                  75                  80

Val Val Asp Leu Pro Glu Asp Ala Val Ile Ile Ser Lys Ala Thr Glu
                 85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
                115                 120                 125

Thr Glu Tyr Cys Val Ser Thr Thr Ala Ile Asp Ala Leu Lys His Gly
                130                 135                 140

Phe Glu Val Tyr Leu Leu Arg Asp Ala Val Lys Gly Ile Lys Pro Gly
145                 150                 155                 160

Met Glu Gln Gln Ser Phe Phe Tyr Met Ile Leu Lys Gly Ile Lys Ile
                165                 170                 175

Val Gln Phe

<210> SEQ ID NO 164
<211> LENGTH: 179
<212> TYPE: PRT
<213> ORGANISM: Artificial Sequence
<220> FEATURE:
<223> OTHER INFORMATION: Synthetic

<400> SEQUENCE: 164

Pro Glu Glu Ala Leu Ile Val Val Asp Met Gln Arg Asp Phe Met Pro
 1               5                  10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
                35                  40                  45

Thr Arg Asp Trp His Pro Glu Asn His Ile Ser Phe Arg Glu Arg Gly
             50                  55                  60

Gly Pro Trp Pro Arg His Cys Val Gln Asn Thr Pro Gly Ala Glu Phe
 65                  70                  75                  80

Val Val Asp Leu Pro Glu Asp Ala Val Ile Ile Ser Lys Ala Thr Glu
                 85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
                115                 120                 125

Thr Glu Tyr Cys Val Ser Leu Thr Ala Val Asp Ala Leu Lys His Gly
                130                 135                 140

Phe Glu Val Tyr Leu Leu Arg Asp Ala Val Lys Gly Ile Lys Pro Met
145                 150                 155                 160

Ile Glu Gln Gln Ser Phe Phe Tyr Met Arg Leu Lys Gly Ile Lys Ile
                165                 170                 175

Val Gln Phe

<210> SEQ ID NO 165
<211> LENGTH: 179
```

```
<212> TYPE: PRT
<213> ORGANISM: Artificial Sequence
<220> FEATURE:
<223> OTHER INFORMATION: Synthetic

<400> SEQUENCE: 165

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Lys Thr Ala Thr Asp Ala Leu Lys His Gly
130                 135                 140

Phe Glu Val Tyr Leu Leu Arg Asp Ala Val Lys Gly Ile Lys Pro Ser
145                 150                 155                 160

Leu Glu Gln Gln Ser Phe Phe Tyr Met Arg Leu Lys Gly Ile Lys Ile
                165                 170                 175

Val Gln Phe

<210> SEQ ID NO 166
<211> LENGTH: 178
<212> TYPE: PRT
<213> ORGANISM: Artificial Sequence
<220> FEATURE:
<223> OTHER INFORMATION: Synthetic

<400> SEQUENCE: 166

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Arg Thr Ala Val Asp Ala Leu Lys His Gly
130                 135                 140
```

```
Phe Glu Val Tyr Leu Leu Arg Asp Ala Val Lys Gly Ile Lys Pro Arg
145                 150                 155                 160

Leu Glu Gln Gln Ser Phe Phe Tyr Met Ser Leu Lys Gly Ile Lys Ile
                165                 170                 175

Val Gln

<210> SEQ ID NO 167
<211> LENGTH: 179
<212> TYPE: PRT
<213> ORGANISM: Artificial Sequence
<220> FEATURE:
<223> OTHER INFORMATION: Synthetic

<400> SEQUENCE: 167

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
        50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
            115                 120                 125

Thr Glu Tyr Cys Val Ser Met Thr Ala Met Asp Ala Leu Lys His Gly
        130                 135                 140

Phe Glu Val Tyr Leu Leu Arg Asp Ala Val Lys Gly Ile Lys Pro Ser
145                 150                 155                 160

Leu Glu Gln Gln Ser Phe Phe Tyr Met Asn Leu Lys Gly Ile Lys Ile
                165                 170                 175

Val Gln Phe

<210> SEQ ID NO 168
<211> LENGTH: 179
<212> TYPE: PRT
<213> ORGANISM: Artificial Sequence
<220> FEATURE:
<223> OTHER INFORMATION: Synthetic

<400> SEQUENCE: 168

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
                20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
        50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
```

```
                    85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
            115                 120                 125

Thr Glu Tyr Cys Val Ser Arg Thr Ala Met Asp Ala Leu Lys His Gly
        130                 135                 140

Phe Glu Val Tyr Leu Leu Arg Asp Ala Val Lys Gly Ile Lys Pro Thr
145                 150                 155                 160

Glu Glu Gln Gln Ser Phe Phe Tyr Met Thr Leu Lys Gly Ile Lys Ile
                165                 170                 175

Val Gln Phe

<210> SEQ ID NO 169
<211> LENGTH: 179
<212> TYPE: PRT
<213> ORGANISM: Artificial Sequence
<220> FEATURE:
<223> OTHER INFORMATION: Synthetic

<400> SEQUENCE: 169

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
                100                 105                 110

Ile Leu Arg Gly Asn Gly Val Lys Arg Val Tyr Ile Cys Gly Val Ala
            115                 120                 125

Thr Glu Tyr Cys Val Ala Met Thr Ala Val Asp Ala Leu Lys His Gly
        130                 135                 140

Phe Glu Val Tyr Leu Leu Arg Asp Ala Val Lys Gly Ile Lys Pro Trp
145                 150                 155                 160

Leu Glu Gln Gln Ser Phe Phe Tyr Met His Leu Lys Gly Ile Lys Ile
                165                 170                 175

Val Gln Phe

<210> SEQ ID NO 170
<211> LENGTH: 179
<212> TYPE: PRT
<213> ORGANISM: Artificial Sequence
<220> FEATURE:
<223> OTHER INFORMATION: Synthetic

<400> SEQUENCE: 170

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30
```

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Arg Thr Ala Val Asp Ala Leu Lys His Gly
    130                 135                 140

Phe Glu Val Tyr Leu Leu Arg Asp Ala Val Lys Gly Ile Lys Pro Thr
145                 150                 155                 160

Phe Glu Gln Gln Ser Phe Phe Tyr Met Ser Leu Lys Gly Ile Lys Ile
                165                 170                 175

Val Gln Phe

<210> SEQ ID NO 171
<211> LENGTH: 179
<212> TYPE: PRT
<213> ORGANISM: Artificial Sequence
<220> FEATURE:
<223> OTHER INFORMATION: Synthetic

<400> SEQUENCE: 171

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Arg Thr Ala Met Asp Ala Leu Lys His Gly
    130                 135                 140

Phe Glu Val Tyr Leu Leu Arg Asp Ala Val Lys Gly Ile Lys Pro Thr
145                 150                 155                 160

Glu Glu Gln Gln Ser Phe Phe Tyr Met Thr Leu Lys Gly Ile Lys Ile
                165                 170                 175

Val Gln Phe

<210> SEQ ID NO 172
<211> LENGTH: 179
<212> TYPE: PRT

<213> ORGANISM: Artificial Sequence
<220> FEATURE:
<223> OTHER INFORMATION: Synthetic

<400> SEQUENCE: 172

```
Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Ala Thr Ala Glu Asp Ala Leu Lys His Gly
    130                 135                 140

Phe Glu Val Tyr Leu Leu Arg Asp Ala Val Lys Gly Ile Lys Pro Glu
145                 150                 155                 160

Arg Glu Gln Gln Ser Phe Phe Tyr Met Gly Leu Lys Gly Ile Lys Ile
                165                 170                 175

Val Gln Phe
```

<210> SEQ ID NO 173
<211> LENGTH: 179
<212> TYPE: PRT
<213> ORGANISM: Artificial Sequence
<220> FEATURE:
<223> OTHER INFORMATION: Synthetic

<400> SEQUENCE: 173

```
Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Ala Thr Ala Glu Asp Ala Leu Lys His Gly
    130                 135                 140

Phe Glu Val Tyr Leu Leu Arg Asp Ala Val Lys Gly Ile Lys Pro Glu
```

Arg Glu Gln Gln Ser Phe Phe Tyr Met Gly Leu Lys Gly Ile Lys Ile
145                 150                 155                 160

Val Gln Phe
            165                 170                 175

<210> SEQ ID NO 174
<211> LENGTH: 179
<212> TYPE: PRT
<213> ORGANISM: Artificial Sequence
<220> FEATURE:
<223> OTHER INFORMATION: Synthetic

<400> SEQUENCE: 174

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Ala Thr Ala Glu Asp Ala Leu Lys His Gly
    130                 135                 140

Phe Glu Val Tyr Leu Leu Arg Asp Ala Val Lys Gly Ile Lys Pro His
145                 150                 155                 160

Met Lys Gln Gln Ser Phe Phe Tyr Met Ser Leu Arg Gly Ile Lys Ile
                165                 170                 175

Val Gln Phe

<210> SEQ ID NO 175
<211> LENGTH: 179
<212> TYPE: PRT
<213> ORGANISM: Artificial Sequence
<220> FEATURE:
<223> OTHER INFORMATION: Synthetic

<400> SEQUENCE: 175

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

```
Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Ala Thr Ala Glu Asp Ala Leu Lys His Gly
        130                 135                 140

Phe Glu Val Tyr Leu Leu Arg Asp Ala Val Lys Gly Ile Lys Pro His
145                 150                 155                 160

Trp Val Gln Gln Ser Phe Phe Tyr Met Gly Leu Lys Gly Ile Lys Ile
                165                 170                 175

Val Gln Phe

<210> SEQ ID NO 176
<211> LENGTH: 179
<212> TYPE: PRT
<213> ORGANISM: Artificial Sequence
<220> FEATURE:
<223> OTHER INFORMATION: Synthetic

<400> SEQUENCE: 176

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
            35                  40                  45

Thr Arg Asp Trp His Pro Glu Asn His Ile Ser Phe Arg Glu Arg Gly
        50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Ala Thr Ala Glu Asp Ala Leu Lys His Gly
        130                 135                 140

Phe Glu Val Tyr Leu Leu Arg Asp Ala Val Lys Gly Ile Lys Pro Asp
145                 150                 155                 160

Trp Val Gln Gln Ser Met Phe Tyr Met Glu Leu Lys Gly Ile Lys Ile
                165                 170                 175

Val Gln Phe

<210> SEQ ID NO 177
<211> LENGTH: 179
<212> TYPE: PRT
<213> ORGANISM: Artificial Sequence
<220> FEATURE:
<223> OTHER INFORMATION: Synthetic

<400> SEQUENCE: 177

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30
```

```
Asn Glu Tyr Ile Arg Lys Phe Lys Glu Lys Gly Ala Leu Ile Val Ala
             35                  40                  45

Thr Arg Asp Trp His Pro Glu Asn His Ile Ser Phe Arg Glu Arg Gly
 50                  55                  60

Gly Pro Trp Pro Arg His Cys Val Gln Asn Thr Pro Gly Ala Glu Phe
 65                  70                  75                  80

Val Val Asp Leu Pro Glu Asp Ala Val Ile Ile Ser Lys Ala Thr Glu
                 85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Ala Thr Ala Glu Asp Ala Leu Lys His Gly
        130                 135                 140

Phe Glu Val Tyr Leu Leu Arg Asp Ala Val Lys Gly Ile Lys Pro Asp
145                 150                 155                 160

Trp Val Gln Gln Ser Leu Phe Tyr Met Asn Leu Lys Gly Ile Lys Ile
                165                 170                 175

Val Gln Phe

<210> SEQ ID NO 178
<211> LENGTH: 179
<212> TYPE: PRT
<213> ORGANISM: Artificial Sequence
<220> FEATURE:
<223> OTHER INFORMATION: Synthetic

<400> SEQUENCE: 178

Pro Glu Glu Ala Leu Ile Val Val Asp Met Gln Arg Asp Phe Met Pro
 1               5                  10                  15

Gly Gly Ala Leu Pro Val Pro Glu Gly Asp Lys Ile Ile Pro Lys Val
                 20                  25                  30

Asn Glu Tyr Ile Arg Lys Phe Lys Glu Lys Gly Ala Leu Ile Val Ala
             35                  40                  45

Thr Arg Asp Trp His Pro Glu Asn His Ile Ser Phe Arg Glu Arg Gly
 50                  55                  60

Gly Pro Trp Pro Arg His Cys Val Gln Asn Thr Pro Gly Ala Glu Phe
 65                  70                  75                  80

Val Val Asp Leu Pro Glu Asp Ala Val Ile Ile Ser Lys Ala Thr Glu
                 85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
            115                 120                 125

Thr Glu Tyr Cys Val Ser Ala Thr Ala Glu Asp Ala Leu Lys His Gly
        130                 135                 140

Phe Glu Val Tyr Leu Leu Arg Asp Ala Val Lys Gly Ile Lys Pro Glu
145                 150                 155                 160

Trp Val Gln Gln Ser Leu Phe Tyr Met Gly Leu Lys Gly Ile Lys Ile
                165                 170                 175

Val Gln Phe

<210> SEQ ID NO 179
<211> LENGTH: 178
<212> TYPE: PRT
<213> ORGANISM: Artificial Sequence
```

<220> FEATURE:
<223> OTHER INFORMATION: Synthetic

<400> SEQUENCE: 179

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Ala Thr Ala Glu Asp Ala Leu Lys His Gly
130                 135                 140

Phe Glu Val Tyr Leu Leu Arg Asp Ala Val Lys Gly Ile Lys Pro Glu
145                 150                 155                 160

Met Glu Gln Gln Ala Phe Phe Tyr Met Lys Leu Arg Gly Ile Lys Ile
                165                 170                 175

Val Gln

<210> SEQ ID NO 180
<211> LENGTH: 179
<212> TYPE: PRT
<213> ORGANISM: Artificial Sequence
<220> FEATURE:
<223> OTHER INFORMATION: Synthetic

<400> SEQUENCE: 180

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Val Thr Ala Val Asp Ala Leu Lys His Gly
130                 135                 140

Phe Glu Val Tyr Leu Leu Arg Asp Ala Val Lys Gly Ile Lys Pro Glu
145                 150                 155                 160

Met Glu Gln Gln Ala Leu Phe Tyr Met Lys Leu Arg Gly Ile Lys Ile
                165                 170                 175

Val Gln Phe

<210> SEQ ID NO 181
<211> LENGTH: 179
<212> TYPE: PRT
<213> ORGANISM: Artificial Sequence
<220> FEATURE:
<223> OTHER INFORMATION: Synthetic

<400> SEQUENCE: 181

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Val
        35                  40                  45

Thr Arg Glu Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Thr Thr Ala Val Asp Ala Leu Lys His Gly
    130                 135                 140

Phe Glu Val Tyr Leu Leu Arg Asp Ala Val Lys Gly Ile Lys Pro Glu
145                 150                 155                 160

Met Glu Gln Gln Ala Leu Phe Tyr Met Lys Leu Arg Gly Ile Lys Ile
                165                 170                 175

Val Gln Phe

<210> SEQ ID NO 182
<211> LENGTH: 179
<212> TYPE: PRT
<213> ORGANISM: Artificial Sequence
<220> FEATURE:
<223> OTHER INFORMATION: Synthetic

<400> SEQUENCE: 182

Pro Glu Glu Ala Leu Ile Val Val Asp Met Gln Arg Asp Phe Met Pro
1               5                   10                  15

Gly Gly Ala Leu Pro Val Pro Glu Gly Asp Lys Ile Ile Pro Lys Val
            20                  25                  30

Asn Glu Tyr Ile Arg Lys Phe Lys Glu Lys Gly Ala Leu Ile Val Ala
        35                  40                  45

Thr Arg Asp Trp His Pro Glu Asn His Ile Ser Phe Arg Glu Arg Gly
    50                  55                  60

Gly Pro Trp Pro Arg His Cys Val Gln Asn Thr Pro Gly Ala Glu Phe
65                  70                  75                  80

Val Val Asp Leu Pro Glu Asp Ala Val Ile Ile Ser Lys Ala Thr Glu
                85                  90                  95

```
Pro Asp Lys Glu Ala Tyr Ser Gly Phe Glu Gly Thr Asp Leu Ala Lys
            100                 105                 110

Ile Leu Arg Gly Asn Gly Val Lys Arg Val Tyr Ile Cys Gly Val Ala
        115                 120                 125

Thr Glu Tyr Cys Val Ser Arg Thr Ala Val Asp Ala Arg Lys His Gly
    130                 135                 140

Phe Glu Val Tyr Leu Leu Arg Asp Ala Val Lys Gly Ile Lys Pro Glu
145                 150                 155                 160

Met Glu Gln Gln Ala Leu Phe Tyr Met Lys Leu Arg Gly Ile Lys Ile
                165                 170                 175

Val Gln Phe

<210> SEQ ID NO 183
<211> LENGTH: 13
<212> TYPE: PRT
<213> ORGANISM: Artificial Sequence
<220> FEATURE:
<223> OTHER INFORMATION: Synthetic

<400> SEQUENCE: 183

Gly Gly Gly Ser Cys Leu Glu His His His His His His
1               5                   10

<210> SEQ ID NO 184
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is A or C
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (11)..(13)
<223> OTHER INFORMATION: Xaa is any amino acid

<400> SEQUENCE: 184

Glu Tyr Xaa Val Ser Xaa Thr Ala Xaa Asp Xaa Xaa Xaa His
1               5                   10

<210> SEQ ID NO 185
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
```

```
<221> NAME/KEY: MISC_FEATURE
<222> LOCATION: (14)..(14)
<223> OTHER INFORMATION: Xaa is any amino acid

<400> SEQUENCE: 185

Gly Xaa Xaa Xaa Xaa Leu Xaa Arg Xaa Ala Val Lys Gly Xaa Lys Pro
1               5                   10                  15

<210> SEQ ID NO 186
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is any amino acid
<220> FEATURE:
<221> NAME/KEY: MISC_FEATURE
<222> LOCATION: (11)..(13)
<223> OTHER INFORMATION: Xaa is any amino acid

<400> SEQUENCE: 186

Xaa Xaa Xaa Gln Gln Xaa Xaa Phe Tyr Met Xaa Xaa Xaa
1               5                   10

<210> SEQ ID NO 187
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is V or I
<220> FEATURE:
<221> NAME/KEY: MISC_FEATURE
<222> LOCATION: (6)..(6)
<223> OTHER INFORMATION: Xaa is E, H, Q or D
<220> FEATURE:
<221> NAME/KEY: MISC_FEATURE
<222> LOCATION: (7)..(7)
<223> OTHER INFORMATION: Xaa is M, F, S, I, R, W or C
<220> FEATURE:
<221> NAME/KEY: MISC_FEATURE
<222> LOCATION: (8)..(8)
<223> OTHER INFORMATION: Xaa is M, E, Q, K, L, or V
<220> FEATURE:
<221> NAME/KEY: MISC_FEATURE
<222> LOCATION: (11)..(11)
<223> OTHER INFORMATION: Xaa is A, S, or G
<220> FEATURE:
<221> NAME/KEY: MISC_FEATURE
<222> LOCATION: (12)..(12)
<223> OTHER INFORMATION: Xaa is F, M, I or L
<220> FEATURE:
<221> NAME/KEY: MISC_FEATURE
<222> LOCATION: (16)..(16)
<223> OTHER INFORMATION: Xaa is E, G, M, S, V, K, R, I, N, S or D
<220> FEATURE:
<221> NAME/KEY: MISC_FEATURE
<222> LOCATION: (18)..(18)
<223> OTHER INFORMATION: Xaa is I, R, G, E, V, or K

<400> SEQUENCE: 187

Lys Gly Xaa Lys Pro Xaa Xaa Xaa Gln Gln Xaa Xaa Phe Tyr Met Xaa
1               5                   10                  15
```

-continued

```
Leu Xaa Gly Ile Lys Ile Val Gln Phe
        20              25

<210> SEQ ID NO 188
<211> LENGTH: 39
<212> TYPE: PRT
<213> ORGANISM: Artificial Sequence
<220> FEATURE:
<223> OTHER INFORMATION: Synthetic

<400> SEQUENCE: 188

Ser Ala Thr Ala Glu Asp Ala Leu Lys His Gly Phe Glu Val Tyr Leu
1               5                   10                  15

Leu Arg Asp Ala Val Lys Gly Ile Lys Pro Glu Met Glu Gln Gln Ala
            20                  25                  30

Leu Phe Tyr Met Lys Leu Arg
        35

<210> SEQ ID NO 189
<211> LENGTH: 39
<212> TYPE: PRT
<213> ORGANISM: Artificial Sequence
<220> FEATURE:
<223> OTHER INFORMATION: Synthetic

<400> SEQUENCE: 189

Ser Arg Thr Ala Val Asp Ala Leu Lys His Gly Phe Glu Val Tyr Leu
1               5                   10                  15

Leu Arg Asp Ala Val Lys Gly Ile Lys Pro Val Trp Glu Gln Gln Ser
            20                  25                  30

Phe Phe Tyr Met Val Leu Lys
        35

<210> SEQ ID NO 190
<211> LENGTH: 39
<212> TYPE: PRT
<213> ORGANISM: Artificial Sequence
<220> FEATURE:
<223> OTHER INFORMATION: Synthetic

<400> SEQUENCE: 190

Ser His Thr Ala Met Asp Ala Leu Lys His Gly Phe Glu Val Tyr Leu
1               5                   10                  15

Leu Arg Asp Ala Val Lys Gly Ile Lys Pro His Trp Glu Gln Gln Ser
            20                  25                  30

Phe Phe Tyr Met Leu Leu Lys
        35

<210> SEQ ID NO 191
<211> LENGTH: 39
<212> TYPE: PRT
<213> ORGANISM: Artificial Sequence
<220> FEATURE:
<223> OTHER INFORMATION: Synthetic

<400> SEQUENCE: 191

Ser Trp Thr Ala Val Asp Ala Leu Lys His Gly Phe Glu Val Tyr Leu
1               5                   10                  15

Leu Arg Asp Ala Val Lys Gly Ile Lys Pro His Met Glu Gln Gln Ser
            20                  25                  30

Phe Phe Tyr Met Met Leu Lys
        35
```

<210> SEQ ID NO 192
<211> LENGTH: 39
<212> TYPE: PRT
<213> ORGANISM: Artificial Sequence
<220> FEATURE:
<223> OTHER INFORMATION: Synthetic

<400> SEQUENCE: 192

Ser Leu Thr Ala Val Asp Ala Leu Lys His Gly Phe Glu Val Tyr Leu
1               5                   10                  15

Leu Arg Asp Ala Val Lys Gly Ile Lys Pro Lys Ile Glu Gln Gln Ser
            20                  25                  30

Phe Phe Tyr Met Met Leu Lys
        35

<210> SEQ ID NO 193
<211> LENGTH: 39
<212> TYPE: PRT
<213> ORGANISM: Artificial Sequence
<220> FEATURE:
<223> OTHER INFORMATION: Synthetic

<400> SEQUENCE: 193

Ser Arg Thr Ala Ala Asp Ala Leu Lys His Gly Phe Glu Val Tyr Leu
1               5                   10                  15

Leu Arg Asp Ala Val Lys Gly Ile Lys Pro Trp Leu Glu Gln Gln Ser
            20                  25                  30

Phe Phe Tyr Met Ala Leu Lys
        35

<210> SEQ ID NO 194
<211> LENGTH: 39
<212> TYPE: PRT
<213> ORGANISM: Artificial Sequence
<220> FEATURE:
<223> OTHER INFORMATION: Synthetic

<400> SEQUENCE: 194

Ala Phe Thr Ala Val Asp Ala Leu Lys His Gly Phe Glu Val Tyr Leu
1               5                   10                  15

Leu Arg Asp Ala Val Lys Gly Ile Lys Pro Trp Leu Glu Gln Gln Ser
            20                  25                  30

Phe Phe Tyr Met Gln Leu Lys
        35

<210> SEQ ID NO 195
<211> LENGTH: 39
<212> TYPE: PRT
<213> ORGANISM: Artificial Sequence
<220> FEATURE:
<223> OTHER INFORMATION: Synthetic

<400> SEQUENCE: 195

Ser Arg Thr Ala Val Asp Ala Leu Lys His Gly Phe Glu Val Tyr Leu
1               5                   10                  15

Leu Arg Asp Ala Val Lys Gly Ile Lys Pro Trp Leu Glu Gln Gln Ala
            20                  25                  30

Phe Phe Tyr Met Glu Leu Lys
        35

<210> SEQ ID NO 196
<211> LENGTH: 39

```
<212> TYPE: PRT
<213> ORGANISM: Artificial Sequence
<220> FEATURE:
<223> OTHER INFORMATION: Synthetic

<400> SEQUENCE: 196

Ser Arg Thr Ala Arg Asp Ala Leu Lys His Gly Phe Glu Val Tyr Leu
1               5                   10                  15

Leu Arg Asp Ala Val Lys Gly Ile Lys Pro Trp Leu Glu Gln Gln Ser
            20                  25                  30

Phe Phe Tyr Met Lys Leu Lys
            35

<210> SEQ ID NO 197
<211> LENGTH: 39
<212> TYPE: PRT
<213> ORGANISM: Artificial Sequence
<220> FEATURE:
<223> OTHER INFORMATION: Synthetic

<400> SEQUENCE: 197

Ser Val Thr Ala Leu Asp Ala Leu Lys His Gly Phe Glu Val Tyr Leu
1               5                   10                  15

Leu Arg Asp Ala Val Lys Gly Ile Lys Pro Trp Leu Glu Gln Gln Ser
            20                  25                  30

Phe Phe Tyr Met Arg Leu Lys
            35

<210> SEQ ID NO 198
<211> LENGTH: 39
<212> TYPE: PRT
<213> ORGANISM: Artificial Sequence
<220> FEATURE:
<223> OTHER INFORMATION: Synthetic

<400> SEQUENCE: 198

Ser Arg Thr Ala Met Asp Ala Leu Lys His Gly Phe Glu Val Tyr Leu
1               5                   10                  15

Leu Arg Asp Ala Val Lys Gly Ile Lys Pro Phe Leu Glu Gln Gln Ser
            20                  25                  30

Phe Phe Tyr Met Arg Leu Lys
            35

<210> SEQ ID NO 199
<211> LENGTH: 39
<212> TYPE: PRT
<213> ORGANISM: Artificial Sequence
<220> FEATURE:
<223> OTHER INFORMATION: Synthetic

<400> SEQUENCE: 199

Ser Leu Thr Ala Val Asp Ala Leu Lys His Gly Phe Glu Val Tyr Leu
1               5                   10                  15

Leu Arg Asp Ala Val Lys Gly Ile Lys Pro Trp His Glu Gln Gln Ser
            20                  25                  30

Phe Phe Tyr Met Leu Leu Lys
            35

<210> SEQ ID NO 200
<211> LENGTH: 39
<212> TYPE: PRT
<213> ORGANISM: Artificial Sequence
<220> FEATURE:
```

<223> OTHER INFORMATION: Synthetic

<400> SEQUENCE: 200

Ser His Thr Ala Val Asp Ala Leu Lys His Gly Phe Glu Val Tyr Leu
1               5                   10                  15

Leu Arg Asp Ala Val Lys Gly Ile Lys Pro Trp Leu Glu Gln Gln Ser
            20                  25                  30

Phe Phe Tyr Met Arg Leu Lys
        35

<210> SEQ ID NO 201
<211> LENGTH: 39
<212> TYPE: PRT
<213> ORGANISM: Artificial Sequence
<220> FEATURE:
<223> OTHER INFORMATION: Synthetic

<400> SEQUENCE: 201

Ser Thr Thr Ala Ile Asp Ala Leu Lys His Gly Phe Glu Val Tyr Leu
1               5                   10                  15

Leu Arg Asp Ala Val Lys Gly Ile Lys Pro Gly Met Glu Gln Gln Ser
            20                  25                  30

Phe Phe Tyr Met Ile Leu Lys
        35

<210> SEQ ID NO 202
<211> LENGTH: 39
<212> TYPE: PRT
<213> ORGANISM: Artificial Sequence
<220> FEATURE:
<223> OTHER INFORMATION: Synthetic

<400> SEQUENCE: 202

Ser Arg Thr Ala Met Asp Ala Leu Lys His Gly Phe Glu Val Tyr Leu
1               5                   10                  15

Leu Arg Asp Ala Val Lys Gly Ile Lys Pro Arg Leu Glu Gln Gln Ser
            20                  25                  30

Phe Phe Tyr Met Thr Leu Lys
        35

<210> SEQ ID NO 203
<211> LENGTH: 39
<212> TYPE: PRT
<213> ORGANISM: Artificial Sequence
<220> FEATURE:
<223> OTHER INFORMATION: Synthetic

<400> SEQUENCE: 203

Ser Met Thr Ala Met Asp Ala Leu Lys His Gly Phe Glu Val Tyr Leu
1               5                   10                  15

Leu Arg Asp Ala Val Lys Gly Ile Lys Pro Ser Leu Glu Gln Gln Ser
            20                  25                  30

Phe Phe Tyr Met Asn Leu Lys
        35

<210> SEQ ID NO 204
<211> LENGTH: 39
<212> TYPE: PRT
<213> ORGANISM: Artificial Sequence
<220> FEATURE:
<223> OTHER INFORMATION: Synthetic

<400> SEQUENCE: 204

Ser Lys Thr Ala Thr Asp Ala Leu Lys His Gly Phe Glu Val Tyr Leu
1               5                   10                  15

Leu Arg Asp Ala Val Lys Gly Ile Lys Pro Ser Leu Glu Gln Gln Ser
            20                  25                  30

Phe Phe Tyr Met Arg Leu Lys
            35

<210> SEQ ID NO 205
<211> LENGTH: 39
<212> TYPE: PRT
<213> ORGANISM: Artificial Sequence
<220> FEATURE:
<223> OTHER INFORMATION: Synthetic

<400> SEQUENCE: 205

Ser Leu Thr Ala Val Asp Ala Leu Lys His Gly Phe Glu Val Tyr Leu
1               5                   10                  15

Leu Arg Asp Ala Val Lys Gly Ile Lys Pro Met Ile Glu Gln Gln Ser
            20                  25                  30

Phe Phe Tyr Met Arg Leu Lys
            35

<210> SEQ ID NO 206
<211> LENGTH: 39
<212> TYPE: PRT
<213> ORGANISM: Artificial Sequence
<220> FEATURE:
<223> OTHER INFORMATION: Synthetic

<400> SEQUENCE: 206

Ser Trp Thr Ala Met Asp Ala Leu Lys His Gly Phe Glu Val Tyr Leu
1               5                   10                  15

Leu Arg Asp Ala Val Lys Gly Ile Lys Pro Pro Ile Glu Gln Gln Ser
            20                  25                  30

Phe Phe Tyr Met His Leu Lys
            35

<210> SEQ ID NO 207
<211> LENGTH: 39
<212> TYPE: PRT
<213> ORGANISM: Artificial Sequence
<220> FEATURE:
<223> OTHER INFORMATION: Synthetic

<400> SEQUENCE: 207

Ala Met Thr Ala Val Asp Ala Leu Lys His Gly Phe Glu Val Tyr Leu
1               5                   10                  15

Leu Arg Asp Ala Val Lys Gly Ile Lys Pro Trp Leu Glu Gln Gln Ser
            20                  25                  30

Phe Phe Tyr Met His Leu Lys
            35

<210> SEQ ID NO 208
<211> LENGTH: 39
<212> TYPE: PRT
<213> ORGANISM: Artificial Sequence
<220> FEATURE:
<223> OTHER INFORMATION: Synthetic

<400> SEQUENCE: 208

Ser Arg Thr Ala Val Asp Ala Leu Lys His Gly Phe Glu Val Tyr Leu
1               5                   10                  15

Leu Arg Asp Ala Val Lys Gly Ile Lys Pro Val Leu Glu Gln Gln Ser
            20                  25                  30

Phe Phe Tyr Met Asp Leu Lys
            35

<210> SEQ ID NO 209
<211> LENGTH: 39
<212> TYPE: PRT
<213> ORGANISM: Artificial Sequence
<220> FEATURE:
<223> OTHER INFORMATION: Synthetic

<400> SEQUENCE: 209

Ser Phe Thr Ala Ala Asp Ala Leu Lys His Gly Phe Glu Val Tyr Leu
1               5                   10                  15

Leu Arg Asp Ala Val Lys Gly Ile Lys Pro Trp Ala Glu Gln Gln Ser
            20                  25                  30

Phe Phe Tyr Met Gly Leu Lys
            35

<210> SEQ ID NO 210
<211> LENGTH: 39
<212> TYPE: PRT
<213> ORGANISM: Artificial Sequence
<220> FEATURE:
<223> OTHER INFORMATION: Synthetic

<400> SEQUENCE: 210

Ser Arg Thr Ala Met Asp Ala Leu Lys His Gly Phe Glu Val Tyr Leu
1               5                   10                  15

Leu Arg Asp Ala Val Lys Gly Ile Lys Pro Thr Glu Glu Gln Gln Ser
            20                  25                  30

Phe Phe Tyr Met Thr Leu Lys
            35

<210> SEQ ID NO 211
<211> LENGTH: 39
<212> TYPE: PRT
<213> ORGANISM: Artificial Sequence
<220> FEATURE:
<223> OTHER INFORMATION: Synthetic

<400> SEQUENCE: 211

Ser Arg Thr Ala Val Asp Ala Leu Lys His Gly Phe Glu Val Tyr Leu
1               5                   10                  15

Leu Arg Asp Ala Val Lys Gly Ile Lys Pro Thr Phe Glu Gln Gln Ser
            20                  25                  30

Phe Phe Tyr Met Ser Leu Lys
            35

<210> SEQ ID NO 212
<211> LENGTH: 39
<212> TYPE: PRT
<213> ORGANISM: Artificial Sequence
<220> FEATURE:
<223> OTHER INFORMATION: Synthetic

<400> SEQUENCE: 212

Ser Arg Thr Ala Val Asp Ala Leu Lys His Gly Phe Glu Val Tyr Leu
1               5                   10                  15

Leu Arg Asp Ala Val Lys Gly Ile Lys Pro Arg Leu Glu Gln Gln Ser
            20                  25                  30

```
Phe Phe Tyr Met Ser Leu Lys
        35

<210> SEQ ID NO 213
<211> LENGTH: 183
<212> TYPE: PRT
<213> ORGANISM: Artificial Sequence
<220> FEATURE:
<223> OTHER INFORMATION: Synthetic

<400> SEQUENCE: 213

His Met Pro Glu Glu Ala Leu Ile Val Val Asp Met Gln Arg Asp Phe
1               5                   10                  15

Met Pro Gly Gly Ala Leu Pro Val Pro Glu Gly Asp Lys Ile Ile Pro
            20                  25                  30

Lys Val Asn Glu Tyr Ile Arg Lys Phe Lys Glu Lys Gly Ala Leu Ile
        35                  40                  45

Val Ala Thr Arg Asp Trp His Pro Glu Asn His Ile Ser Phe Arg Glu
    50                  55                  60

Arg Gly Gly Pro Trp Pro Arg His Cys Val Gln Asn Thr Pro Gly Ala
65                  70                  75                  80

Glu Phe Val Val Asp Leu Pro Glu Asp Ala Val Ile Ile Ser Lys Ala
                85                  90                  95

Thr Glu Pro Asp Lys Glu Ala Tyr Ser Gly Pro Glu Gly Thr Asp Leu
            100                 105                 110

Ala Lys Ile Leu Arg Gly Asn Gly Val Lys Arg Val Tyr Ile Cys Gly
        115                 120                 125

Val Ala Thr Glu Tyr Cys Val Ser Ala Thr Ala Glu Asp Ala Leu Lys
    130                 135                 140

His Gly Pro Glu Val Tyr Leu Leu Arg Asp Ala Val Lys Gly Ile Lys
145                 150                 155                 160

Pro Glu Met Glu Gln Gln Ala Leu Phe Tyr Met Lys Leu Arg Gly Ile
                165                 170                 175

Lys Ile Val Gln Phe Leu Glu
            180
```

BINDING PROTEINS TO THE CONSTANT REGION OF IMMUNOGLOBULIN G

CROSS-REFERENCE

This application is a U.S. National Phase of International Application No. PCT/US2013/033721, filed Mar. 25, 2013, which claims priority to U.S. Provisional Application No. 61/615,642, filed Mar. 26, 2012, the disclosures of which are hereby incorporated by reference in their entireties.

STATEMENT REGARDING FEDERALLY SPONSORED RESEARCH

This invention was made with government support under grant number HDTRA1-10-1-0040 awarded by the Defense Threat Reduction Agency. The government has certain rights in the invention.

BACKGROUND

Recombinant monoclonal antibodies and Fc-fusion proteins have become an important class of biological pharmaceuticals and research reagents. Their manufacture typically involves mammalian cells as the expression host and affinity chromatography as a key purification step. While upstream processes such as cell-line development and engineering have significantly enhanced antibody yields, the downstream purification steps remain expensive and reduce productivity. The vast majority of antibody purification pipelines employ a Protein A-based purification step, which contributes to the majority of the raw-material costs[1, 2]. Antibody elution from a Protein A column is typically achieved by lowering the pH to 3. However, at such low pH, aggregation and denaturation of the antibody and of Fc-fusion proteins can easily occur.

SUMMARY OF THE INVENTION

In a first aspect, the present invention provides polypeptides comprising or consisting of an amino acid sequence of general formula 1 Z1-Z2-Z3 (SEQ ID NO: 1), wherein Z1 is a peptide with an amino acid sequence according to general formula 2: X1-S-X2 (SEQ ID NO: 2), wherein X1 is any four amino acids; and
X2 is any nine amino acids;
Z2 is a peptide of between 17 and 50 amino acid residues; and Z3 is a peptide with an amino acid amino acid sequence according to general formula 3: B1-Q-B2-F-Y-B3 (SEQ ID NO: 3)

B1 is any four amino acids;
B2 is any two amino acids; and
B3 is any four amino acids.

In one embodiment, X2 may be R-X10 (SEQ ID NO: 50), wherein X10 is any 8 amino acids. In another embodiment, X2 may be a peptide of general formula 4: R-J1-V-J2 (SEQ ID NO: 4), wherein J1 is any two amino acids; and
J2 is any five amino acids.

In one embodiment, X2 may be RTA(X3)D(A/F)(L/R/K)(K/L)H (SEQ ID NO: 5); wherein X3 is any amino acid.

In a further embodiment, B1 may be (T/S/R/M/P/W/V)(M/F)(E/M/K/L/V)(Q) (SEQ ID NO: 6). In another embodiment, B2 may be (S/A)(F/L/M/I). In a still further embodiment, B3 may be M(B4)(L/W)(R/K) (SEQ ID NO: 7), wherein B4 is any amino acid. In another embodiment, the polypeptides comprise an amino acid sequence of general formula 5, Z4-Z1-Z2-Z3 (SEQ ID NO: 8), wherein Z4 is a peptide of at least between 100-200 amino acids in length.

In another aspect, the invention provides pharmaceutical compositions comprising the polypeptide of any embodiment of the invention and a pharmaceutically acceptable carrier.

In a further aspect, the invention provides compositions, comprising the polypeptide of any embodiment of the invention bound to a solid support.

In another aspect, the present invention provides isolated nucleic acids, encoding the polypeptide of any embodiment of the invention. In a further aspect, the invention provides recombinant expression vectors comprising a nucleic acid of the invention operatively linked to a promoter. In a still further aspect, the invention provides recombinant host cells, comprising the recombinant expression vector of the invention.

In a further aspect, the invention provides methods for purifying antibodies, comprising (a) contacting a sample comprising antibodies or Fc fusion proteins with one or more polypeptides according to any embodiment of the invention under suitable conditions for binding of antibodies in the sample to the one or more polypeptides to form antibody-polypeptide complexes; and (b) dissociating the antibody from the antibody-polypeptide complexes, to isolate the antibody.

In a still further aspect, the invention provides methods for detection of an antibody in a sample, comprising (a) contacting a sample comprising antibodies or Fc fusion proteins with one or more polypeptides according to any embodiment of the invention under suitable conditions for binding of antibodies or Fc fusion protein in the sample to the one or more polypeptides to form antibody-polypeptide complexes; and (b) detecting the antibody-polypeptide complexes.

DESCRIPTION OF THE FIGURES

FIGS. 3A and B. Sequence alignments (from top to bottom (FIG. 3A) SEQ ID NOs: 188, 189, 190, 191, 192, 193, 194, 195, 196, 197, 198, 199, 199, 200, and 200; and (FIG. 3B) SEQ ID NOs: 188, 201, 202, 203, 204, 205, 206, 207, 208, 209, 210, 210, 211, and 212) of clones after 4 selections at different pH levels, showing only the sequence stretch that contained mutations from the originally designed sequence.

FIG. 4. Diversity of C-terminal interface helix (epi2 library), here residues 155-179 (SEQ ID NO: 187) are shown. Alignment contains residue combination after 3 rounds of selection, amino acid on top describe the starting diversity. Selections were done around neutral pH. These changes affect binding affinity, but unlikely affect pH sensitivity as this peptide stretch is not the helix peptide stretch next to histidine 433 of the IgG.

DETAILED DESCRIPTION OF THE INVENTION

Figure 1:
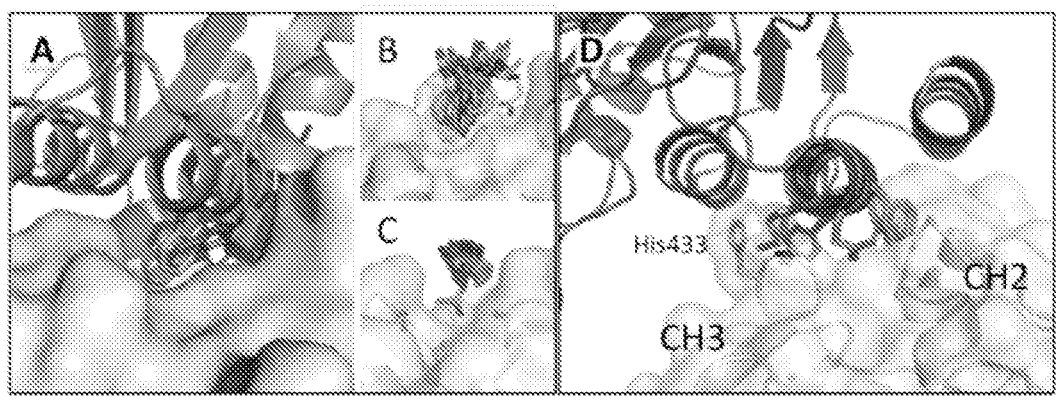
FIG. 1. Design strategy. (A) Phe14 from Protein A (pdb I.D. 116x) with Fc and comparing the binding interactions of Protein A, neonatal Fc receptor (FcRn)[19] and a synthetic peptide isolated through phage display. (B) Docked hotspots derived from Phe14. (C) Inverse rotamers of Gln11. (D) Minimized Protein A B domain called Z34C and model of FcB6 bound to the Fc region of IgG1 (based on 116x).

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2$^{nd}$ Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the present invention provides polypeptides comprising an amino acid sequence of general formula 1 Z1-Z2-Z3 (SEQ ID NO: 1), wherein Z1 is a peptide with an amino acid sequence according to general formula 2: X1-S-X2 (SEQ ID NO: 2), wherein
   X1 is any four amino acids; and
   X2 is any nine amino acids;
Z2 is a peptide of between 17 and 50 amino acid residues; and Z3 is a peptide with an amino acid amino acid sequence according to general formula 3: B1-Q-B2-F-Y-B3 (SEQ ID NO: 3)
   B1 is any four amino acids;
   B2 is any two amino acids; and
   B3 is any four amino acids.

As demonstrated herein, the inventors have computationally designed and prepared polypeptides according to the invention that bind to the Fc (Fragment, crystallizable) constant region of immunoglobulin G (IgG). The recited polypeptide serves as a module that can bind to the IgG Fc region, and thus can be combined with other polypeptide modules to carry out such binding and to add other functionality to as desired for a given purpose. The IgG Fc-binding of the polypeptides of the present invention permits the use of polypeptides of the invention, for example, as an alternative to Protein A in antibody or Fc fusion protein isolation and other assays. Furthermore, in some embodiments, the polypeptides are thermostable and can be purified through heating bacterial cells expressing them at up to 80° C. Therefore, little to no other physical or chemical step is necessary to release the polypeptides from the cells. Centrifugation eliminates cell debris and aggregates. Thus, production could be much less cumbersome and expensive compared to Protein A. The thermostability of the polypeptides likely results in a longer half-life than the conventional Protein A and possibly less proteolytic cleavage.

In one embodiment, Z1 and Z3 represent two different helices that interact with the Fc region of an IgG and are separated by spacer region Z2.

In one embodiment, the X2 is R-X10 (SEQ ID NO: 50), wherein X10 is any 8 amino acids. In this embodiment, Z1 has the sequence X1-S-R-X10 (SEQ ID NO: 9). As described in more detail in the examples that follow, this embodiment provides the added benefit of pH-dependent binding of the polypeptides of the invention to the IgG Fc region. Thus, the polypeptides bind more strongly to the IgG Fc region at one pH compared to another pH, permitting pH dependent fine control for IgG affinity purification and other uses.

In another embodiment, X2 is a peptide of general formula 4: R-J1-V-J2 (SEQ ID NO: 4), wherein
   J1 is any two amino acids; and
   J2 is any five amino acids. This embodiment provides improved pH dependent binding to the resulting polypeptides, as described in more detail in the examples that follow.

In a further embodiment, X1 is EY(A/C)V (SEQ ID NO: 10). In a still further embodiment, X2 is (R/A/T)TA(X3)DA (L/R/K/F)(K/L)(H/L) (SEQ ID NO: 11); wherein X3 is any amino acid. In other embodiments, X2 is RTA(X3)DA(R/K)KH (SEQ ID NO: 12) or RTAVDALKH (SEQ ID NO: 13). Each of these embodiments is found in specific preferred polypeptides described in the examples that follow, or is a genus of amino acid sequences found in such preferred polypeptides.

In other embodiments, Z1 is selected from the group consisting of

| | |
|---|---|
| EYCVSATAEDALKH; | (SEQ ID NO: 14) |
| EYCVSRTAVDAKKH; | (SEQ ID NO: 15) |
| EYAVSRTAVDALKH; | (SEQ ID NO: 16) |
| EYCVSRTAVDALKH; | (SEQ ID NO: 17) |

-continued

| | |
|---|---|
| EY(A/C)VSRTA(E/V/L/M/A/I/T)DALKH; | (SEQ ID NO: 18) |
| EY(A/C)VSRTA(E/V/L/R/M/A)DALKH; | (SEQ ID NO: 19) |
| EY(A/C)VSRTA(E/V/M/A/I/T)DALKH; | (SEQ ID NO: 20) |
| EY(A/C)VSRTAVDALKH; | (SEQ ID NO: 21) |
| EY(A/C)VSRTA(V/M)DALKH; | (SEQ ID NO: 22) |
| EY(A/C)VSRTAMDALKH; | (SEQ ID NO: 23) |
| EY(A/C)VSRTAADALKH; | (SEQ ID NO: 24) |
| EY(A/C)VSRTAMDALKH; | (SEQ ID NO: 25) |
| EY(A/C)VSRTALDALKH; | (SEQ ID NO: 26) |
| EY(A/C)VSRTAIDALKH; | (SEQ ID NO: 27) |
| EY(A/C)VSRTATDALKH; | (SEQ ID NO: 28) |
| EY(A/C)VSRTAVDALKH | (SEQ ID NO: 29) |
| EYAVSRTAMDALKH; | (SEQ ID NO: 30) |
| EYAVSRTAADALKH; | (SEQ ID NO: 31) |
| EYAVSRTAMDALKH; | (SEQ ID NO: 32) |
| EYAVSRTALDALKH; | (SEQ ID NO: 33) |
| EYAVSRTAIDALKH; | (SEQ ID NO: 34) |
| EYAVSRTATDALKH; | (SEQ ID NO: 35) |
| EYCVSRTAMDALKH; | (SEQ ID NO: 36) |
| EYCVSRTAADALKH; | (SEQ ID NO: 37) |
| EYCVSRTAMDALKH; | (SEQ ID NO: 38) |
| EYCVSRTALDALKH; | (SEQ ID NO: 39) |
| EYCVSRTAIDALKH; and | (SEQ ID NO: 40) |
| EYCVSRTATDALKH. | (SEQ ID NO: 41) |

Each of these embodiments represents either specific peptide domains in preferred embodiments described herein, or represents consensus sequences of such preferred embodiments. In a further preferred embodiment, Z1 is EYAVSRTAVDALKH (SEQ ID NO: 16) or EYCVSRTAVDALKH (SEQ ID NO: 17).

The polypeptides of general formula 1 as disclosed above include Z3 as a peptide with an amino acid amino acid sequence according to general formula 3: B1-Q-B2-F-Y-B3 (SEQ ID NO: 3)
 B1 is any four amino acids;
 B2 is any two amino acids; and
 B3 is any four amino acids.

In one embodiment B1 is (T/S/R/M/P/W/V/E)(M/F)(E/M/K/L/V)Q (SEQ ID NO: 42). In a further embodiment, B1 is (T/S/R/M/P/W/V)(M/F)(E/M/K/L/V)Q (SEQ ID NO: 6). In another embodiment, B1 is TFEQ (SEQ ID NO: 43). In a further embodiment, B2 is (S/A)(F/L/M/I). In a still further embodiment, B2 is selected from the group consisting of SF, SL, AF, and AL. Most preferably, B2 is SF. In another embodiment, B3 is M(B4)(L/W)(R/K) (SEQ ID NO: 7), wherein B4 is any amino acid. In one embodiment, B4 is selected from the group consisting of V, L, M, R, and K; this embodiment is preferred for pH 6.5 dependent polypeptide binders. In another embodiment, B4 is selected from the group consisting of S, T, R, K, and H, which is preferred for pH 8 dependent polypeptide binding. In another embodiment, B3 is selected from the group consisting of MSLK (SEQ ID NO: 44), MTLK (SEQ ID NO: 45) and MKLR (SEQ ID NO: 46); most preferably B3 is MSLK (SEQ ID NO: 44). Each of these embodiments represents either specific peptide domains in preferred embodiments described herein, or represents consensus sequences of such preferred embodiments.

In various further embodiments, Z3 is selected from the group consisting of:

| | |
|---|---|
| EMEQQAFFYMKLR; | (SEQ ID NO: 47) |
| EMEQQALFYMKLR; | (SEQ ID NO: 48) |
| TFEQQSFFYMSLK; | (SEQ ID NO: 49) |
| (B5)(B6)EQQ(S/A)(F/L)FYM(B7)L(K/R), | (SEQ ID NO: 51) | where B5, B6, and B7 are independently any amino acid;

| | |
|---|---|
| (G/R/S/M/P/W/V/T/R)(M/L/I/A/E/F)EQQ(S/A)(F/L)FYM(B5)L(K/R); | (SEQ ID NO: 52) |
| (V/H/K/W)(M/W/I/L/H)EQQ(S/A)(F/L)FYM(B5)L(K/R); | (SEQ ID NO: 53) |
| EMEQQALFYMKLK; | (SEQ ID NO: 54) |
| VWEQQSFFYMVLK; | (SEQ ID NO: 55) |
| HWEQQSFFYMLLK; | (SEQ ID NO: 56) |
| HMEQQSFFYMMLK; | (SEQ ID NO: 57) |
| KIEQQSFFYMMLK; | (SEQ ID NO: 58) |
| WLEQQSFFYMALK; | (SEQ ID NO: 59) |
| WLEQQSFFYMQLK; | (SEQ ID NO: 60) |
| WLEQQAFFYMELK; | (SEQ ID NO: 61) |
| WLEQQSFFYMKLK; | (SEQ ID NO: 62) |
| FLEQQSFFYMRLK; | (SEQ ID NO: 63) |
| WHEQQSFFYMMLK; | (SEQ ID NO: 64) |
| WHEQQSFFYMRLK; | (SEQ ID NO: 65) |
| EMEQQALFYMKLK; | (SEQ ID NO: 66) |
| GMEQQSFFYMILK; | (SEQ ID NO: 67) |
| RLEQQSFFYMTLK; | (SEQ ID NO: 68) |

-continued (SEQ ID NO: 69)
SLEQQSFFYMNLK;

(SEQ ID NO: 70)
MIEQQSFFYMRLK;

(SEQ ID NO: 71)
PIEQQSFFYMHLK;

(SEQ ID NO: 72)
WLEQQSFFYMHLK;

(SEQ ID NO: 73)
VLEQQSFFYMDLK;

(SEQ ID NO: 74)
WAEQQSFFYMGLK;

(SEQ ID NO: 75)
TEEQQSFFYMTLK;

(SEQ ID NO: 76)
TFEQQSFFYMSLK;

(SEQ ID NO: 77)
RLEQQSFFYMSLK;

(SEQ ID NO: 78)
EREQQSFFYMGLK;

(SEQ ID NO: 79)
EREQQSFFYMGLK;

(SEQ ID NO: 80)
HMKQQSFFYMSLR;

(SEQ ID NO: 81)
HWVQQSFFYMGLK;

(SEQ ID NO: 82)
DWVQQSMFYMELK;

(SEQ ID NO: 83)
DWVQQSLFYMNLK;
and (SEQ ID NO: 84)
EWVQQSLFYMGLK.

In the polypeptides of the invention according to general formula 1, Z2 is a peptide of between 17 and 50 amino acid residues. Z2 can be any suitable length between 17-50 amino acids (17-45, 17-40, 17-25, 17-30, 17-25, 17-20, etc.) to permit appropriate spacing between helices Z1 and Z3 for binding to IgG Fc regions. There are no specific amino acid sequence requirements in the Z2 domain, and additional peptide domains can be added within Z2 as desired for a given intended purpose. In one embodiment, Z2 is a peptide of between 17 and 32 amino acids. In one embodiment, Z2 comprises or consists of the amino acid sequence G(F/V)(E/D)(V/G)(Y/C)L(L/F)R(D/E/N)AVKG(I/V/F)KP (SEQ ID NO: 85); this embodiment is based on heat map mutational studies described in the examples that follow. In another embodiment, Z2 comprises or consists of the amino acid sequence GFEVYLLRDAVKG(I/V/F)KP (SEQ ID NO: 86). In a preferred embodiment, Z2 comprises or consists of GFEVYLLRDAVKGIKP (SEQ ID NO: 87). Each of these embodiments represents either specific peptide domains in preferred embodiments described herein, or represents consensus sequences of such preferred embodiments.

In various embodiments, the polypeptides of the invention comprise or consist of a peptide selected from the group consisting of:

(SEQ ID NO: 88)
EY(C/A)SATAEDALKHGFEVYLLRDAVKGIKPEMEQQALFYMKLR;

(SEQ ID NO: 89)
EY(C/A)SRTARDALKHGFEVYLLRDAVKGIKPWLEQQSFFYMKLK;

(SEQ ID NO: 90)
EY(C/A)SRTAVDALKHGFEVYLLRDAVKGIKPVWEQQSFFYMVLK;

(SEQ ID NO: 91)
EY(C/A)SRTAADALKHGFEVYLLRDAVKGIKPWLEQQSFFYMALK;

(SEQ ID NO: 92)
EY(C/A)SRTAVDALKHGFEVYLLRDAVKGIKPWLEQQAFFYMELK;

(SEQ ID NO: 93)
EY(C/A)SRTAMDALKHGFEVYLLRDAVKGIKPFLEQQSFFYMRLK;

(SEQ ID NO: 94)
EY(C/A)SHTAMDALKHGFEVYLLRDAVKGIKPHWEQQSFFYMLLK;

(SEQ ID NO: 95)
EY(C/A)SHTAVDALKHGFEVYLLRDAVKGIKPWLEQQSFFYMRLK;

(SEQ ID NO: 96)
EY(C/A)SHTAVDALKHGFEVYLLRDAVKGIKPWLEQQSFFYMRLK;

(SEQ ID NO: 97)
EY(C/A)SWTAVDALKHGFEVYLLRDAVKGIKPHMEQQSFFYMMLK;

(SEQ ID NO: 98)
EY(C/A)AFTAVDALKHGFEVYLLRDAVKGIKPWLEQQSFFYMQLK;

(SEQ ID NO: 99)
EY(C/A)SVTALDALKHGFEVYLLRDAVKGIKPWLEQQSFFYMRLK;

(SEQ ID NO: 100)
EY(C/A)SLTAVDALKHGFEVYLLRDAVKGIKPKIEQQSFFYMMLK;

(SEQ ID NO: 101)
EY(C/A)SLTAVDALKHGFEVYLLRDAVKGIKPWHEQQSFFYMLLK;

(SEQ ID NO: 102)
EY(C/A)SLTAVDALKHGFEVYLLRDAVKGIKPWHEQQSFFYMLLK;

(SEQ ID NO: 103)
EY(C/A)SATAEDALKHGFEVYLLRDAVKGIKPEMEQQALFYMKLR;

(SEQ ID NO: 104)
EY(C/A)SRTAVDALKHGFEVYLLRDAVKGIKPTFEQQSFFYMSLK;

(SEQ ID NO: 105)
EY(C/A)SRTAVDALKHGFEVYLLRDAVKGIKPVLEQQSFFYMDLK;

(SEQ ID NO: 106)
EY(C/A)SRTAMDALKHGFEVYLLRDAVKGIKPRLEQQSFFYMTLK;

(SEQ ID NO: 107)
EY(C/A)SRTAVDALKHGFEVYLLRDAVKGIKPRLEQQSFFYMSLK;

(SEQ ID NO: 108)
EY(C/A)SRTAMDALKHGFEVYLLRDAVKGIKPTEEQQSFFYMTLK;

(SEQ ID NO: 109)
EY(C/A)SRTAMDALKHGFEVYLLRDAVKGIKPTEEQQSFFYMTLK;

(SEQ ID NO: 110)
EY(C/A)SKTATDALKHGFEVYLLRDAVKGIKPSLEQQSFFYMRLK;

(SEQ ID NO: 111)
EY(C/A)STTAIDALKHGFEVYLLRDAVKGIKPGMEQQSFFYMILK;

(SEQ ID NO: 112)
EY(C/A)SLTAVDALKHGFEVYLLRDAVKGIKPMIEQQSFFYMRLK;

(SEQ ID NO: 113)
EY(C/A)SFTAADALKHGFEVYLLRDAVKGIKPWAEQQSFFYMGLK;

(SEQ ID NO: 114)
EY(C/A)SWTAMDALKHGFEVYLLRDAVKGIKPPIEQQSFFYMHLK;

```
                                       (SEQ ID NO: 115)
EY(C/A)SMTAMDALKHGFEVYLLRDAVKGIKPSLEQQSFFYMNLK;

(SEQ ID NO: 116)
EY(C/A)AMTAVDALKHGFEVYLLRDAVKGIKPWLEQQSFFYMHLK;

(SEQ ID NO: 117)
EYCVSRTAVDALKHGFEVYLLRDAVKGIKPTFEQQSFFYMSLK;
and (SEQ ID NO: 118)
EYAVSRTAVDALKHGFEVYLLRDAVKGIKPTFEQQSFFYMSLK.
```

Each of these embodiments represents either specific polypeptides in preferred embodiments described herein, or represents consensus sequences of such preferred embodiments. In a preferred embodiment, Z2 comprises or consists of

```
                                       (SEQ ID NO: 119)
EY(C/A)VSRTAVDALKHGFEVYLLRDAVKGIKPTFEQQSFFYMSLK;

(SEQ ID NO: 117)
EYCVSRTAVDALKHGFEVYLLRDAVKGIKPTFEQQSFFYMSLK;
or (SEQ ID NO: 118)
EYAVSRTAVDALKHGFEVYLLRDAVKGIKPTFEQQSFFYMSLK.
```

In another embodiment, the polypeptides comprise an amino acid sequence of general formula 5, Z4-Z1-Z2-Z3 (SEQ ID NO: 8), wherein Z4 is a second peptide fused to Z1-Z2-Z3 (SEQ ID NO: 1). In this embodiment, the polypeptides of the invention are incorporated into a larger protein scaffold. Such a scaffold can be of any type that does not interfere with the polypeptide's ability to bind to IgG Fc regions. As noted above, the polypeptides of the invention serve as a module that can bind to the IgG Fc region, and thus can be combined with other polypeptide modules to carry out such binding and to add other functionality to as desired for a given purpose.

It will be understood that Z4 can be of any length; this embodiment permits any added functionality to be added to the polypeptides of the invention as desired for a given purpose. In one embodiment, Z4 is at least between 100-200 amino acids in length. As described in the examples herein, the inventors used the pyrazinamidase from the hyperthermophilic organism *Pyrococcus horikoshii* as a starting point for computational design of IgG Fc binders. As will be apparent to those of skill in the art, any other suitable starting protein could have been used to design the IgG Fc binding functionalities of the polypeptides of the invention. In one exemplary embodiment, Z4 is a second polypeptide comprising or consisting of the amino acid sequence:

(SEQ ID NO: 120)
PXXXALIVIDMQNDFV(S/—)(X/—)(X/—)PGGPLXVPGG

EXIIXXINXLLXAAR(F/—)XXG(X/—)(X/—)IPVVXTRDWH(X/

—)(Q/—)PENHISFXXDXGP(K/—)(Z/—)(P/—)(X/—)(X/

—)(T/—)(X/—)(X/—)(X/—)(X/—)(X/—)(X/—)(X/—)(X/

—)(G/—)(D/—)(D/—)(S/—)(T/—)(Q/—)(E/—)(G/—)(X/

—)(L/—)WPPHXVQGXXGAELXPXL(G/—)(I/—)(F/)(Y/—)(A/)

(P/—)QEGD(X/—)(X/—)(X/—)XVIXKXFXTDXXXYSAFXG

-continued

TD(X/—)(X/—)(X/—)(X/—)(T/—)(G/—)LXXXLRERGVD

TVIVXGVAT;

wherein "X" means any amino acid and "-" means that the position may be absent.

This embodiment is based on a consensus sequence of proteins with structural similarity to *Pyrococcus horikoshii* pyrazinamidase. Several proteins with similar enzymatic functionality as the activity of the *Pyrococcus horikoshii* pyrazinamidase, have almost identical backbone structure. The sequence similarity diverges easily so that even though only 22% identity might exist, two proteins of this family have almost an identical backbone structure. Thus, a scaffold protein based on the *Pyrococcus horikoshii* pyrazinamidase can be easily replaced by one of its structural homologues.

In another embodiment, Z4 may comprise or consist of an amino acid sequence with at least 90% identity (i.e.: at least 90%, 92%, 95%, 96%, 97%, 98%, 99%, or 100% identical) to an amino acid sequence selected from the group consisting of:

>1IM5: A|PDBID|CHAIN|SEQUENCE
(SEQ ID NO: 121)
(M/)PEEALIVVDMQRDFMPGGALPVPEGDKIIPKVNEYIRKFKEKGAL
IVATRDWHPENHISFRERGGPWPRHCVQNTPGAEFVVDLPEDAVIISKA
TEPDKEAYSGFEGTDLAKILRGNGVKRVYICGVAT;

>3R2J: A|PDBID|CHAIN|SEQUENCE
(SEQ ID NO: 122)
(M/—)(A/—)(H/—)(H/—)(H/—)(H/—)
(H/—)(H—)VGTGSNDDDDKSPDPPTLCVTVSSTTDVLIIADM
QVDFLAPGGSLHVKGGEALLDGINAVSSQLPFRYQVATQDWHPENHCSF
VTHGGPWPPHCVQGSAGAQLHAGLHTQRINAVIRKGVTQQADSYSAFVE
DNGVSTGLAGLLHSIGARRV FVCGVAY;

>3EEF: A|PDBID|CHAIN|SEQUENCE
(SEQ ID NO: 123)
MKPALVVVDMVNEFIHGRLATPEAMKTVGPARKVIETFRRSGLPVVYVN
DSHYPDDPEIRIWGRHSMKGDDGSEVIDEIRPSAGDYVLEKHAYSGFYG
TNLDMILRANGIDTVVLIGLDA;

>2WTA: A|PDBID|CHAIN|SEQUENCE
(SEQ ID NO: 124)
(M/—)(G/—)(S/—)(S/—)H/—)(H/—)
(H/—)(H/—)(H/—)(H—)SSGENLYFQGHMKMNKQP
QNSALVVVDVQNGFTPGGNLAVADADTIIPTINQLAGCFENVVLTQDWH
PDNHISFAANHPGKQPFETIELDYGSQVLWPKHCIQGTHDAEFHPDLNI
PTAQLIIRKGFHAHIDSYSAFMEADHTTMTGLTG YLKERGIDTVYV
VGIAT;

>3V8E: A|PDBID|CHAIN|SEQUENCE
(SEQ ID NO: 125)
MKTLIVVDMQNDFISPLGSLTVPKGEELINPISDLMQDADRDWHRIVVT
RDWHPSRHISFAKNHKDKEPYSTYTYHSPRPGDDSTQEGILWPVHCVKN
TWGSQLVDQIMDQVVTKHIKIVDKGFLTDREYYSAFHDIWNFHKTDMNK
YLEKHHTDEVYIV GVAL;

>3O94: A|PDBID|CHAIN|SEQUENCE
(SEQ ID NO: 126)
(M/—)(G/—)(S/—)(S/—)H/—)(H/—)
(H/—)(H/—)(H/—)(H—)SSGLVPRGSHMTKALISI
DYTEDFVADSGKLTAGAPAQAISDAISKVTRLAFERGDYIFFTIDAHEE
NDCFHPESKLFPPHNLIGTSGRNLYGDLGIFYQEHGSDSRVFWMDKRHY
SAFSGTDLDIRLRERRVSTVILTGVLT;

-continued

```
>3LQY: A|PDBID|CHAIN|SEQUENCE
                                         (SEQ ID NO: 127)
GMTTENTTALLLIDFQNDYFSTYNGAKNPLVGTEAAAEQGAKLLAKFRQ
QGLPVVHVRHEFPTDEAPFFLPGSDGAKIHPSVAAQEGEAVVLKHQINS
FRDTDLKKVLDDAGIKKLVIVGAMT;

>2B34: A|PDBID|CHAIN|SEQUENCE
                                         (SEQ ID NO: 128)
MAARKLIARINPTNSALFVCDLQEKFASNIKYFPEIITTSRRLIDAARI
LSIPTIVTEQYPKGLGHTVPTLKEGLAENTPIFDKTKFSMCIPPTEDTL
KKVQNVILVGIEA;

>3OQP: A|PDBID|CHAIN|SEQUENCE
                                         (SEQ ID NO: 129)
GMTTPRRALIVIDVQNEYVTGDLPIEYPDVQSSLANIARAMDAARAAGV
PVVIVQNFAPAGSPLFARGSNGAELHPVVSERARDHYVEKSLPSAFTGT
DLAGWLAARQIDTLTVTGYMT);

>2A67: A|PDBID|CHAIN|SEQUENCE
                                         (SEQ ID NO: 130)
AMKNRALLLIDFQKGIESPTQQLYRLPAVLDKVNQRIAVYRQHHAPIIF
VQHEETELPFGSDSWQLFEKLDTQPTDFFIR KTHANAFYQTNLNDLLT
EQAVQTLEIAGVQT;

>4H17: A|PDBID|CHAIN|SEQUENCE
                                         (SEQ ID NO: 131)
GMSVPTTMFRLTGRDYPPAKLSHASLIIDAQKEYLSGPLKLSGMDEAV
ANIARLLDAARKSGRPIIHVRHLGTVGGRFDPQGPAGQFIPGLEPLEGE
IVIEKRMPNAFKNTKLHETLQELGHLDLIVCGFMS;

>3PL1: A|PDBID|CHAIN|SEQUENCE
                                         (SEQ ID NO: 132)
MRALIIVDVQNDFCEGGSLAVTGGAALARAISDYLAEAADYHHVVATKD
FHIDPGDHFSGTPDYSSSWPPHCVSGTPGADFHPSLDTSAIEAVFYKGA
YTGAYSGFEGVDENGTPLLNWLRQRGVDEVDVVGIAT;

>3MCW: A|PDBID|CHAIN|SEQUENCE
                                         (SEQ ID NO: 133)
GMPAPLRFSSDKPLLLLIDMQQAVDDPSWGPRNHPQAEQACAGLLQAWR
ARGLPLIHIRHDSVEPNSTYRPGQPGHAFKPEVEPRPGETVIAKQTNSA
FIGTGLEALLRANGWLELVVAGVST;

>1YZV: A|PDBID|CHAIN|SEQUENCE
                                         (SEQ ID NO: 134)
(M/—)(A/—)(S/—)(S/—)H/—)(H/—)
(H/—)(H/—)(H/—)(H—)MSRLLKHYGSCKTAFFCC
DIQEKFMGRIANSANCVFVANRFAGLHTALGTAHSVYIVTEQYPKGLGA
TSADI RLPPDAHVFSKKRFAMLVPQVMPLVDLPEVEQVVLWGFET;

>3IRV: A|PDBID|CHAIN|SEQUENCE
                                         (SEQ ID NO: 135)
MSLAEVNPMSKPLVRWPINPLRTAVIVVDMQKVFCEPTGALYVKSTADI
VQPIQKLLQAARAAQVMVIYLRHIVRGDGSDTGRMRDLYPNVDQILARH
DPDVEVIEALAPQSDDVIVDKLFYSGFHNTDLDTVLRARDVDTIIVCGT
VT;

>3HB7: A|PDBID|CHAIN|SEQUENCE
                                         (SEQ ID NO: 136)
YFQGMAKHAILVIDMLNDFVGEKAPLRCPGGETIIPDLQKIFEWVRGRE
GDDIHLVHIQEAHRKNDADFRVRPLHAVKGTWGSDFIPELYPQEDEYIV
QKRRHSGFAHTDLDLYLKEEGIDTVVLTGVWT;

>3KL2: A|PDBID|CHAIN|SEQUENCE
                                         (SEQ ID NO: 137)
MSLTTSKTRKSGVAMTEKLELDPARTAIVLIEYQNEFTSDGGVLHGAVA
DVMQHTGMLANTVAVVDAARQAGVPIMHAPITFAEGYGELTRHPYGILK
GVVDGKAFVKGTWGAAIVDELAPVNGDIVIEGKRGLDTFASTNLDFILR
SKGVDTIVLGGFL TNC;

>2FQ1: A|PDBID|CHAIN|SEQUENCE
                                         (SEQ ID NO: 138)
GHMAIPKLQAYALPESHDIPQNKVDWAFEPQRAALLIHDMQDYFVSFWG
ENCPMMEQVIANIAALRDYCKQHNIPVYYTAQPKEQSDEDRALLNDMWG
PGLTRSPEQQKVVDRLTPDADDTVLVKWRYSAFHRSPLEQMLKESGRNQ
LIITGVYA;
and >3TG2: A|PDBID|CHAIN|SEQUENCE
                                         (SEQ ID NO: 139)
MAIPKIASYPLPVSLPTNKVDWRIDASRAVLLIHNMQEYFVHYFDSQAE
PIPSLIKHIQQLKAHAKQAGIPVVYTAQPANQDPAERALLSDFWGPGLS
EETAIIAPLAPESGDVQLTKWRYSAFKKSPLLDWLRETGRDQLIITGV
YA.
```

Each of these embodiments represents the N-terminal portion of a specific protein with structural similarity to *Pyrococcus horikoshii* pyrazinamidase; thus, each corresponds to the region of the *Pyrococcus horikoshii* pyrazinamidase that is not needed for the IgG Fc binding function of the polypeptides of the invention, but may help to provide structural features that provide improved binding.

In one specific embodiment, Z4 comprises or consists of

```
>1IM5: A|PDBID|CHAIN|SEQUENCE
                                         (SEQ ID NO: 140)
PEEALIVVDMQRDFMPGGALPVPEGDKIIPKVNEYIRKFKEKGALIVA

TRDWHPENHISFRERGGPWPRHCVQNTPGAEFVVDLPEDAVIISK

ATEPDKEAYSGFEGTDLAKILRGNGVKRVYICGVAT.
```

In another embodiment, the polypeptides of the invention comprise or consist of a polypeptide with an amino acid sequence with at least 90% identity (i.e.: at least 90%, 92%, 95%, 96%, 97%, 98%, 99%, or 100% identical) to an amino acid sequence selected from the group consisting of:

```
Original computationally designed sequence:
                                         (SEQ ID NO: 141)
PEEALIVVDMQRDFMPGGALPVPEGDKIIPKVNEYIRKFKEKGALIVAT
RDWHPENHISFRERGGPWPRHCVQNTPGAEFVVDLPEDAVIISKATEPD
KEAYSGFEGTDLAKILRGNGVKRVYICGVATEYCVSATAEDALKHGFEV
YLLRDAVKGIKPEMEQQAFFYMKLRGIKIVQF;

Sequence of best binder from round 2: FcB6.cons1:
                                         (SEQ ID NO: 142)
PEEALIVVDMQRDFMPGGALPVPEGDKIIPKVNEYIRKFKEKGALIVAT
RDWHPENHISFRERGGPWPRHCVQNTPGAEFVVDLPEDAVIISKATEPD
KEAYSGFEGTDLAKILRGNGVKRVYICGVATEYCVSRTAVDAKKHGFEV
LLRDAVKGIKPEMEQQALFYMKLRGIKIVQF;

Sequence of FcB6.1
                                         (SEQ ID NO: 143)
PEEALIVVDMQRDFMPGGALPVPEGDKIIPKVNEYIRKFKEKGALIVAT
RDWHPENHISFRERGGPWPRHCVQNTPGAEFVVDLPEDAVIISKATEPD
KEAYSGFEGTDLAKILRGNGVKRVYICGVATEYCVSRTAVDALKHGFEV
YLLRDAVKGIKPTFEQQSFFYMSLKGIKIVQF;

Cysteine knock-out version of the enzyme FcB6.1
                                         (SEQ ID NO: 144)
PEEALIVVDMQRDFMPGGALPVPEGDKIIPKVNEYIRKFKEKGALIVAT
RDWHPENHISFRERGGPWPRHCVQNTPGAEFVVDLPEDAVIISKATEPD
KEAYSGFEGTDLAKILRGNGVKRVYICGVATEYAVSRTAVDALKHGFEV
YLLRDAVKGIKPTFEQQSFFYMSLKGIKIVQF;
```

Full-Length Variants Selected for Binding at pH 6.5:

```
focusedLib-S4-10
                                         (SEQ ID NO: 145)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSVTALDALKHGFEVYLL
RDAVKGIKPWLEQQSFFYMRLKGIKIVQF;
``` focusedLib-S4-11
(SEQ ID NO: 146)
PEEALIVVDMQRDFMPGGALPVPEGDKIIPKVNEYIRKFKEKGALIVATR
DWHPENHISFRERGSPWPRHCVQNTPGAEFVVDLPEDAVIISKATEPDKE
AYSGFEGTDLAKILRGNGVKRVYICGVATEYCVSRTAADALKHGFEVYLL
RDAVKGIKPWLEQQSFFYMALKGIKIVQF;

focusedLib-S4-12
(SEQ ID NO: 147)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAVDALKHGFEVYLL
RDAVKGIKPVWEQQSFFYMVLKGIKIVQF;

focusedLib-S4-13
(SEQ ID NO: 148)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSLTAVDALKHGFEVYLL
RDAVKGIKPWHEQQSFFYMLLKGIKIVQF;

focusedLib-S4-15
(SEQ ID NO: 149)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSHTAMDALKHGFEVYLL
RDAVKGIKPHWEQQSFFYMLLKGIKIVQF;

focusedLib-S4-16
(SEQ ID NO: 150)
PEEALIVVDMQRDFMPGGALPVPEGDKIIPKVNEYIRKFKEKGALIVATR
DWHPENHISFRERGGPWPRHCVQNTPGAEFVVDLPEDAVIIPKATEPDKE
AYSGFEGTDLAKILRGNGVKRVYICGVATEYCVSLTAVDALKHGFEVYLL
RDAVKGIKPKIEQQSFFYMMLKGIKIVQF;

focusedLib-S4-2
(SEQ ID NO: 151)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAMDALKHGFEVYLL
RDAVKGIKPFLEQQSFFYMRLKGIKIVQF;

focusedLib-S4-3
(SEQ ID NO: 152)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSHTAVDALKHGFEVYLL
RDAVKGIKPWLEQQSFFYMRLKGIKIVQF;

focusedLib-S4-4
(SEQ ID NO: 153)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSWTAVDALKHGFEVYLL
RDAVKGIKPHMEQQSFFYMMLKGIKIVQF;

focusedLib-S4-5
(SEQ ID NO: 154)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAVDALKHGFEVYLL
RDAVKGIKPWLEQQAFFYMELKGIKIVQF;

focusedLib-S4-6
(SEQ ID NO: 155)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTARDALKHGFEVYLL
RDAVKGIKPWLEQQSFFYMKLKGIKIVQF;

focusedLib-S4-7
(SEQ ID NO: 156)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVAFTAVDALKHGFEVYLL
RDAVKGIKPWLEQQSFFYMQLKGIKIVQF;

focusedLib-S4-8
(SEQ ID NO: 157)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSLTAVDALKHGFEVYLL
RDAVKGIKPWHEQQSFFYMLLKGIKIVQF;

focusedLib-S4-9
(SEQ ID NO: 158)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSHTAVDALKHGFEVYLL
RDAVKGIKPWLEQQSFFYMRLKGIKIVQF;

Full-Length Variants Selected for Binding at pH 8 focusedLib-S4-35
(SEQ ID NO: 159)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSWTAMDALKHGFEVYLL
RDAVKGIKPPIEQQSFFYMHLKGIKIVQF;

focusedLib-S4-36
(SEQ ID NO: 160)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSFTAADALKHGFEVYLL
RDAVKGIKPWAEQQSFFYMGLKGIKIVQF;

focusedLib-S4-37
(SEQ ID NO: 161)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAVDALKHGFEVYLL
RDAVKGIKPVLEQQSFFYMDLKGIKIVQF;

focusedLib-S4-38
(SEQ ID NO: 162)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAMDALKHGFEVYLL
RDAVKGIKPRLEQQSFFYMTLKGIKIVQF;

focusedLib-S4-39
(SEQ ID NO: 163)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSTTAIDALKHGFEVYLL
RDAVKGIKPGMEQQSFFYMILKGIKIVQF;

focusedLib-S4-40
(SEQ ID NO: 164)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSLTAVDALKHGFEVYLL
RDAVKGIKPMIEQQSFFYMRLKGIKIVQF;

focusedLib-S4-42
(SEQ ID NO: 165)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSKTATDALKHGFEVYLL
RDAVKGIKPSLEQQSFFYMRLKGIKIVQF;

focusedLib-S4-43
(SEQ ID NO: 166)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAVDALKHGFEVYLL
RDAVKGIKPRLEQQSFFYMSLKGIKIVQF;

focusedLib-S4-44
(SEQ ID NO: 167)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSMTAMDALKHGFEVYLL
RDAVKGIKPSLEQQSFFYMNLKGIKIVQF;

focusedLib-S4-45
(SEQ ID NO: 168)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAMDALKHGFEVYLL
RDAVKGIKPTEEQQSFFYMTLKGIKIVQF;

focusedLib-S4-46
(SEQ ID NO: 169)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVAMTAVDALKHGFEVYLL
RDAVKGIKPWLEQQSFFYMHLKGIKIVQF;

focusedLib-S4-47
(SEQ ID NO: 170)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAVDALKHGFEVYLL
RDAVKGIKPTFEQQSFFYMSLKGIKIVQF;

focusedLib-S4-48
(SEQ ID NO: 171)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAMDALKHGFEVYLL
RDAVKGIKPTEEQQSFFYMTLKGIKIVQF.;

(SEQ ID NO: 172)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKP EREQQSFFYMGLKGIKIVQF;

(SEQ ID NO: 173)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKP EREQQSFFYMGLKGIKIVQF;

(SEQ ID NO: 174)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKPHMKQQSFFYMSLR GIKIVQF;

(SEQ ID NO: 175)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKPHWVQQSFFYMGLK GIKIVQF;

(SEQ ID NO: 176)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKPDWVQQSMFYMELK GIKIVQF;

(SEQ ID NO: 177)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKPDWVQQSLFYMNLK GIKIVQF;
and (SEQ ID NO: 178)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKPEWVQQSLFYMGLK GIKIVQF;

FcB6
(SEQ ID NO: 179)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSATAEDALKHGFEVYLL
RDAVKGIKPEMEQQAFFYMKLRGIKIVQ;

FcB6.VV
(SEQ ID NO: 180)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSVTAVDALKHGFEVYLL
RDAVKGIKPEMEQQALFYMKLRGIKIVQF;

FcB6.TV
(SEQ ID NO: 181)
PEEALIVVDMQRDFMPGGALPVPEGDKIIPKVNEYIRKFKEKGALIVVTR
EWHPENHISFRERGGPWPRHCVQNTPGAEFVVDLPEDAVIISKATEPDKE
AYSGFEGTDLAKILRGNGVKRVYICGVATEYCVSTTAVDALKHGFEVYLL
RDAVKGIKPEMEQQALFYMKLRGIKIVQF;
and FcB6.Cons2
(SEQ ID NO: 182)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSRTAVDARKHGFEVYLL
RDAVKGIKPEMEQQALFYMKLRGIKIVQF.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed.

In a further embodiment, the polypeptides of any embodiment of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used, for example, in detection and/or analytical and/or diagnostic assays. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The specific tag used will depend on the specific detection/analysis/diagnosis techniques and/or methods used such as flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. The polypeptides of the invention can be fused to marker sequences to facilitate purification. Examples include, but are not limited to, the hexa-histidine tag, the myc tag or the flag tag.

In one embodiment, one or more polypeptides of any embodiment or combination of embodiments of the invention can be bound to a solid support. Such solid supports might be porous or nonporous, planar or nonplanar and include, but are not limited to, glass, cellulose, polyacrylamide, nylon, polystyrene, polyvinyl chloride or polypropylene supports. The polypeptides can also, for example, usefully be conjugated to filtration media, such as NHS-, CNBr-, epoxy- or iodoacetyl-activated Sepharose or agarose for purposes of affinity chromatography. They can also usefully be attached to paramagnetic microspheres, typically by biotin-streptavidin interaction, or to microtiter plates.

This embodiment provides a general device for instant tethering of any antibody or Fc fusion protein to a solid surface of choice.

In another aspect, the present invention provides pharmaceutical compositions, comprising one or more polypeptides of the invention and a pharmaceutically acceptable carrier. In this embodiment, the polypeptides of the invention may be used as a drug delivery device. The polypeptides of the invention can be conjugated to a specific cargo such as a therapeutic antibody targeting a specific surface receptor, or a therapeutic moiety bound to a targeting antibody (i.e.: where the antibody is provided to target a cell receptor to which the therapeutic moiety is bound). In one non-limiting embodiment, upon endocytosis and pH drop, the polypeptide could release the antibody and can be taken up by the cell whereas the antibody can remain bound to the receptor and will eventually be recycled and surface applied again. Conjugation methods for attaching to antigens and polypeptide are well known in the art and include, but are not limited to, the use of cross-linking agents.

The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

In a further aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a still further aspect, the present invention provides host cells that have been transfected with the recombinant expression vectors disclosed herein, wherein the host cells can be either prokaryotic (such as bacteria) or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered, for example, by heating bacterial cells expressing them to approximately up to 80° C. Therefore, little to no other physical or chemical step is necessary to release the polypeptides from the cells. Centrifugation eliminates cell debris and aggregates.

In another aspect, the invention provide methods for purifying antibodies or Fc fusion proteins, comprising (a) contacting a sample comprising antibodies or Fc fusion proteins with one or more polypeptides according to any embodiment of the present invention under suitable conditions for binding of antibodies or Fc fusion protein in the sample to the one or more polypeptides to form antibody-polypeptide complexes; and (b) dissociating the antibody or Fc fusion protein from the antibody-polypeptide or Fc fusion-polypeptide complexes, to isolate the antibody.

The methods of the invention permit improved methods for antibody purification, that do not require the use of Protein A and elution protocols that require lowering the pH to 3, which can lead to aggregation and denaturation of the antibody and of Fc-fusion proteins. For example, the inventors have developed polypeptides that bind strongly to IgG Fc regions at pH 8.0 and much more weakly at pH 5.5. Thus, the binding conditions can comprise, for example contacting the sample comprising antibodies or Fc fusion proteins with the one or more polypeptides at a pH 8, and the conditions for dissociating the antibody from the antibody-polypeptide complexes can comprise dissociating at a pH of about 5.5.

Other suitable conditions to promote binding of antibodies in the sample to one or more polypeptide of the invention can be determined by those of skill in the art, based on the teachings herein. The polypeptides of the invention for use in this aspect may comprise a conjugate as disclosed above, to provide a tag useful for any detection technique suitable for a given assay. Any such tag used will depend on the specific detection/analysis/diagnosis techniques and/or methods used, as discussed above. The methods may be carried in solution, or the polypeptide(s) of the invention may be bound or attached to a solid surface, as discussed above. Based on the teachings herein, it is within the level of skill in the art to determine specific conditions for the various types of diagnostic assays disclosed in this aspect of the invention.

The methods can be used to isolate any antibody (IgG) or Fc fusion proteins of interest, including, but not limited to human IgG1, IgG2 and IgG4, mouse IgG1 and IgG2. As used herein, "antibodies include antibodies fused to any protein or peptide of interest. Any suitable sample that contains antibodies or Fc fusion proteins may be used.

The methods can be used to isolate any antibody or Fc fusion proteins, including but not limited to large scale production/isolation of therapeutic/diagnostic monoclonal antibodies. Similarly, the methods may be used in any type of assay in which isolation of antibodies is desirable, including but not limited to affinity purification of antibodies in large or small scale, Western blot analysis, enzyme linked immunosorbent assays (ELISA), immunohistochemistry (IHC) and other immunoassay protocols, such as immunoprecipitations, where the polypeptides of the invention may be immobilized to a solid surface (such as beads).

In another aspect the present invention comprises methods for detection of an antibody in a sample, comprising (a) contacting a sample comprising antibodies or Fc fusion proteins with one or more polypeptides according to any embodiment of the present invention under suitable conditions for binding of antibodies or Fc fusion protein in the sample to the one or more polypeptides to form antibody-polypeptide complexes; and (b) detecting the antibody-polypeptide complexes.

This aspect of the invention can be used in any assay where detection of an antibody in a sample is desirable, whether antibody detection is the primary goal of the assay, or where the antibody to be detected is a marker for a protein of interest in the sample. Any suitable sample that may contain the antibody to be detected can be used, including but not limited to clinical samples (blood, plasma, serum, urine, semen, tissue samples, tissue sections, ascites fluid etc.), environmental samples, experimental samples (i.e.: research laboratory use), etc.

The inventors have developed polypeptides that bind strongly to IgG Fc regions at pH 8.0 and much more weakly at pH 5.5, as well as they developed IgG Fc binders that bind less pH sensitive. Thus, for the pH sensitive binder, binding conditions can comprise, for example contacting the sample comprising antibodies or Fc fusion proteins with one or more polypeptides at a pH 8, and the conditions for dissociating the antibody from the antibody-polypeptide complexes can comprise dissociating at a pH of about 5.5. Other suitable conditions to promote binding of antibodies in the sample to one or more polypeptide of the invention can be determined by those of skill in the art, based on the teachings herein. In one embodiment, wash steps are included to facilitate removal of unbound antibody prior to detection.

The polypeptides of the invention for use in this aspect may comprise a conjugate as disclosed above, to provide a tag useful for any detection technique suitable for a given assay. Any such tag used will depend on the specific detection/analysis/diagnosis techniques and/or methods used, as discussed above. The methods may be carried in solution, or the polypeptide(s) of the invention may be bound or attached to a solid surface, as discussed above. In one embodiment, one or more polypeptides of any embodiment or combination of embodiments of the invention can be bound to a solid support. Such solid supports might be porous or nonporous, planar or nonplanar and include, but are not limited to, glass, latex, cellulose, polyacrylamide, nylon, polystyrene, polyvinyl chloride or polypropylene supports. The polypeptides can also, for example, usefully be conjugated to filtration media, such as NHS-, CNBr-, epoxy- or iodoacetyl-activated Sepharose or agarose for purposes of affinity chromatography. They can also usefully be attached to paramagnetic microspheres, typically by biotin-streptavidin interaction, or to microtiter plates or beads made of material listed above. This embodiment provides a general device for instant tethering of any antibody or Fc fusion protein to a solid surface of choice.

Based on the teachings herein, it is within the level of skill in the art to determine specific conditions for the various types of diagnostic/detection assays disclosed in this aspect of the invention. Detection of immunocomplex formation can be accomplished by standard detection techniques, such as but not limited to standard techniques used to detect fluorescent dyes, enzymes, biotin, colloidal gold or radioactive iodine conjugated to the one or more polypeptides.

In another aspect, the present invention provides methods for drug delivery comprising administering to a subject in need thereof a therapeutically effective amount of a pharmaceutical composition comprising one or more polypeptides of the invention conjugated to a therapeutic antibody to treat a disorder that the subject suffers from. As discussed above, the polypeptides of the invention can act as drug carriers. For example, the polypeptides of the invention can be conjugated to a specific cargo such as a therapeutic antibody targeting a specific surface receptor, or a therapeutic moiety bound to a targeting antibody (i.e.: where the antibody is provided to target a cell receptor to which the therapeutic moiety is bound). In one non-limiting embodiment, upon endocytosis and pH drop, the polypeptide could release the antibody and can be taken up by the cell whereas the antibody can remain bound to the receptor and will eventually be recycled and surface applied again.

As used herein, a "therapeutically effective amount" refers to an amount of the therapeutic antibody or moiety that is effective for treating the disorder in the subject. The pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Dosage regimens can be adjusted to provide the optimum desired response (e.g., a therapeutic or prophylactic response). A suitable dosage range and treatment regimen can be determined by an attending physician.

EXAMPLES

Recombinant monoclonal antibodies and Fc-fusion proteins have become an important class of biological pharmaceuticals and research reagents. Their manufacture typically involves mammalian cells as the expression host and affinity chromatography as a key purification step. While upstream processes such as cell-line development and engineering have significantly enhanced antibody yields, the downstream purification steps remain expensive and reduce productivity. The vast majority of antibody purification pipelines employ a Protein A-based purification step, which contributes to the majority of the raw-material costs[1, 2]. Protein A is used in the manufacture of monoclonal antibodies, one of the fastest growing classes of drugs. The annual revenue of therapeutic antibodies is approximately $44 billion (2011) with expected growth. The vast majority of them are purified through a Protein A column, which contributes to about 35% of the raw cost of the antibodies. Antibody elution from a Protein A column is typically achieved by lowering the pH to 3. However, at such low pH, aggregation and denaturation of the antibody and of Fc-fusion proteins can easily occur.

pH-dependent binding occurs if protonation of an ionizable residue, such as histidine, shifts the binding equilibrium. Previous efforts to engineer highly pH-dependent protein switches have focused on either the rational introduction of ionizable groups at the interface, often compromising affinity at permissive pH or relied on histidine scanning mutagenesis[3].

Computational de novo interface design potentially provides a new way to address this challenge, by focusing design of binding to sites on the target protein that contain ionizable groups. Our recently reported hot-spot-based design strategy starts by computing an idealized core interaction site (hotspot) and then scans a large set of scaffold proteins for surfaces that can present the hotspot and form stabilizing interactions with the target site[4]. Here, we describe the adaption of this methodology to develop a highly pH sensitive binding protein.

We set out to design an Fc binding protein that buries the consensus binding site on Fc and aimed to bury one of the solvent-exposed histidine residues on Fc, assuming that interactions targeting this site would show large pH sensitivity close to physiological relevant levels. The materials and methods used are described below.

We applied hotspot-guided protein interface design[4, 5], using residue interactions from Protein A as binding hotspots[6], and aimed to generate additional interactions with and around His433 or His310 to achieve pH-dependent binding. We start by generating ensembles of disembodied interaction hotspot residues Gln11, Phe14, and Leu18 from minimized Protein A[6] (FIG. 1A-C), and searched for protein structures that could harbor a combination of these sidechains while focusing on protein scaffolds of solved structure with high expression and solubility.

17 designed proteins were expressed on the surface of yeast and binding was assessed by flow cytometry following incubation with 700 nM biotinylated human IgG1 (Rituximab) that had been fluorescently labeled and oligomerized through binding to streptavidin-phycoerythrin (SAPE). 10 designs had detectable binding signals. We decided to focus on the binder codenamed FcB6 which showed the strongest signal, and which was designed to hydrogen bond to both Asn434 and His433, and was thereby an excellent candidate to optimize for pH-dependent binding.

Herein we disclose novel protein variants that bind to the constant region of IgG antibodies (Fc) and methods for designing them. These variants can be used for the purification of a variety of antibodies and their fusions, and thereby could replace or supplant the role of Protein A. The new Fc binding proteins have been designed de novo. About 850 protein scaffolds were computationally screened and designed for binding to the constant region of an IgG. Several rounds of directed evolution were performed to improve the binding behavior, to optimize affinity and pH dependence.

The originally computationally designed sequence, starting with a *Pyrococcus horikoshii* pyrazinamidase, is as follows:

```
FcB6
                                       (SEQ ID NO: 179)
PEEALIVVDMQRDFMPGGALPVPEGDKIIPKVNEYIRKFKEKGALIVATR
DWHPENHI SFRERGGPWPRHCVQNTPGAEFVVDLPEDAVIISKATEPDK
EAYSGFEGTDLAKILRGNGVKRVYICGVATEYCVSATAEDALKHGFEVYL
LRDAVKGIKPEMEQQAFFYMKLRGIKIVQ
```

Subsequent sequence alignment that resulted from various diversification and selections refer back to this sequence. After a first round of optimization ("error prone PCR based mutagenesis), binding affinity improvement was observed as shown in FIG. 2. The top 2 enhanced sequences that came out of the error prone PCR based mutagenesis round are shown below:

```
FcB6.VV
                                       (SEQ ID NO: 180)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVSVTAVDALKHGFEVYLL
RDAVKGIKPEMEQQALFYMKLRGIKIVQF;
and FcB6.TV
                                       (SEQ ID NO: 181)
PEEALIVVDMQRDFMPGGALPVPEGDKIIPKVNEYIRKFKEKGALIVVTR
EWHPENHISFRERGGPWPRHCVQNTPGAEFVVDLPEDAVIISKATEPDKE
```

-continued
AYSGFEGTDLAKILRGNGVKRVYICGVATEYCVSTTAVDALKHGFEVYLL
RDAVKGIKPEMEQQALFYMKLRGIKIVQF.

Figure 2:
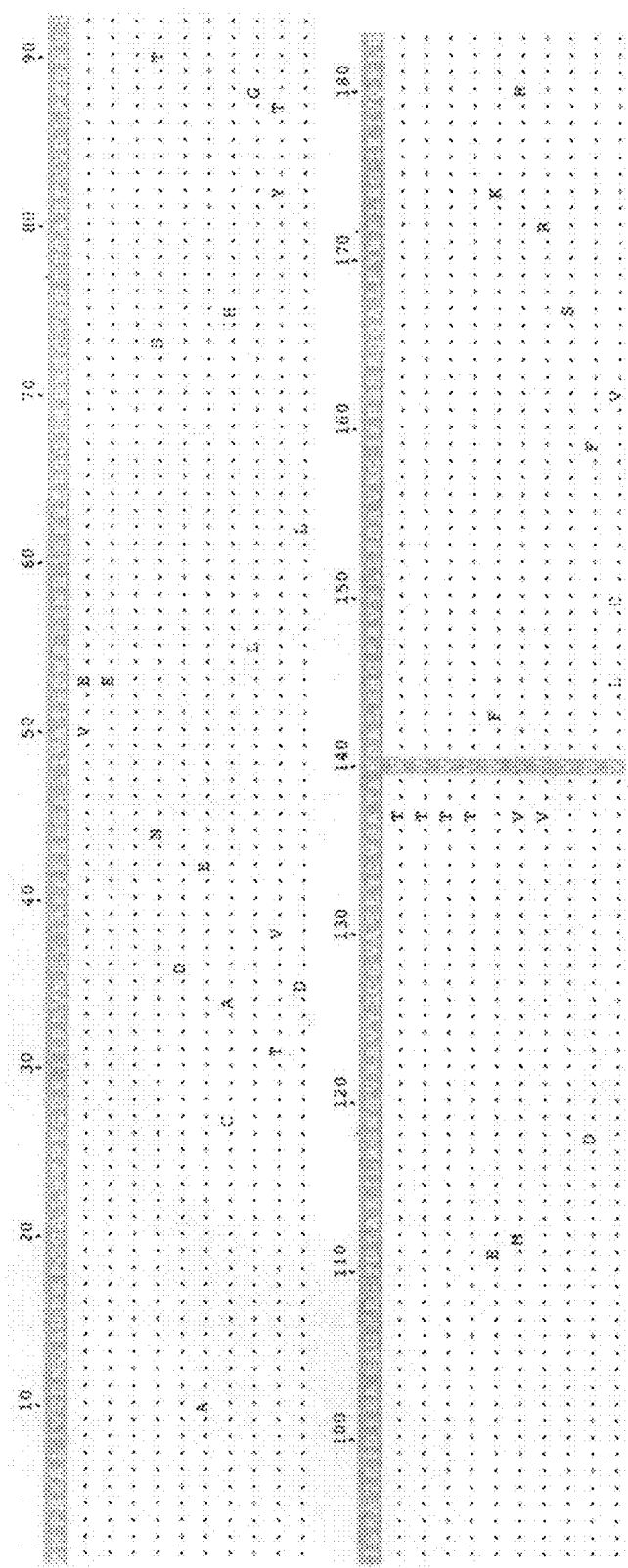
FIG. 2. Summary of the first round of affinity improvement; sequence alignment after 3 selections (SEQ ID NO: 213). Sequence contains HM at the N-terminus and LE at the C-terminus which were part of the cloning sites.

The consensus sequence for the error prone PCR based mutagenesis study indicated that positions A135 and E138 were clearly not ideal for the binding to IgG (see alignment, FIG. 2). Hence, we sampled all position for these two positions as well as position 141 and screened this new library, referred to as "consensus" library, by yeast surface display for better binding ("consensus mutagenesis screen"). We discovered that when alanine 135 was allowed to change into all possible amino acids, it preferred to become an arginine. We confirmed again that changing glutamate 138 to valine greatly improves binding affinity. Additionally, L141 could be either a lysine or arginine, with lysine resulting in a better binding.
Top Binders from the Consensus Library:
A135R, E138V and L141K or L141R
Complete Sequences:

FcB6.Cons1
(SEQ ID NO: 142)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVS<u>R</u>TA<u>V</u>DA<u>K</u>KHGFEVYLL
RDAVKGIKPEMEQQALFYMKLRGIKIVQF;
and FcB6.Cons2
(SEQ ID NO: 182)
PEEALIVVDMQRDFMPGGALPVPEGDKIIPKVNEYIRKFKEKGALIVATR
DWHPENHISFRERGGPWPRHCVQNTPGAEFVVDLPEDAVIISKATEPDKE
AYSGFEGTDLAKILRGNGVKRVYICGVATEYCVS<u>R</u>TA<u>V</u>DA<u>R</u>KHGFEVYLL
RDAVKGIKPEMEQQALFYMKLRGIKIVQF.

We next sought to improve binding affinity while optimizing pH dependent binding (pH focused screen"). For optimization of pH dependence, positions within FcB6 that are close to histidine 433 of the binding partner IgG were allowed to vary, this included also maximal variations of the suboptimal positions A135 and E138. The objective was to identify variants that would have different affinities for Fc at different pH levels. The purpose of this will be that the bound antibody or Fc fusion protein could then be easily eluted with small variation of the pH value. Hence the objective of the selection of this library was to identify binders that would bind tight at one pH level, but a lot weaker at others. Sequence alignments for well binding clones at indicated pH levels using a PBS buffer are shown below: Sequences resulting from the yeast surface display selection at pH 6.5 are shown in FIG. 3A and at pH 8 are shown in FIG. 3B.

We then determined the Kd of exemplary isolated clones for IgG at different pHs. Measurements were taken via titrations of biotinylated Rituxan (Rituximab) using yeast surface display as discussed in the materials and methods sections. These studies showed that, on average, variants that were isolated at pH 8 did not have optimized binding at pH 6.5, whereas isolates from the lower pH selections (at pH 6.5) tend to bind similarly at either pH. When comparing sequences between the two selection trajectories at the two different pH levels, we quickly could identify clones with different sequence profiles. From the pH 8 screen, we isolated various clones that had several fold poorer binding affinity at pH 6.5 compared to pH 8. Hence, we achieved our objective to identify variants that would have different affinity for the Fc domain at different pH levels. One exemplary clone (FcB6.1) had reasonable affinity (around 2 nM using this assay) and 6-7 fold worse affinity at pH 6.5, and was further characterized.

Our designed protein (FcB6) and its variants are modeled to bind to the consensus region between the CH2 and CH3 domain of the Fc region of IgGs (FIG. 1) and to parts of the CH2 domain that contains histidine 433 and asparagine 434. The computational designed protein uses various residues on a helical structure to bind to the cleft between those two domains, to which other native proteins, such as Protein A, neonatal receptor (FcRn) or the rheumatoid factor bind to. Within this helix sequence (Z3), it uses a glutamine residue to hydrogen bond to the backbone atoms of residue leu251, ile253 and asn434 of the IgG, which are located within the cleft between CH2 and CH3. FcB6 is designed to place a phenylalanine (F167) behind a loop containing the surface exposed Ile253 on the Fc domain. This phenylalanine provides not only van der Waals contact to nearby residues, it also electrostatically favorably interacts with a local helix dipole below the isoleucine-253-containing loop on the IgG. Additionally, FcB6 uses a tyrosine to wedge against the loop that contains histidine 433 at its midpoint. These core residues, next to leu171 (which is slightly less conserved), are highly conserved within FcB6 throughout several selections schemes.

Next to binding to the consensus site, the computational design FcB6, as modeled, provides many new binding contacts to CH2 through a second alpha helix (Z1) that covers the area around histidine 433, which allows for the optimization of pH dependent binding. A very crucial contact is Ser134 of the design, which introduces a buried hydrogen bond to the histidine 433 of Fc. The mutation E138V (as identified through selections) allows to shield-off the solvent from one side, strengthening thereby this hydrogen bond, because exchanges with water molecules become less likely. It also does not have a charge which could interfere with the surface charge on the IgG. The V-shaped valine residue at position 138 fits perfectly next to the above-described tyrosine 168 to encompass the histidine. Other residues are capable of shielding the histidine from the solvent, as selections also indicate, however the valine residue has the best fit and is thereby preferred. Selections also demonstrated that A138, which is located almost above histidine 433, but spatially next to the valine 138 (former E138) when facing the interface with Fc—is preferentially an arginine. The long side chain of the arginine introduces a large area for van der Waals contacts with the histidine, and the positive charge interacts highly beneficially with the negative surface charge of the epitope on Fc. However, as soon as the histidine 433 residues becomes protonated, which happens when lowering the pH level (<~6.5), it also becomes positively charged, thereby introducing a repulsion between arginine 135 of the design and the now also positively charged histidine. Additionally, the hydrogen bond with serine 134 and the histidine is not possible anymore due to the protonation, which further weakens overall the interaction between IgG and the design, thus making it highly pH sensitive.

Alternatively, mutations at 135 that cover the histidine, but do not have a charge, result in improvements of the binding affinity due to a larger contact area and they can still render the interaction slightly pH sensitive, as the buried hydrogen bond with serine 134 will be still dependent on the protonation state of the histidine 433. Hence interaction that cover and contact the histidine will still produce reasonable binding to the IgG, but with less pH sensitivity.

We also performed deep sequencing analysis of mutagenized and selected clones after mild selection conditions to figure out tolerated residues at different positions. These studies showed that Z2 (as defined above) can be modified as follows:

(SEQ ID NO: 85)
G(F/V)(E/D)(V/G)(Y/C)L(L/F)R(D/E/N)AVKG(I/V/F)KP

The most interesting polypeptides obtained from the pH focused screen are shown below. The binding constant for FcB6.1 was measured to be 33 nM at pH 8 and >1 µM at pH 5.5.

Sequence of FcB6.1
(SEQ ID NO: 143)
PEEALIVVDMQRDFMPGGALPVPEGDKIIPKVNEYIRKFKEKGALIVATR

DWHPENHISFRERGGPWPRHCVQNTPGAEFVVDLPEDAVIISKATEPDKE

AYSGFEGTDLAKILRGNGVKRVYICGVATEYCVSRTAVDALKHGFEVYLL

RDAVKGIKPTFEQQSFFYMSLKGIKIVQF

And a cysteine knock-out version of the polypeptide:

(SEQ ID NO: 144)
PEEALIVVDMQRDFMPGGALPVPEGDKIIPKVNEYIRKFKEKGALIVATR

DWHPENHISFRERGGPWPRHCVQNTPGAEFVVDLPEDAVIISKATEPDKE

AYSGFEGTDLAKILRGNGVKRVYICGVATEYAVSRTAVDALKHGFEVYLL

RDAVKGIKPTFEQQSFFYMSLKGIKIVQF.

Both Protein A and FcB6 present a helix for binding between the CH2 and CH3 domain, and the core interface residues Q164, F167, Y168, M161 and L171 present the same contacts with Fc (FIG. 1D). However, no other amino acid is identical, and FcB6 differs substantially in binding mode from Protein A as most of its additional contacts are with the CH3 domain of Fc and not with CH2. The wild-type protein on which FcB6 is based on the structure of pyrazinamidase of Pyrococcus horikoshii[7], and is completely inert to Fc suggesting that the designed surface mediates binding. Further competition with Protein A completely inhibited binding of FcB6 to the IgG1 Rituxan, indicating that it was indeed binding to the same consensus epitope.

To confirm the designed binding mode and identify possible avenues for improving the computationally designed sequence, we used PCR mutagenesis in concert with one round of fluorescent-activated cell sorting (FACS) and next-generation sequencing, resulting in a fine-resolution map of the sequence-function landscape[8, 9]. We evaluated changes within the C-terminal 52 residues, which contains the binding epitope of FcB6, using Illumina Miseq paired-end sequencing. We simplified the sequence analysis by assuming that all mutations are additive in their contribution to binding, and identified enriched and depleted mutations (data not shown). The core residues, S134, Q164, F167 and Y168, at the designed interface with Fc are highly conserved. The sequence fitness landscape suggests L171 could be switched to Trp; modeling of this substitution shows that it increases the packing density, adding more surface area for binding as well as forming an additional hydrogen bond to Fc Asn315. However, deep sequencing of sort 2 shows depletion of L171W under more stringent selection conditions. Further, two amino acid residues that originated from the wildtype scaffold (K142, K158) were conserved, likely due to contributions to the overall electrostatic complementarity of the complex. The two positions that allow the most substitutions are E135 and A138. Substitutions of these identities were also identified as consensus after 3 rounds of sorting and conventional sequencing (data not shown).

To optimize both binding and pH-dependent behavior, we constructed a library, guided by the deep sequencing data and Rosetta energy calculations, and carried out rounds of selection for increased binding affinity under two different pH conditions (pH 6.5 and 8). In the library, L166 was substituted with a phenylalanine, S124 and A165 were allowed to be either alanine or serine, and E135, A138, K170, E160 and M161 were allowed to be any of the 20 amino acids. Six clones from the 4th round of sorting were screened for binding at pH 6.5 and pH 8, and the variant with the largest difference (6-7 fold greater signal at pH 8 than pH 6.5 on the yeast surface) was subjected to more detailed analysis and will be referred to as FcB6.1. FcB6.1 contains the substitution E138V and an additional positive charge, A135R. Structural modeling of the designed variant shows a nearly perfect fit around Fc His433: R135 covers and packs against this residue, and also interacts favorably with the close-by highly negatively charged surface on Fc. Modeling rationalized this choice of substitutions by suggesting that protonation of Fc His433 would considerably reduce binding affinity by eliminating a buried hydrogen bond to Ser134, increasing the cost of desolvation for the histidine, and resulting in charge repulsion between the positive charge of Arg135 of FcB6.1 and the protonated (positively charged) His433. The FcB6.1 variant contains several additional mutations including M161F, which increases the buried hydrophobic surface area at the interface, and reduces the identical residues with Protein A to 3 residues only, and E160T, which reduces the negative charge projected towards CH3.

Protein production yields and stability are key determinants for the usefulness of affinity reagents. FcB6.1 is an attractive candidate in this regard as it is derived from a protein scaffold of a hyperthermophilic organism. FcB6.1 expresses well in E. coli, yielding around ~60-70 mg/L in shake flasks without any optimization, and is very stable. CD spectral analysis indicates melting only starts at temperatures higher than 80° C. FcB6.1 can be readily obtained in nearly pure form by subjecting bacteria to 80° C. for 20 min followed by centrifugation. FcB6.1 is stable to urea up to 3 M and guanidine HCl up to 1.5 M guanidine. Also, repeated heating cycles up to 80° C. did not denature the protein. Thus, FcB6.1 has considerable potential utility in chip- or bead-based assays and diagnostics: a simple heating procedure or denaturant wash would allow recovery of the antibody capture agent.

To examine the specificity of FcB6.1, we measured binding to biotinylated human IgG from different subclasses and commonly used IgGs from other species. Binding of the IgGs to the minimized Protein A variant[10] (miniA) was measured for comparison. As expected FcB6.1 binds tightly to human IgG2, IgG4 and IgG1, slightly better than the miniA, and comparably to mouse IgG1 and IgG2a. FcB6.1 only binds weakly to IgG3 (which Protein A does not bind), and unlike Protein A, weakly to rat IgG2a.

Surface plasmon resonance measurements of the purified protein indicated a dissociation constant of around 33 nM to immobilized Rituxan at pH 8.2 and severely reduced affinity (>1 µM) at pH 5.5; very favorable characteristics for pH dependent chromatography. To test whether FcB6.1 could serve for affinity purification of IgG molecules, we added a C-terminal cysteine residue accompanied by a short glycine serine linker to couple the protein site-specifically to a resin (SulfoLink, Thermo Scientific). To simulate a possible purification scenario, we spiked an IgG mix (20 μg, Innovative™ Research) into the supernatant of 293 Freestyle cell culture and incubated it with FcB6.1cys coated resin while rotating (see Methods). Almost complete elution was achieved by dropping the pH to 5.5 to ensure complete protonation of His433 and increasing the salt concentration to 500 mM (instead of commonly used 150 mM). Compared to Protein A, the FcB6.1cys resin allows much milder conditions for elution, which can be crucial for antibodies that tend to aggregate and particularly to Fc-fusion constructs; indeed higher molecular weight aggregates were observed after elution from a Protein A resin under same conditions.

Partition of FcB6 and Variants
Combinatorial Libraries to Evaluate Changes to One of the Interface Helices: Residues 157-172

Figure 4:
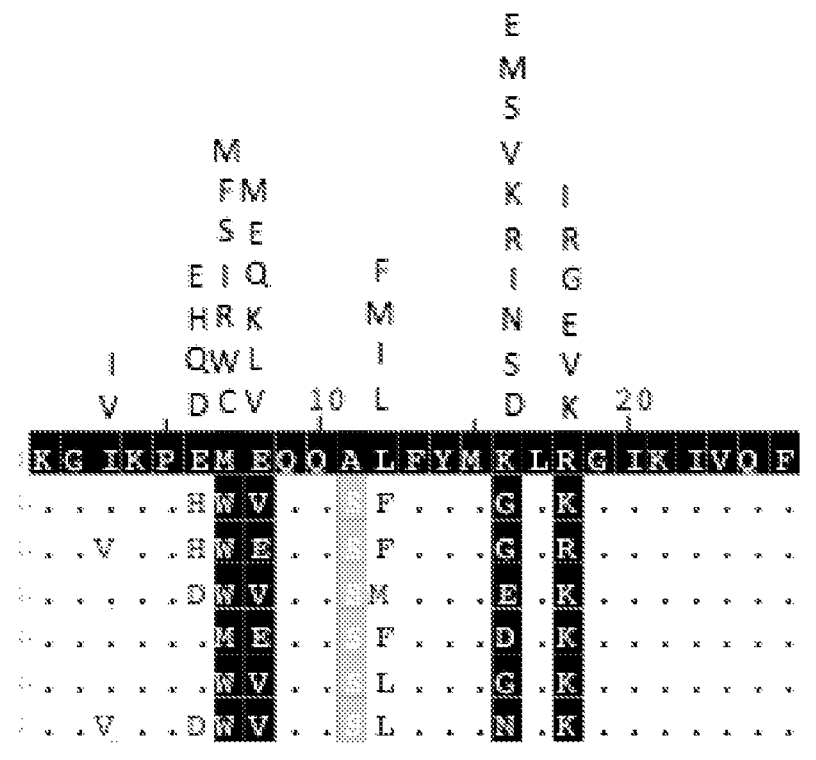

To test small changes around the core interface helix that is similar to Protein A (4 residues in the original design, 3 in the FcB6.1 variants), we tested a combinatorial library for binding and found the consensus shown in FIG. 4 after 3 rounds of sorting:

Evaluation of pH Dependent Binding Through Point Mutations

To narrow down the residues that are responsible for the high pH sensitivity, we introduced "reverting" mutations to the optimized clone FcB6.1; this means we introduced single mutations back to the original design before optimization. Mutations demonstrated that the A135R and E138V were crucial mutations for pH dependence as well as binding.

FcB6.1
(SEQ ID NO: 144)
PEEALIVVDMQRDFMPGGALPVPEGDKIIPKVNEYIRKFKEKGALIVATR

DWHPENHISFRERGGPWPRHCVQNTPGAEFVVDLPEDAVIISKATEPDKE

AYSGFEGTDLAKILRGNGVKRVYICGVATEYAVSRTAVDALKHGFEVYLL

RDAVKGIKPTFEQQSFFYMSLKGIKIVQF

Summary:
Two Alpha Helix Peptide Stretches Define the Functional Sites

The interface of FcB6 consists of two alpha helices that bind to the region between CH2 and CH3 domain of an IgG. They can be at any length as long as they are within a certain distance that allows them to interact with each other. The most C-terminal helix (Z1 in general formula 1) buries the crucial histidine 433 of the IgG it binds to. In FcB6.1 (or Fc24.47), this helix contains the sequence (E130-H143)
(SEQ ID NO: 17)
EYCVSRTAVDALKH Ra1-Ra2-Ra3-Ra4-Ra5-Ra6-Ra7-Ra8-Ra9-Ra10-Ra11-

Ra12-Ra13-Ra14

Note: Ra3Cys (C132) used to be the active site residue, it is mutated into Ala for any application, such as affinity chromatography.

The specific residues that are preferred for the pH dependent contact are Ra5 Ser (S134) and Ra6 Arg (R135). Ra9 Val can be replaced but is preferred at this position.

The second helix (Z3 in general formula 1) buries the crucial histidine 433 of the IgG it binds to. This helix contains the information about pH dependent binding. The sequence of this helix in FcB6.1 is (positions T160-K172)
(SEQ ID NO: 49)
TFEQQSFFYMSLK Rb1-Rb2-Rb3-Rb4-Rb5-Rb6-Rb7-Rb8-Rb9-Rb10-Rb11-

Rb12-Rb13 in which Rb2-F, Rb5-Q, Rb8-F and Rb9-Y build the core of the binding interaction
Changes are allowed in helix 2, but it is preferred that residues Rb5, Rb8 and Rb9 are Q, F, and Y, respectively.

In summary, we have demonstrated that computational protein design can be readily employed to design affinity reagents with very favorable characteristics for biotechnology. Here, we targeted the consensus-binding site within the Fc hinge region of an IgG antibody, based on the natural Fc interaction with Protein A, but also introduced specificity for the protonation state of His433. The ability to engineer pH sensitivity will be of benefit for various fields, such as drug delivery, biosensors and as addressed here affinity chromatography.

Methods
Computational Methods

The hotspot residues Gln11, Phe14 and Leu18 of the minimized Protein A structure (1BBx) were excised and the disembodied hydrophobic residues were subjected to small docking perturbations against the Fc surface to generate "hotspot libraries" (FIG. 1B-C, Fig. S1), whereas for the glutamine residue, additional inverse rotameric conformations were computed (FIG. 1C). The same procedure was repeated for tryptophan residues instead of the phenylalanine and asparagine instead of glutamine resulting in a total of 3 independent residue libraries. To prepare the starting configurations of all 865 preselected structures of our scaffold set[4], each one of these structures was docked against Fc using patchdock[11], with the constraint to bury Ile253, Met252, Met428 or Tyr436 using the "knob" features, out of which we sampled the top 100 conformations for 2 different protocols. Two protocols for RosettaScripts[12] were generated, Fc-2stubs.xml and Fc-3stubs.xml (Suppl.), with the first protocol only considering 2 hotspot libraries, the glutamine based stubs and phenylalanine stub set. The second protocol included all three hotspot libraries, the third being derivatives of Leu18 (Fig. S1). To prune the list of resulting designs, next to computed binding energy, shape complementarity[13] (>0.63) was applied calculated using the CCP4 package v. 6.0.2[14]. Beneficial mutations identified via yeast binding selections were computed using FoldIt[15]. Poisson Boltzman electrostatic surface models were computed using APBS[16].

Antibody Biotinylation

All antibodies were biotinylated using SoluLink's biotinylation kit as instructed by the manufacturer.

Initial Design Evaluation and Yeast Surface Titrations

Yeast surface display and titrations were done similar as previously described[17]. Yeast cells (EBY100) containing plasmid encoding the designs, were grown overnight at 30° C. in SDCAA medium. For induction, they were subcultured into SGCAA to achieve an O.D. of 1, and grown at 22° C. for 16-20 h. Cells were washed once with PBS containing 0.5% BSA (PBS-BSA), before adding 700 nM biotinylated IgG (Rituximab) into a total volume of 50 μl of the same buffer. Labeling was performed at 4° C. on a rotating platform for 4 h before adding 175 nM streptavidin-PE (Invitrogen) and 4-8 µg/ml FITC labeled anti-Cmyc antibody (ICL labs) for an additional 1 h. Cells were washed once with ice cold PBS-BSA immediately before measuring their fluorescence via an Accuri C6 flow cytometer, data was analyzed using the FlowJo 7.6.1 and 8.8.7 software.

Library Constructions

Error prone mutagenesis was achieved through a Mutazyme II DNA polymerase kit (Agilent-Stratagene). 100 ng of the FcB6 gene in pETCON were subjected to 30 cycles of amplification. Mutagenized PCR fragments were co-transformed[18] with linearized pETCON vector[4] into EBY100 resulted in 1.5×10e8 variants. 10 individual clones were conventionally sequenced, indicating an average error rate of around 3 nucleotide substitutions per gene. The focused library was constructed through PCR using ultramer oligonucleotides with degenerate codons for the described positions, with upGS and downCmyc primers (Table S2). Resulting two fragments were co-transformed with linearized plasmid. After transformation into yeast, this library contained around 5×10e7 variants.

Library Selections

The epPCR library of the original design was incubated while rotating for 4 h at 4° C. with 750 nM biotinylated Rituxan and an additional hour with 187.5 nM streptavidin-PE and 2 µg/ml anti-myc Fitc-labeled antibody. 6.17×10e7 cells were examined and 106,000 cells were selected using fluorescence-activated cell sorting on a BD Influx sorter. For the second, focused library, 4 sorts were performed using 100 nM, 100 nM, 20 nM and 5 nM of biotinylated Rituxan under non-avid conditions[17].

Library Preparation and Next-Generation Sequencing

Plasmids were extracted similarly as previously described[9]. Briefly, around 5×10e7 cells were treated with zymolase 50 U in 400 µl Solution buffer 1 (Zymo Research yeast plasmid miniprep II) and incubated at 37° C. for 4 h and vortexed every hour. Cells were freeze-thawed once and treated as instructed in Zymo kit manual with the exception that lysate was applied to higher-yield columns (QIAgen, plasmid miniprep kit), followed by plasmid elution with 30 µl EB (QIAgen). Possible contaminating genomic DNA was eliminated through digestion with ExoI (NEB) and Lambda exonuclease (NEB) as described[9]. After a QIAgen PCR clean-up step, Illumina adapters and population specific-barcodes were added through PCR (Suppl.). PCR product was purified through gel extraction (QIAgen). A total of 330 µl of a 7 pM solution was combined with 270 µl of a 6 pM PhiX v3 control (Illumina) and sequenced with a 300 bp cycle kit V1 using a Miseq (Illumina) with appropriate sequencing primers (Table S1), resulting in a forward and reverse read of the 153 bp long C-terminus. After quality filtering 942,049 sequences of the naïve population were compared to 375,962 of the selected pool.

Sequencing Analysis

Sequencing reads were split based on their 8 bp barcode into naïve and sorted population. Pools were treated identically in sequence analysis and quality filtration. Custom scripts were used to align all paired-end reads with both reads above an average Phred quality score above 10. Reads without gaps were merged into a single sequence and differences between sequences resolved using the higher quality score for the read. Sequences were counted and compared through custom python scripts similar to previously reported[8, 9].

Cloning, Expression and Purification

FcB6.1 variants were codon optimized using DNAworks using standard *E. coli* codons. Variants were cloned into pET29b using the NdeI and XhoI sites. Point mutations were generated through overlap PCR, and terminal cysteine addition was achieved through extended primers (Table S1). Mutation C132A was introduced through overlap PCR (Table S1). Protein variants were expressed in LB or TB media at 37° C. for 4 or 16 h through induction with 1 mM IPTG. For purification, cells were resuspended in 50 mM Tris 150 mM NaCl buffer, heated to 80° C. for 20 min and debris eliminated through centrifugation. Protein was then applied to a standard Ni-column.

Binding Analysis

The affinity of the design variants FcB6.1-C132A was determined using a Biacore T100 that was provided by the Analytical Biopharmacy Core facility. A streptaviding-coated chip (Biacore, Uppsala, Sweden) was coated with 300 RU of biotinylated Rituxan. FcB6.1-C132A was titrated in either TBS-BP (25 nM Tris at pH 8.2 with 0.1% BSA and 0.005% (v/v) P20) or PBS-BP (25 mM PBS at pH 5.5 with 0.1% BSA and (v/v) 0.005% P20. The protein was applied at a flow rate of 100 µl/min with 60 sec for association and 90 sec for dissociation. For regeneration of the unbound antibody, two cycles of 20 sec at 20 µl/min of a 100 mM glycine solution at pH 3 were allowed.

Resin Coupling

A buffer exchanged was performed into 25 mM Tris pH 8.2. 25 mM TCEP was used for at least 1 h at room temperature, to reduce possibly disulfide-bonded dimers. About 3 mg of protein per 1 ml SulfoLink resin material (Thermo Scientific) was incubated following procedures from the instruction manual. Resin was washed with 10 column volumes of 25 mM Tris at pH 8.2 with 500 mM NaCl, followed by 10 column volumes 25 mM Tris pH 8.2 followed by incubation with 50 mM cysteine as instructed by the manufacture's manual. After final wash with Tris-NaCl followed by washing with TBS column was ready to use.

IgG Purification

20 µg of a human IgG mix (Innovative Research, Inc.) was spiked into 1 ml of 293 Freestyle suspension cell supernatant. Suspension cells were harvested after 2 weeks of expressing an unrelated protein, when the cell density reached 2-3×10e6 cells/ml. To adjust the pH of the supernatant, 1/100 of 1 M Tris pH 8.2 were added and the supernatant-IgG mix was incubated while rotating for 30 min at 4° C. 500 µl resin was allowed to settle and washed with 10 column volumes TBS at pH 8.2. Antibodies were eluted with 25 mM phosphate buffer with 500 mM NaCl at 5.5, or with 100 mM glycine buffer at pH 3. For comparison to Protein A, a agarose resin (Pierce) was purchased and purification was done in the same manner. The version of FcB6.1 that was tethered to agarose was bound through a C-terminal cysteine that was genetically added through a linker: GGGSCLEHHHHHH(SEQ ID NO: 183).

CD Spectrum

CD data were collected on an Aviv 420 spectrometer. Far-UV CD wavelength scans (260-200 nm) at 25 µM protein concentration, with either different urea or guanidine hydrochloride (gua) concentrations, and temperature ranges (25-95° C.) were collected in a 1 mm path length cuvette. Temperature induced protein denaturation was followed by the change in ellipticity at 220 nm in a 1 mm path length cuvette.

REFERENCES

1. Rathin Das, J. M. Antibody Therapeutics: Product Development, Market Trends, and Strategic Issues. (D&MD Publications, 2004).

2. Kelley, B. Industrialization of mAb production technology: the bioprocessing industry at a crossroads. *MAbs* 1, 443-452 (2009).
3. Murtaugh, M. L., Fanning, S. W., Sharma, T. M., Terry, A. M. & Horn, J. R. A combinatorial histidine scanning library approach to engineer highly pH-dependent protein switches. *Protein Sci* 20, 1619-1631.
4. Fleishman, S. J. et al. Computational design of proteins targeting the conserved stem region of influenza hemagglutinin. *Science* 332, 816-821.
5. Fleishman, S. J. et al. Hotspot-Centric De Novo Design of Protein Binders. *J Mol Biol.*
6. DeLano, W. L., Ultsch, M. H., de Vos, A. M. & Wells, J. A. Convergent solutions to binding at a protein-protein interface. *Science* 287, 1279-1283 (2000).
7. Du, X. et al. Crystal structure and mechanism of catalysis of a pyrazinamidase from *Pyrococcus horikoshii*. *Biochemistry* 40, 14166-14172 (2001).
8. Fowler, D. M. et al. High-resolution mapping of protein sequence-function relationships. *Nat Methods* 7, 741-746.
9. Whitehead, T. A. et al. Optimization of affinity, specificity and function of designed influenza inhibitors using deep sequencing. *Nat Biotechnol* 30, 543-548.
10. Braisted, A. C. & Wells, J. A. Minimizing a binding domain from protein A. *Proc Natl Acad Sci USA* 93, 5688-5692 (1996).
11. Schneidman-Duhovny, D., Inbar, Y., Nussinov, R. & Wolfson, H. J. PatchDock and SymmDock: servers for rigid and symmetric docking. *Nucleic Acids Res* 33, W363-367 (2005).
12. Fleishman, S. J. et al. RosettaScripts: a scripting language interface to the Rosetta macromolecular modeling suite. *PLoS One* 6, e20161.
13. Lawrence, M. C. & Colman, P. M. Shape complementarity at protein/protein interfaces. *J Mol Biol* 234, 946-950 (1993).
14. Winn, M. D. et al. Overview of the CCP4 suite and current developments. *Acta Crystallogr D Biol Crystallogr* 67, 235-242.
15. Cooper, S. et al. Predicting protein structures with a multiplayer online game. *Nature* 466, 756-760.
16. Baker, N. A., Sept, D., Joseph, S., Holst, M. J. & McCammon, J. A. Electrostatics of nanosystems: application to microtubules and the ribosome. *Proc Natl Acad Sci USA* 98, 10037-10041 (2001).
17. Chao, G. et al. Isolating and engineering human antibodies using yeast surface display. *Nat Protoc* 1, 755-768 (2006).
18. Benatuil, L., Perez, J. M., Belk, J. & Hsieh, C. M. An improved yeast transformation method for the generation of very large human antibody libraries. *Protein Eng Des Sel* 23, 155-159.
19. Martin, W. L., West, A. P., Jr., Gan, L. & Bjorkman, P. J. Crystal structure at 2.8 A of an FcRn/heterodimeric Fc complex: mechanism of pH-dependent binding. *Mol Cell* 7, 867-877 (2001).

We claim:

1. A polypeptide comprising the amino acid sequence of general formula 1 Z1-Z2-Z3 (SEQ ID NO: 1), wherein
Z1 is EY(A/C)VSxTADxxxH (SEQ ID NO: 184);
Z2 is GxxxxLxRxAVKGxKP (SEQ ID NO: 185); and
Z3 is a xxxQQxxFYMxxx (SEQ ID NO: 186), wherein x is any amino acid.

2. The polypeptide of claim 1, wherein Z1 is selected from the group consisting of

```
                        (SEQ ID NO: 15)
EYCVSRTAVDAKKH;

(SEQ ID NO: 16)
EYAVSRTAVDALKH;

(SEQ ID NO: 17)
EYCVSRTAVDALKH;

(SEQ ID NO: 18)
EY(A/C)VSRTA(E/V/L/M/A/I/T)DALKH;

(SEQ ID NO: 19)
EY(A/C)VSRTA(E/V/L/R/M/A)DALKH;

(SEQ ID NO: 20)
EY(A/C)VSRTA(E/V/M/A/I/T)DALKH;

(SEQ ID NO: 21)
EY(A/C)VSRTAVDALKH;

(SEQ ID NO: 22)
EY(A/C)VSRTA(V/M)DALKH;

(SEQ ID NO: 23)
EY(A/C)VSRTAMDALKH;

(SEQ ID NO: 24)
EY(A/C)VSRTAADALKH;

(SEQ ID NO: 25)
EY(A/C)VSRTAMDALKH;

(SEQ ID NO: 26)
EY(A/C)VSRTALDALKH;

(SEQ ID NO: 27)
EY(A/C)VSRTAIDALKH;
```

```
                                                     (SEQ ID NO: 28)
        EY(A/C)VSRTATDALKH;

(SEQ ID NO: 29)
        EY(A/C)VSRTAVDALKH (SEQ ID NO: 30)
        EYAVSRTAMDALKH;

(SEQ ID NO: 31)
        EYAVSRTAADALKH;

(SEQ ID NO: 32)
        EYAVSRTAMDALKH;

(SEQ ID NO: 33)
        EYAVSRTALDALKH;

(SEQ ID NO: 34)
        EYAVSRTAIDALKH;

(SEQ ID NO: 35)
        EYAVSRTATDALKH;

(SEQ ID NO: 36)
        EYCVSRTAMDALKH;

(SEQ ID NO: 37)
        EYCVSRTAADALKH;

(SEQ ID NO: 38)
        EYCVSRTAMDALKH;

(SEQ ID NO: 39)
        EYCVSRTALDALKH;

(SEQ ID NO: 40)
        EYCVSRTAIDALKH;
        and (SEQ ID NO: 41)
        EYCVSRTATDALKH.
```

3. The polypeptide of claim 1, wherein Z3 is selected from the group consisting of:

```
                                                     (SEQ ID NO: 47)
        EMEQQAFFYMKLR;

(SEQ ID NO: 48)
        EMEQQALFYMKLR;

(SEQ ID NO: 49)
        TFEQQSFFYMSLK;

(SEQ ID NO: 51)
        (B5)(B6)EQQ(S/A)(F/L)FYM(B5)L(K/R),
``` where B5 and B6 are independently any amino acid;

```
                                                     (SEQ ID NO: 52)
        (G/R/S/M/P/W/V/T/R)(M/L/I/A/E/F)EQQ(S/A)
        (F/L)FYM(B5)L(K/R);

(SEQ ID NO: 53)
        (V/H/K/W)(M/W/I/L/H)EQQ(S/A)(F/L)FYM(B5)L(K/R);

(SEQ ID NO: 54)
        EMEQQALFYMKLK;

(SEQ ID NO: 55)
        VWEQQSFFYMVLK;

(SEQ ID NO: 56)
        HWEQQSFFYMLLK;

(SEQ ID NO: 57)
        HMEQQSFFYMMLK;

(SEQ ID NO: 58)
        KIEQQSFFYMMLK;

(SEQ ID NO: 59)
        WLEQQSFFYMALK;

(SEQ ID NO: 60)
        WLEQQSFFYMQLK;

(SEQ ID NO: 61)
        WLEQQAFFYMELK;

(SEQ ID NO: 62)
        WLEQQSFFYMKLK;

(SEQ ID NO: 63)
        FLEQQSFFYMRLK;

(SEQ ID NO: 64)
        WHEQQSFFYMMLK;

(SEQ ID NO: 65)
        WHEQQSFFYMRLK;

(SEQ ID NO: 66)
        EMEQQALFYMKLK;

(SEQ ID NO: 67)
        GMEQQSFFYMILK;

(SEQ ID NO: 68)
        RLEQQSFFYMTLK;

(SEQ ID NO: 69)
        SLEQQSFFYMNLK;

(SEQ ID NO: 70)
        MIEQQSFFYMRLK;

(SEQ ID NO: 71)
        PIEQQSFFYMHLK;

(SEQ ID NO: 72)
        WLEQQSFFYMHLK;

(SEQ ID NO: 73)
        VLEQQSFFYMDLK;

(SEQ ID NO: 74)
        WAEQQSFFYMGLK;

(SEQ ID NO: 75)
        TEEQQSFFYMTLK;

(SEQ ID NO: 76)
        TFEQQSFFYMSLK;
        and (SEQ ID NO: 77)
        RLEQQSFFYMSLK.
```

4. The polypeptide of claim 1, wherein Z2 has the amino acid sequence

```
                                                     (SEQ ID NO: 85)
        G(F/V)(E/D)(V/G)(Y/C)L(L/F)R(D/E/N)AVKG(I/V/F)KP.
```

5. The polypeptide of claim 1, wherein the polypeptide comprises one of the following amino acid sequences selected from the group consisting of SEQ ID NOs: 117-119.

6. The polypeptide of claim 1, wherein the polypeptide comprises the amino acid sequence of general formula 5, Z4-Z1-Z2-Z3 (SEQ ID NO: 8), wherein Z4 is a peptide of at least between 100-200 amino acids in length.

7. The polypeptide of claim 6, wherein Z4 comprises the amino acid sequence of SEQ ID NO: 120.

8. The polypeptide of claim 1, wherein the polypeptide comprises one of the following amino acid sequences selected from the group consisting of SEQ ID NOs: 141-169 and 172-182.

9. A pharmaceutical composition comprising the polypeptide of claim 1 and a pharmaceutically acceptable carrier.

10. A composition, comprising the polypeptide of claim 1=bound to a solid support.

11. The polypeptide of claim 1, wherein the polypeptide comprises the amino acid sequence of SEQ ID NO:143.

12. The polypeptide of claim 2, wherein Z3 is selected from the group consisting of SEQ ID NOs: 47-49 and 51-77.

13. The polypeptide of claim 2, wherein Z2 has the amino acid sequence of SEQ ID NO:85.

14. The polypeptide of claim 12 wherein Z2 has the amino acid sequence of SEQ ID NO:85.

15. The polypeptide of claim 3 wherein Z2 has the amino acid sequence of SEQ ID NO:85.

16. A method for purifying antibodies or Fc fusion proteins, comprising
  (a) contacting a sample comprising antibodies or Fc fusion proteins with one or more polypeptides according to claim 1 under suitable conditions for binding of antibodies in the sample to the one or more polypeptides to form antibody-polypeptide complexes; and
  (b) dissociating the antibody from the antibody-polypeptide complexes, to isolate the antibody.

17. A method for detection of an antibody or Fc fusion protein in a sample, comprising
  (a) contacting a sample comprising antibodies or Fc fusion proteins with one or more polypeptides according to claim 1 under suitable conditions for binding of antibodies or Fc fusion protein in the sample to the one or more polypeptides to form antibody-polypeptide complexes; and
  (b) detecting the antibody-polypeptide complexes.

\* \* \* \* \*